United States Patent
Carpenter et al.

(10) Patent No.: US 11,692,213 B2
(45) Date of Patent: *Jul. 4, 2023

(54) COMPOSITIONS AND METHODS FOR TARGETED DEPLETION, ENRICHMENT, AND PARTITIONING OF NUCLEIC ACIDS USING CRISPR/CAS SYSTEM PROTEINS

(71) Applicant: Arc Bio, LLC, Cambridge, MA (US)

(72) Inventors: Meredith L. Carpenter, San Mateo, CA (US); Carlos D. Bustamante, Emerald Hills, CA (US); Stephane B. Gourguechon, San Mateo, CA (US)

(73) Assignee: ARC BIO, LLC, Scotts Valley, CA (US)

( * ) Notice: Subject to any disclaimer, the term of this patent is extended or adjusted under 35 U.S.C. 154(b) by 152 days.

This patent is subject to a terminal disclaimer.

(21) Appl. No.: 16/983,388

(22) Filed: Aug. 3, 2020

(65) Prior Publication Data
US 2021/0189459 A1    Jun. 24, 2021

Related U.S. Application Data

(63) Continuation of application No. 15/537,962, filed as application No. PCT/US2015/066949 on Dec. 19, 2015, now Pat. No. 10,774,365.

(60) Provisional application No. 62/198,097, filed on Jul. 28, 2015, provisional application No. 62/094,980, filed on Dec. 20, 2014.

(51) Int. Cl.
| | | |
|---|---|---|
| C12N 15/00 | (2006.01) | |
| C12Q 1/6806 | (2018.01) | |
| C12N 9/22 | (2006.01) | |
| C12N 15/11 | (2006.01) | |
| C12Q 1/6874 | (2018.01) | |

(52) U.S. Cl.
CPC .......... C12Q 1/6806 (2013.01); C12N 9/22 (2013.01); C12N 15/11 (2013.01); C12Q 1/6874 (2013.01); C12N 2310/20 (2017.05); C12N 2800/80 (2013.01)

(58) Field of Classification Search
CPC ...... C12Q 1/6806; C12Q 1/6874; C12N 9/22; C12N 15/11; C12N 2310/20; C12N 2800/80
See application file for complete search history.

(56) References Cited

U.S. PATENT DOCUMENTS

| | | |
|---|---|---|
| 5,948,902 A | 9/1999 | Honkanen et al. |
| 9,249,460 B2 | 2/2016 | Pushkarev et al. |
| 9,725,765 B2 | 8/2017 | Pushkarev et al. |
| 2005/0053947 A1 | 3/2005 | Hager et al. |
| 2005/0233340 A1 | 10/2005 | Barrett et al. |
| 2009/0318305 A1 | 12/2009 | Lin et al. |
| 2013/0298265 A1 | 11/2013 | Cunnac et al. |
| 2014/0045705 A1 | 2/2014 | Bustamante et al. |
| 2014/0068797 A1 | 3/2014 | Doudna et al. |
| 2014/0134610 A1 | 5/2014 | Pham et al. |
| 2014/0186843 A1 | 7/2014 | Zhang et al. |
| 2014/0356867 A1* | 12/2014 | Peter .................... C12Y 301/00 536/23.1 |
| 2014/0357523 A1 | 12/2014 | Zeiner et al. |
| 2015/0031089 A1 | 1/2015 | Lindstrom |
| 2015/0071901 A1 | 3/2015 | Liu et al. |
| 2015/0133391 A1 | 5/2015 | de Vlaminick et al. |
| 2015/0211058 A1 | 7/2015 | Carstens |
| 2015/0225773 A1 | 8/2015 | Farmer et al. |
| 2015/0232834 A1 | 8/2015 | Bustamante et al. |
| 2015/0360194 A1 | 12/2015 | Bustamante et al. |
| 2016/0017396 A1* | 1/2016 | Cann .................... C12N 15/102 506/26 |
| 2016/0053304 A1 | 2/2016 | Wurtzel et al. |
| 2016/0208241 A1 | 7/2016 | Tsai et al. |
| 2017/0016048 A1 | 1/2017 | Blauwkamp et al. |
| 2017/0088887 A1 | 3/2017 | Makarov et al. |
| 2017/0191123 A1 | 7/2017 | Kim et al. |
| 2018/0051320 A1 | 2/2018 | DeRisi et al. |
| 2018/0237851 A1 | 8/2018 | Christians et al. |
| 2018/0298421 A1 | 10/2018 | Carpenter et al. |
| 2018/0312830 A1 | 11/2018 | Gourguechon et al. |

FOREIGN PATENT DOCUMENTS

| | | |
|---|---|---|
| EP | 2635679 | 4/2017 |
| WO | 2013141680 | 9/2013 |
| WO | 2013142578 | 9/2013 |
| WO | 2013191775 | 12/2013 |
| WO | 2014150624 | 9/2014 |
| WO | 2014182574 | 11/2014 |
| WO | 2014189957 | 11/2014 |
| WO | 2015070083 | 5/2015 |
| WO | 2015075056 | 5/2015 |

(Continued)

OTHER PUBLICATIONS

Certified of priority document U.S. Appl. No. 62/094,980, filed Dec. 20, 2014, 45 pages.

(Continued)

*Primary Examiner* — Catherine S Hibbert

(74) *Attorney, Agent, or Firm* — Quarles & Brady, LLP

(57) ABSTRACT

Provided herein are methods and compositions for depleting targeted nucleic acid sequences from a sample, enriching for sequences of interest from a sample, and/or partitioning of sequences from a sample. The methods and compositions are applicable to biological, clinical, forensic, and environmental samples.

14 Claims, 12 Drawing Sheets

Specification includes a Sequence Listing.

(56) References Cited

FOREIGN PATENT DOCUMENTS

| WO | 2015119941 | 8/2015 |
|---|---|---|
| WO | 2015122967 | 8/2015 |
| WO | 2015123314 | 8/2015 |
| WO | 2015183025 | 12/2015 |
| WO | 2016014409 | 1/2016 |
| WO | 2016028843 | 2/2016 |
| WO | 2016100955 | 6/2016 |
| WO | 2016196805 | 12/2016 |
| WO | 2017031360 | 2/2017 |
| WO | 2017062599 | 4/2017 |
| WO | 2017066588 | 4/2017 |
| WO | 2018035062 | 2/2018 |
| WO | 2018069430 | 4/2018 |

OTHER PUBLICATIONS

Certified of priority document U.S. Appl. No. 62/198,097, filed Jul. 28, 2015, 71 pages.
De Koning, et al. (2011), "Repetitive Elements May Comprise Over Two-Thirds of the Human Genome" PLOS Genetics 12 pages.
Carbo, et al. (2022) "Longitudinal Monitoring of DNA Viral Loads in Transplant Patients Using Quantitative Metagenomic Next-Generation Sequencing" Pathogens 14 pages.
Sam, et al. (2021) "Evaluation of a Next-Generation Sequencing Metagenomics Assay to Detect and Quantify DNA Viruses in Plasma from Transplant Recipients" The Journal of Molecular Diagnostics, 13 pages.
Carpenter, et al. (2019) "Metagenomic Next-Generation Sequencing for Identification and Quantitation of Transplant-Related DNA Viruses" Journal of Clinical Microbiology, 12 pages.
Head, et al. (2014) "Library construction for next-generation sequencing: Overviews and challenges" Biotechniques, 31 pages.
European Patent Office, Written Opposition for Patent EP3234200, dated Apr. 7, 2022.
Briner, A.E. et al. (2014). "Guide RNA functional modules direct Cas9 activity and orthogonality," Mol. Cell. 56(2):333-339.
Buenrostro, J.D. et al. (2013). "Transposition of native chromatin for multimodal regulatory analysis and personal epigenomics," Nature Methods 10:1213-1218. epub doi:10.1038/nmeth.2688, pp. 1-15 provided.
Carpenter, M.L. et al. (2013). "Pulling out the 1%: whole-genome capture for the targeted enrichment of ancient DNA sequencing libraries," Am. J. Human Genet. 93:852-864.
Cebrian-Serrano, A. and Davies, B. (2017). "CRISPR-Cas orthologues and variants: optimizing the repertoire, specificity and delivery of genome engineering tools," Mammalian Genome 28:247-261.
Cencic, R. et al. (2014). "Protospacer adjacent motif (PAM)-distal sequences engage CRISPR Cas9 DNA target cleavage," PLoS One 9:e109213, 13 total pages.
Cong, L. et al. (2013). "Multiplex genome engineering using CRISPR/Cas systems," Science 339:819-823. epub doi 10.1126/science.1231143, pp. 1-9 provided.
Day, K. et al. (2014). "Targeted sequencing of large genomic regions with CATCH-Seq," PLoS One 9(10):e111756. pp. 1-11 provided.
Dolinsek, J. et al. (2013). "Depletion of unwanted nucleic acid templates by selective cleavage: LNAzymes, catalytically active oligonucleotides containing locked nucleic acids, open a new window for detecting rare microbial community members," App. Environ. Microbiol. 79:1534-1544.
Extended European Search Report dated Apr. 20, 2018, for EP Application No. 15 871 259.6, filed on Dec. 19, 2015, 12 pages.
Extended European Search Report dated Jan. 8, 2019, for EP Application No. 16 837 863.6, filed on Aug. 18, 2016, 6 pages.
Feehery, G.R. et al. (2013). "A method for selectively enriching microbial DNA from contaminating vertebrate host DNA," PLoS One 8(10):e76096. pp. 1-13 provided.
Final Office Action dated Jan. 24, 2020, for U.S. Appl. No. 16/231,338, filed Dec. 21, 2018, 26 pages.
Fonfara, I et al. (2014). "Phylogeny of Cas9 determines functional exchangeability of dual-RNA and Cas9 among orthologous type II CRISPR-Cas systems," Nucleic Acids Research 42:2577-2590.
Fu, Y. et al. (2014). "Improving CRISPR-Cas nuclease specificity using truncated guide RNAs," Nat. Biotechnol. 32:279-284 and additional 2 pp. supplement and 1 p. erratum provided.
Fujita, T. et al. (2013). "Efficient isolation of specific genomic regions and identification of associated proteins by engineered DNA-binding molecule-mediated chromatin immunoprecipitation (enChIP) using Crispr," Biochem. Biophys. Res. Commun. 439:132-136.
Fusi, N. et al. (2015). "In silico predictive modeling of CRISPR/Cas9 guide efficiency," bioRxiv p. 1-31.
Garneau, J.E. et al. (2010). "The CRISPR/Cas bacterial immune system cleaves bacteriophage and plasmid DNA," Nature 468:67-71 and 1 p. methods.
Gasiunas, G. et al. (2012). "Cas9-crRNA ribonucleoprotein complex mediates specific DNA cleavage for adaptive immunity in bacteria," PNAS 109:E2579-2586.
Gu, W. et al. (2016). "Depletion of Abundant Sequences by Hybridization (DASH): Using Cas9 to remove unwanted high-abundance species in sequencing libraries and molecular counting applications," Genome Biology 17:41. doi 10.1186/s13059-016-0904-5, pp. 1-13 provided.
International Search Report dated Dec. 20, 2016, for PCT Application No. PCT/US2016/047631, filed on Aug. 18, 2016, 5 pages.
International Search Report dated May 3, 2016, for PCT Application No. PCT/US2015/066949, filed on Dec. 19, 2015, 4 pages.
Javidi-Parsijani, P. et al. (2017). "No evidence of genome editing activity from Natronobacterium gregoryi Argonaute (NgAgo) in human cells," PLoS ONE 12:e0177444, pp. 1-14 provided.
Jinek, M. et al. (2012). "A programmable dual-RNA-guided DNA endonuclease in adaptive bacterial immunity," Science 337:816-821.
Jinek, M. et al. (2013). "RNA-programmed genome editing in human cells," Elife e00471, pp. 1-9.
Kleinstiver, B.P. et al. (2015). "Engineered CRISPR-Cas9 nucleases with altered PAM specificities," Nature 523:481-485. epub doi:10.1038/nature14592, pp. 1-27 provided.
Loman, N.J. et al. (2012). "High-throughput bacterial genome sequencing: an embarrassment of choice, a world of opportunity," Nature Review Microbiol. 10:599-606.
Ma, M. et al. (2013). "A guide RNA sequence design platform for the CRISPR/Cas9 system for model organism genomes," Biomed. Res. Int. 2013, p. 1-4, 4 total pages.
Malina, A. et al. (2013). "Repurposing CRISPR/Cas9 for in situ functional assays," Genes Dev. 27(23):2602-2614.
Morlan, J.D. et al. (2012). "Selective depletion of rRNA enables whole transcriptome profiling of archival fixed tissue," Plos One 7:e42882. pp. 1-8 provided.
Mougiakos, I. et al. (2016). "Next Generation Prokaryotic Engineering: The CRISPR-Cas Toolkit," Trends in Biotechnology 34:575-587.
Non-Final Office Action dated Apr. 8, 2019, for U.S. Appl. No. 15/520,052, filed Apr. 18, 2017, 15 pages.
Non-Final Office Action dated Dec. 13, 2018, for U.S. Appl. No. 15/520,052, filed Apr. 18, 2017, 15 pages.
Non-Final Office Action dated Jul. 5, 2019, for U.S. Appl. No. 15/537,962, filed Jun. 20, 2017, 16 pages.
Notice of Allowance dated Aug. 5, 2019, for U.S. Appl. No. 15/520,052, filed Apr. 18, 2017, 12 pages.
O'Connell, M.R. et al. (2014). "Programmable RNA recognition and cleavage by CRISPR/Cas9," Nature 516:263-266. epub doi 10.1038/nature13769, pp. 1-23 provided.
Ran, F.A. et al. (2013). "Genome engineering using the CRISPR-Cas9 system," Nat. Protoc. 8:2281-2308.
Ran, F.A. et al. (2015). "In vivo genome editing using *Staphylococcus aureus* Cas9," Nature 520(7546):186-191. epub doi 10.1038/nature14299, pp. 1-28 provided.
Shalem, O. et al. (2014). "Genome-scale CRISPR Cas9 knockout screening in human cells," Science 343:84-87. epub doi 10.1126/science.1247005, pp. 1-10 provided.

(56) References Cited

OTHER PUBLICATIONS

Shmakov, S. et al. (2015). "Discovery and Functional Characterization of Diverse Class 2 CRISPR-Cas Systems," Mol. Cell. 60:385-397. epub doi 10.1016/j.,olcel.2015.10.008, pp. 1-23 provided.

Smolina, I.V. et al. (2005). "End invasion of peptide nucleic acids (PNAs) with mixed-base composition into linear DNA duplexes," Nuc. Acids Res. 33(17):e146. pp. 1-9 provided.

Sternberg, S.H. et al. (2015). "Conformational control of DNA target cleavage by CRISPR-Cas9," Nature 527:110-113. epub, pp. 1-21 provided.

Swarts, D.C. et al. (2014). "DNA-guided DNA interference by a prokaryotic Argonaute," Nature 507(7491):258-261. epub doi:10.1038/nature12971, pp. 1-32 provided.

Swarts, D.C. et al. (2017). "Structural basis for guide RNA processing arid seed-dependent DNA targeting by CRISPR-Cas12a," Mol. Cell 66:221-233, and 4 pages supplement.

Wang, T. et al. (2013). "Genetic screens in human cells using the CRISPR-Cas9 system," Science 343:80-84. epub doi:10.1126/science.1246981, pp. 1-12 provided.

Written Opinion of the International Searching Authority dated Dec. 20, 2016, for PCT Application No. PCT/US2016/047631, filed on Aug. 18, 2016, 12 pages.

Written Opinion of the International Searching Authority dated May 3, 2016, for PCT Application No. PCT/US2015/066949, filed on Dec. 19, 2015, 10 pages.

Wu, J. et al. (2014). "OsLOL1, a C2C2-type zinc finger protein, interacts with OsbZIP58 to promote seed germination through the modulation of gibberellin biosynthesis in Oryza sativa," Plant J. 80(6):1118-1130.

Yamano, T. et al. (2016). "Crystal Structure of Cpf1 in Complex with Guide RNA and Target DNA," Cell 165:949-962.

Zetsche, B. et al. (2015). "Cpf1 is a single RNA-guided endonuclease of a class 2 CRISPR-Cas system," Cell 163:759-771.

\* cited by examiner

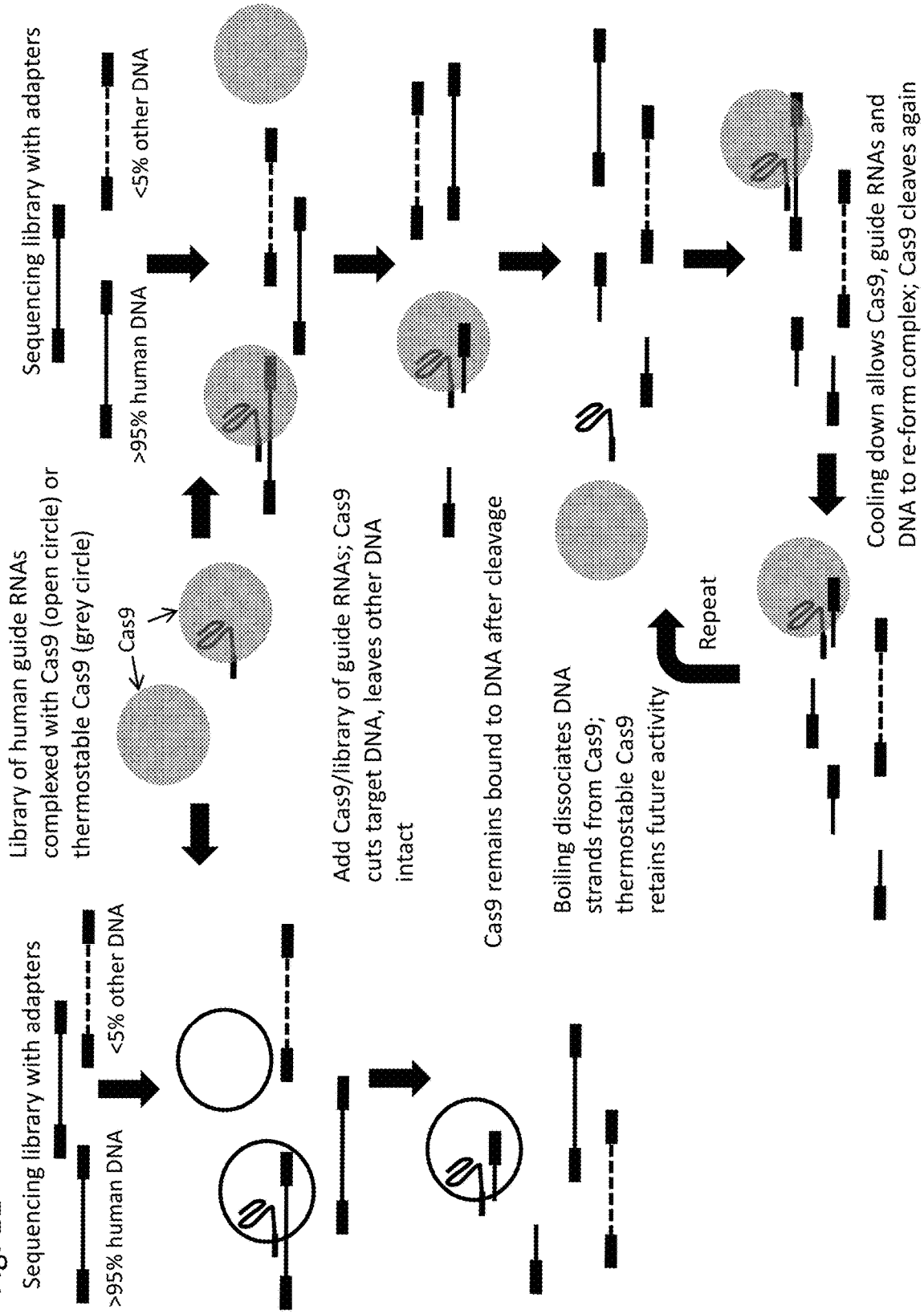

SEQUENCE LISTING

```
<160> NUMBER OF SEQ ID NOS: 102

<210> SEQ ID NO 1
<211> LENGTH: 20
<212> TYPE: DNA
<213> ORGANISM: Artificial Sequence
<220> FEATURE:
<223> OTHER INFORMATION: Synthetic Construct

<400> SEQUENCE: 1
aatgatacgg cgaccaccga                                                 20

<210> SEQ ID NO 2
<211> LENGTH: 21
<212> TYPE: DNA
<213> ORGANISM: Artificial Sequence
<220> FEATURE:
<223> OTHER INFORMATION: Synthetic Construct

<400> SEQUENCE: 2
caagcagaag acggcatacg a                                               21

<210> SEQ ID NO 3
<211> LENGTH: 18
<212> TYPE: DNA
<213> ORGANISM: Artificial Sequence
<220> FEATURE:
<223> OTHER INFORMATION: Synthetic Construct
```

<400> SEQUENCE: 3
cagagcgagg tatgtagg                                                                      18

<210> SEQ ID NO 4
<211> LENGTH: 23
<212> TYPE: DNA
<213> ORGANISM: Artificial Sequence
<220> FEATURE:
<223> OTHER INFORMATION: Synthetic Construct
<220> FEATURE:
<221> NAME/KEY: misc_feature
<222> LOCATION: 1, 2, 3, 4, 5, 6, 7, 8, 9, 10, 11, 12, 13, 14, 15, 16,
      17, 18, 19, 20, 21
<223> OTHER INFORMATION: n = A,T,C or G

<400> SEQUENCE: 4
nnnnnnnnnn nnnnnnnnnn ngg                                                                23

<210> SEQ ID NO 5
<211> LENGTH: 48
<212> TYPE: DNA
<213> ORGANISM: Artificial Sequence
<220> FEATURE:
<223> OTHER INFORMATION: Synthetic Construct
<220> FEATURE:
<221> NAME/KEY: misc_feature
<222> LOCATION: 28
<223> OTHER INFORMATION: May be present or absent
<220> FEATURE:
<221> NAME/KEY: misc_feature
<222> LOCATION: 29, 30, 31, 32, 33, 34, 35, 36, 37, 38, 39, 40, 41, 42,
      43, 44, 45, 46, 47, 48
<223> OTHER INFORMATION: n = A,T,C or G

<400> SEQUENCE: 5
gcctcgagct aatacgactc actataggnn nnnnnnnnn nnnnnnnn                                      48

<210> SEQ ID NO 6
<211> LENGTH: 20
<212> TYPE: DNA
<213> ORGANISM: Artificial Sequence
<220> FEATURE:
<223> OTHER INFORMATION: Synthetic Construct

<400> SEQUENCE: 6
ggatttatac agcactttaa                                                                    20

<210> SEQ ID NO 7
<211> LENGTH: 49
<212> TYPE: DNA
<213> ORGANISM: Artificial Sequence
<220> FEATURE:
<223> OTHER INFORMATION: Synthetic Construct

<400> SEQUENCE: 7
gcctcgagct aatacgactc actataggct cttaaaacta ggcggctag                                    49

<210> SEQ ID NO 8
<211> LENGTH: 48
<212> TYPE: DNA
<213> ORGANISM: Artificial Sequence
<220> FEATURE:
<223> OTHER INFORMATION: Synthetic Construct

<400> SEQUENCE: 8
gcctcgagct aatacgactc actatagatt tacactcaca acaccctg                                     48

<210> SEQ ID NO 9
<211> LENGTH: 48
<212> TYPE: DNA
<213> ORGANISM: Artificial Sequence
<220> FEATURE:
<223> OTHER INFORMATION: Synthetic Construct

<400> SEQUENCE: 9
gcctcgagct aatacgactc actatagaac agctatccat tggtcttg         48

<210> SEQ ID NO 10
<211> LENGTH: 48
<212> TYPE: DNA
<213> ORGANISM: Artificial Sequence
<220> FEATURE:
<223> OTHER INFORMATION: Synthetic Construct

<400> SEQUENCE: 10
gcctcgagct aatacgactc actataggca gccggaagcc tattcgcg         48

<210> SEQ ID NO 11
<211> LENGTH: 48
<212> TYPE: DNA
<213> ORGANISM: Artificial Sequence
<220> FEATURE:
<223> OTHER INFORMATION: Synthetic Construct

<400> SEQUENCE: 11
gcctcgagct aatacgactc actataggta atgaggatgt aagcccgg         48

<210> SEQ ID NO 12
<211> LENGTH: 48
<212> TYPE: DNA
<213> ORGANISM: Artificial Sequence
<220> FEATURE:
<223> OTHER INFORMATION: Synthetic Construct

<400> SEQUENCE: 12
gcctcgagct aatacgactc actatagata tttacaagag gaaaaccg         48

<210> SEQ ID NO 13
<211> LENGTH: 49
<212> TYPE: DNA
<213> ORGANISM: Artificial Sequence
<220> FEATURE:
<223> OTHER INFORMATION: Synthetic Construct

<400> SEQUENCE: 13
gcctcgagct aatacgactc actataggtt tgaagcttag ggagagctg         49

<210> SEQ ID NO 14
<211> LENGTH: 48
<212> TYPE: DNA
<213> ORGANISM: Artificial Sequence
<220> FEATURE:
<223> OTHER INFORMATION: Synthetic Construct

<400> SEQUENCE: 14
gcctcgagct aatacgactc actataggta tggctttgaa gaaggcgg         48

<210> SEQ ID NO 15
<211> LENGTH: 48
<212> TYPE: DNA
<213> ORGANISM: Artificial Sequence
<220> FEATURE:
<223> OTHER INFORMATION: Synthetic Construct

```
<400> SEQUENCE: 15
gcctcgagct aatacgactc actatagtag atgacgggtt gggccagg            48

<210> SEQ ID NO 16
<211> LENGTH: 48
<212> TYPE: DNA
<213> ORGANISM: Artificial Sequence
<220> FEATURE:
<223> OTHER INFORMATION: Synthetic Construct

<400> SEQUENCE: 16
gcctcgagct aatacgactc actatagagc tttacagtgg gctctagg            48

<210> SEQ ID NO 17
<211> LENGTH: 48
<212> TYPE: DNA
<213> ORGANISM: Artificial Sequence
<220> FEATURE:
<223> OTHER INFORMATION: Synthetic Construct

<400> SEQUENCE: 17
gcctcgagct aatacgactc actatagatg gcagcttctg tggaacgg            48

<210> SEQ ID NO 18
<211> LENGTH: 48
<212> TYPE: DNA
<213> ORGANISM: Artificial Sequence
<220> FEATURE:
<223> OTHER INFORMATION: Synthetic Construct

<400> SEQUENCE: 18
gcctcgagct aatacgactc actataggtg gtaagggcga tgagtgtg            48

<210> SEQ ID NO 19
<211> LENGTH: 48
<212> TYPE: DNA
<213> ORGANISM: Artificial Sequence
<220> FEATURE:
<223> OTHER INFORMATION: Synthetic Construct

<400> SEQUENCE: 19
gcctcgagct aatacgactc actatagtcc ataacgctcc tcatactg            48

<210> SEQ ID NO 20
<211> LENGTH: 48
<212> TYPE: DNA
<213> ORGANISM: Artificial Sequence
<220> FEATURE:
<223> OTHER INFORMATION: Synthetic Construct

<400> SEQUENCE: 20
gcctcgagct aatacgactc actatagtct cccttcacca tttccgag            48

<210> SEQ ID NO 21
<211> LENGTH: 48
<212> TYPE: DNA
<213> ORGANISM: Artificial Sequence
<220> FEATURE:
<223> OTHER INFORMATION: Synthetic Construct

<400> SEQUENCE: 21
gcctcgagct aatacgactc actataggcc tatgagtgac tacaaaag            48

<210> SEQ ID NO 22
```

<210> SEQ ID NO 22
<211> LENGTH: 48
<212> TYPE: DNA
<213> ORGANISM: Artificial Sequence
<220> FEATURE:
<223> OTHER INFORMATION: Synthetic Construct

<400> SEQUENCE: 22
gcctcgagct aatacgactc actatagctt tgccgcctgc gaagcagg                    48

<210> SEQ ID NO 23
<211> LENGTH: 48
<212> TYPE: DNA
<213> ORGANISM: Artificial Sequence
<220> FEATURE:
<223> OTHER INFORMATION: Synthetic Construct

<400> SEQUENCE: 23
gcctcgagct aatacgactc actatagatg tctccatcta ttgatgag                    48

<210> SEQ ID NO 24
<211> LENGTH: 48
<212> TYPE: DNA
<213> ORGANISM: Artificial Sequence
<220> FEATURE:
<223> OTHER INFORMATION: Synthetic Construct

<400> SEQUENCE: 24
gcctcgagct aatacgactc actataggga ggcctgcccc cgctaacg                    48

<210> SEQ ID NO 25
<211> LENGTH: 48
<212> TYPE: DNA
<213> ORGANISM: Artificial Sequence
<220> FEATURE:
<223> OTHER INFORMATION: Synthetic Construct

<400> SEQUENCE: 25
gcctcgagct aatacgactc actatagcga gccgagctgg gccagccg                    48

<210> SEQ ID NO 26
<211> LENGTH: 48
<212> TYPE: DNA
<213> ORGANISM: Artificial Sequence
<220> FEATURE:
<223> OTHER INFORMATION: Synthetic Construct

<400> SEQUENCE: 26
gcctcgagct aatacgactc actataggcg agcaggagta ggagagag                    48

<210> SEQ ID NO 27
<211> LENGTH: 48
<212> TYPE: DNA
<213> ORGANISM: Artificial Sequence
<220> FEATURE:
<223> OTHER INFORMATION: Synthetic Construct

<400> SEQUENCE: 27
gcctcgagct aatacgactc actatagcaa cactttctcg gcctatcg                    48

<210> SEQ ID NO 28
<211> LENGTH: 48
<212> TYPE: DNA
<213> ORGANISM: Artificial Sequence
<220> FEATURE:
<223> OTHER INFORMATION: Synthetic Construct

<400> SEQUENCE: 28

```
gcctcgagct aatacgactc actatagact ttgacaaagt tatgaaag          48
```

<210> SEQ ID NO 29
<211> LENGTH: 48
<212> TYPE: DNA
<213> ORGANISM: Artificial Sequence
<220> FEATURE:
<223> OTHER INFORMATION: Synthetic Construct

<400> SEQUENCE: 29

```
gcctcgagct aatacgactc actatagtca aatcaattgg ccaccaag          48
```

<210> SEQ ID NO 30
<211> LENGTH: 48
<212> TYPE: DNA
<213> ORGANISM: Artificial Sequence
<220> FEATURE:
<223> OTHER INFORMATION: Synthetic Construct

<400> SEQUENCE: 30

```
gcctcgagct aatacgactc actatagact cattcaacca atagcccg          48
```

<210> SEQ ID NO 31
<211> LENGTH: 48
<212> TYPE: DNA
<213> ORGANISM: Artificial Sequence
<220> FEATURE:
<223> OTHER INFORMATION: Synthetic Construct

<400> SEQUENCE: 31

```
gcctcgagct aatacgactc actataggtg ctcacacgat aaaccctg          48
```

<210> SEQ ID NO 32
<211> LENGTH: 27
<212> TYPE: DNA
<213> ORGANISM: Artificial Sequence
<220> FEATURE:
<223> OTHER INFORMATION: Synthetic Construct

<400> SEQUENCE: 32

```
aaaacttcta aacgctaatc caagcct                                 27
```

<210> SEQ ID NO 33
<211> LENGTH: 27
<212> TYPE: DNA
<213> ORGANISM: Artificial Sequence
<220> FEATURE:
<223> OTHER INFORMATION: Synthetic Construct

<400> SEQUENCE: 33

```
aaaactagcc gcctagtttt aagagct                                 27
```

<210> SEQ ID NO 34
<211> LENGTH: 27
<212> TYPE: DNA
<213> ORGANISM: Artificial Sequence
<220> FEATURE:
<223> OTHER INFORMATION: Synthetic Construct

<400> SEQUENCE: 34

```
aaaacagggt gttgtgagtg taaatct                                 27
```

<210> SEQ ID NO 35
<211> LENGTH: 27
<212> TYPE: DNA

<213> ORGANISM: Artificial Sequence
<220> FEATURE:
<223> OTHER INFORMATION: Synthetic Construct

<400> SEQUENCE: 35
aaaacaagac caatggatag ctgttct                                27

<210> SEQ ID NO 36
<211> LENGTH: 27
<212> TYPE: DNA
<213> ORGANISM: Artificial Sequence
<220> FEATURE:
<223> OTHER INFORMATION: Synthetic Construct

<400> SEQUENCE: 36
aaaacgcgaa taggcttccg gctgcct                                27

<210> SEQ ID NO 37
<211> LENGTH: 27
<212> TYPE: DNA
<213> ORGANISM: Artificial Sequence
<220> FEATURE:
<223> OTHER INFORMATION: Synthetic Construct

<400> SEQUENCE: 37
aaaaccgggc ttacatcctc attacct                                27

<210> SEQ ID NO 38
<211> LENGTH: 27
<212> TYPE: DNA
<213> ORGANISM: Artificial Sequence
<220> FEATURE:
<223> OTHER INFORMATION: Synthetic Construct

<400> SEQUENCE: 38
aaaacggttt tcctcttgta aatatct                                27

<210> SEQ ID NO 39
<211> LENGTH: 27
<212> TYPE: DNA
<213> ORGANISM: Artificial Sequence
<220> FEATURE:
<223> OTHER INFORMATION: Synthetic Construct

<400> SEQUENCE: 39
aaaacagctc tccctaagct tcaaact                                27

<210> SEQ ID NO 40
<211> LENGTH: 27
<212> TYPE: DNA
<213> ORGANISM: Artificial Sequence
<220> FEATURE:
<223> OTHER INFORMATION: Synthetic Construct

<400> SEQUENCE: 40
aaaaccgcct tcttcaaagc catacct                                27

<210> SEQ ID NO 41
<211> LENGTH: 27
<212> TYPE: DNA
<213> ORGANISM: Artificial Sequence
<220> FEATURE:
<223> OTHER INFORMATION: Synthetic Construct

<400> SEQUENCE: 41
aaaacctggc ccaacccgtc atctact                                27

<210> SEQ ID NO 42
<211> LENGTH: 27
<212> TYPE: DNA
<213> ORGANISM: Artificial Sequence
<220> FEATURE:
<223> OTHER INFORMATION: Synthetic Construct

<400> SEQUENCE: 42
aaaacctaga gcccactgta aagctct                                27

<210> SEQ ID NO 43
<211> LENGTH: 27
<212> TYPE: DNA
<213> ORGANISM: Artificial Sequence
<220> FEATURE:
<223> OTHER INFORMATION: Synthetic Construct

<400> SEQUENCE: 43
aaaaccgttc cacagaagct gccatct                                27

<210> SEQ ID NO 44
<211> LENGTH: 27
<212> TYPE: DNA
<213> ORGANISM: Artificial Sequence
<220> FEATURE:
<223> OTHER INFORMATION: Synthetic Construct

<400> SEQUENCE: 44
aaaacacact catcgccctt accacct                                27

<210> SEQ ID NO 45
<211> LENGTH: 27
<212> TYPE: DNA
<213> ORGANISM: Artificial Sequence
<220> FEATURE:
<223> OTHER INFORMATION: Synthetic Construct

<400> SEQUENCE: 45
aaaacagtat gaggagcgtt atggact                                27

<210> SEQ ID NO 46
<211> LENGTH: 27
<212> TYPE: DNA
<213> ORGANISM: Artificial Sequence
<220> FEATURE:
<223> OTHER INFORMATION: Synthetic Construct

<400> SEQUENCE: 46
aaaactcgga aatggtgaag ggagact                                27

<210> SEQ ID NO 47
<211> LENGTH: 27
<212> TYPE: DNA
<213> ORGANISM: Artificial Sequence
<220> FEATURE:
<223> OTHER INFORMATION: Synthetic Construct

<400> SEQUENCE: 47 aaaactttg tagtcactca taggcct                                 27

<210> SEQ ID NO 48
<211> LENGTH: 27
<212> TYPE: DNA
<213> ORGANISM: Artificial Sequence
<220> FEATURE:

<223> OTHER INFORMATION: Synthetic Construct

<400> SEQUENCE: 48
aaaacctgct tcgcaggcgg caaagct                                              27

<210> SEQ ID NO 49
<211> LENGTH: 27
<212> TYPE: DNA
<213> ORGANISM: Artificial Sequence
<220> FEATURE:
<223> OTHER INFORMATION: Synthetic Construct

<400> SEQUENCE: 49
aaaactcatc aatagatgga gacatct                                              27

<210> SEQ ID NO 50
<211> LENGTH: 26
<212> TYPE: DNA
<213> ORGANISM: Artificial Sequence
<220> FEATURE:
<223> OTHER INFORMATION: Synthetic Construct

<400> SEQUENCE: 50
aaaacgttag cggggggcagg cctcct                                              26

<210> SEQ ID NO 51
<211> LENGTH: 27
<212> TYPE: DNA
<213> ORGANISM: Artificial Sequence
<220> FEATURE:
<223> OTHER INFORMATION: Synthetic Construct

<400> SEQUENCE: 51
aaaacggctg gcccagctcg gctcgct                                              27

<210> SEQ ID NO 52
<211> LENGTH: 27
<212> TYPE: DNA
<213> ORGANISM: Artificial Sequence
<220> FEATURE:
<223> OTHER INFORMATION: Synthetic Construct

<400> SEQUENCE: 52
aaaactctct cctactcctg ctcgcct                                              27

<210> SEQ ID NO 53
<211> LENGTH: 27
<212> TYPE: DNA
<213> ORGANISM: Artificial Sequence
<220> FEATURE:
<223> OTHER INFORMATION: Synthetic Construct

<400> SEQUENCE: 53
aaaacgatag gccgagaaag tgttgct                                              27

<210> SEQ ID NO 54
<211> LENGTH: 27
<212> TYPE: DNA
<213> ORGANISM: Artificial Sequence
<220> FEATURE:
<223> OTHER INFORMATION: Synthetic Construct

<400> SEQUENCE: 54
aaaactttca taactttgtc aaagtct                                              27

```
<210> SEQ ID NO 55
<211> LENGTH: 27
<212> TYPE: DNA
<213> ORGANISM: Artificial Sequence
<220> FEATURE:
<223> OTHER INFORMATION: Synthetic Construct

<400> SEQUENCE: 55
aaaacttggt ggccaattga tttgact                                              27

<210> SEQ ID NO 56
<211> LENGTH: 27
<212> TYPE: DNA
<213> ORGANISM: Artificial Sequence
<220> FEATURE:
<223> OTHER INFORMATION: Synthetic Construct

<400> SEQUENCE: 56
aaaacgggct attggttgaa tgagtct                                              27

<210> SEQ ID NO 57
<211> LENGTH: 27
<212> TYPE: DNA
<213> ORGANISM: Artificial Sequence
<220> FEATURE:
<223> OTHER INFORMATION: Synthetic Construct

<400> SEQUENCE: 57
aaaacagggt ttatcgtgtg agcacct                                              27

<210> SEQ ID NO 58
<211> LENGTH: 94
<212> TYPE: DNA
<213> ORGANISM: Artificial Sequence
<220> FEATURE:
<223> OTHER INFORMATION: Synthetic Construct

<400> SEQUENCE: 58
gttttagagc tagaaatagc aagttaaaat aaggctagtc cgttatcaac ttgaaaaagt          60
ggcaccgagt cggtgctttt tttggatccg atgc                                      94

<210> SEQ ID NO 59
<211> LENGTH: 22
<212> TYPE: DNA
<213> ORGANISM: Artificial Sequence
<220> FEATURE:
<223> OTHER INFORMATION: Synthetic Construct

<400> SEQUENCE: 59
gcctcgagct aatacgactc ac                                                   22

<210> SEQ ID NO 60
<211> LENGTH: 21
<212> TYPE: DNA
<213> ORGANISM: Artificial Sequence
<220> FEATURE:
<223> OTHER INFORMATION: Synthetic Construct

<400> SEQUENCE: 60
aaaaaaagca ccgactcggt g                                                    21

<210> SEQ ID NO 61
<211> LENGTH: 48
<212> TYPE: DNA
<213> ORGANISM: Artificial Sequence
<220> FEATURE:
```

<223> OTHER INFORMATION: Synthetic Construct

<400> SEQUENCE: 61
gcctcgagct aatacgactc actataggtc agtgggggtg aggtaaaa            48

<210> SEQ ID NO 62
<211> LENGTH: 48
<212> TYPE: DNA
<213> ORGANISM: Artificial Sequence
<220> FEATURE:
<223> OTHER INFORMATION: Synthetic Construct

<400> SEQUENCE: 62
gcctcgagct aatacgactc actataggct gatcctccaa atcaccac            48

<210> SEQ ID NO 63
<211> LENGTH: 48
<212> TYPE: DNA
<213> ORGANISM: Artificial Sequence
<220> FEATURE:
<223> OTHER INFORMATION: Synthetic Construct

<400> SEQUENCE: 63
gcctcgagct aatacgactc actataggtt ggtatcctag tgggtgag            48

<210> SEQ ID NO 64
<211> LENGTH: 48
<212> TYPE: DNA
<213> ORGANISM: Artificial Sequence
<220> FEATURE:
<223> OTHER INFORMATION: Synthetic Construct

<400> SEQUENCE: 64
gcctcgagct aatacgactc actataggtt agcctagcca caccccca            48

<210> SEQ ID NO 65
<211> LENGTH: 47
<212> TYPE: DNA
<213> ORGANISM: Artificial Sequence
<220> FEATURE:
<223> OTHER INFORMATION: Synthetic Construct

<400> SEQUENCE: 65
gcctcgagct aatacgactc actatagggc cgttaaacat gtgtcac             47

<210> SEQ ID NO 66
<211> LENGTH: 47
<212> TYPE: DNA
<213> ORGANISM: Artificial Sequence
<220> FEATURE:
<223> OTHER INFORMATION: Synthetic Construct

<400> SEQUENCE: 66
gcctcgagct aatacgactc actataggtt agcgatggag gtaggat             47

<210> SEQ ID NO 67
<211> LENGTH: 48
<212> TYPE: DNA
<213> ORGANISM: Artificial Sequence
<220> FEATURE:
<223> OTHER INFORMATION: Synthetic Construct

<400> SEQUENCE: 67
gcctcgagct aatacgactc actataggta taacctcccc caaaattc            48

```
<210> SEQ ID NO 68
<211> LENGTH: 47
<212> TYPE: DNA
<213> ORGANISM: Artificial Sequence
<220> FEATURE:
<223> OTHER INFORMATION: Synthetic Construct

<400> SEQUENCE: 68
gcctcgagct aatacgactc actataggca ttgcgagacg ctggagc        47

<210> SEQ ID NO 69
<211> LENGTH: 47
<212> TYPE: DNA
<213> ORGANISM: Artificial Sequence
<220> FEATURE:
<223> OTHER INFORMATION: Synthetic Construct

<400> SEQUENCE: 69
gcctcgagct aatacgactc actatagaaa agataaaatt tgaaatc        47

<210> SEQ ID NO 70
<211> LENGTH: 46
<212> TYPE: DNA
<213> ORGANISM: Artificial Sequence
<220> FEATURE:
<223> OTHER INFORMATION: Synthetic Construct

<400> SEQUENCE: 70
gcctcgagct aatacgactc actatagggt ttatcgatta cagaac         46

<210> SEQ ID NO 71
<211> LENGTH: 47
<212> TYPE: DNA
<213> ORGANISM: Artificial Sequence
<220> FEATURE:
<223> OTHER INFORMATION: Synthetic Construct

<400> SEQUENCE: 71
gcctcgagct aatacgactc actatagaaa tctcctaagt gtaagtt        47

<210> SEQ ID NO 72
<211> LENGTH: 46
<212> TYPE: DNA
<213> ORGANISM: Artificial Sequence
<220> FEATURE:
<223> OTHER INFORMATION: Synthetic Construct

<400> SEQUENCE: 72
gcctcgagct aatacgactc actataggg atttagaggg ttctgt          46

<210> SEQ ID NO 73
<211> LENGTH: 47
<212> TYPE: DNA
<213> ORGANISM: Artificial Sequence
<220> FEATURE:
<223> OTHER INFORMATION: Synthetic Construct

<400> SEQUENCE: 73
gcctcgagct aatacgactc actataggaa aggttaaaaa aagtaaa        47

<210> SEQ ID NO 74
<211> LENGTH: 47
<212> TYPE: DNA
<213> ORGANISM: Artificial Sequence
<220> FEATURE:
<223> OTHER INFORMATION: Synthetic Construct
```

<400> SEQUENCE: 74
gcctcgagct aatacgactc actatagagg gtttacgacc tcgatgt          47

<210> SEQ ID NO 75
<211> LENGTH: 47
<212> TYPE: DNA
<213> ORGANISM: Artificial Sequence
<220> FEATURE:
<223> OTHER INFORMATION: Synthetic Construct

<400> SEQUENCE: 75
gcctcgagct aatacgactc actataggag ggtgatggta gatgtgg          47

<210> SEQ ID NO 76
<211> LENGTH: 47
<212> TYPE: DNA
<213> ORGANISM: Artificial Sequence
<220> FEATURE:
<223> OTHER INFORMATION: Synthetic Construct

<400> SEQUENCE: 76
gcctcgagct aatacgactc actataggat aaatcatatt atggcca          47

<210> SEQ ID NO 77
<211> LENGTH: 46
<212> TYPE: DNA
<213> ORGANISM: Artificial Sequence
<220> FEATURE:
<223> OTHER INFORMATION: Synthetic Construct

<400> SEQUENCE: 77
gcctcgagct aatacgactc actataggga atgctggaga ttgtaa           46

<210> SEQ ID NO 78
<211> LENGTH: 47
<212> TYPE: DNA
<213> ORGANISM: Artificial Sequence
<220> FEATURE:
<223> OTHER INFORMATION: Synthetic Construct

<400> SEQUENCE: 78
gcctcgagct aatacgactc actatagaaa ttaagaatgg ttatgtt          47

<210> SEQ ID NO 79
<211> LENGTH: 48
<212> TYPE: DNA
<213> ORGANISM: Artificial Sequence
<220> FEATURE:
<223> OTHER INFORMATION: Synthetic Construct

<400> SEQUENCE: 79
gcctcgagct aatacgactc actataggtt tgtgggttta agtcccat         48

<210> SEQ ID NO 80
<211> LENGTH: 47
<212> TYPE: DNA
<213> ORGANISM: Artificial Sequence
<220> FEATURE:
<223> OTHER INFORMATION: Synthetic Construct

<400> SEQUENCE: 80
gcctcgagct aatacgactc actataggtg atgccagcag ctaggac          47

<210> SEQ ID NO 81
<211> LENGTH: 48

<212> TYPE: DNA
<213> ORGANISM: Artificial Sequence
<220> FEATURE:
<223> OTHER INFORMATION: Synthetic Construct

<400> SEQUENCE: 81
gcctcgagct aatacgactc actataggtt caccgtaggt ggcctgac     48

<210> SEQ ID NO 82
<211> LENGTH: 47
<212> TYPE: DNA
<213> ORGANISM: Artificial Sequence
<220> FEATURE:
<223> OTHER INFORMATION: Synthetic Construct

<400> SEQUENCE: 82
gcctcgagct aatacgactc actatagtgg agggttcttc tactatt     47

<210> SEQ ID NO 83
<211> LENGTH: 47
<212> TYPE: DNA
<213> ORGANISM: Artificial Sequence
<220> FEATURE:
<223> OTHER INFORMATION: Synthetic Construct

<400> SEQUENCE: 83
gcctcgagct aatacgactc actataggtg ttaggaaaag ggcatac     47

<210> SEQ ID NO 84
<211> LENGTH: 47
<212> TYPE: DNA
<213> ORGANISM: Artificial Sequence
<220> FEATURE:
<223> OTHER INFORMATION: Synthetic Construct

<400> SEQUENCE: 84
gcctcgagct aatacgactc actatagatc tgtttttaag cctaatg     47

<210> SEQ ID NO 85
<211> LENGTH: 48
<212> TYPE: DNA
<213> ORGANISM: Artificial Sequence
<220> FEATURE:
<223> OTHER INFORMATION: Synthetic Construct

<400> SEQUENCE: 85
gcctcgagct aatacgactc actataggtt gtgtttaata ttttagt     48

<210> SEQ ID NO 86
<211> LENGTH: 47
<212> TYPE: DNA
<213> ORGANISM: Artificial Sequence
<220> FEATURE:
<223> OTHER INFORMATION: Synthetic Construct

<400> SEQUENCE: 86
gcctcgagct aatacgactc actataggtg gttggtgtaa atgagtg     47

<210> SEQ ID NO 87
<211> LENGTH: 47
<212> TYPE: DNA
<213> ORGANISM: Artificial Sequence
<220> FEATURE:
<223> OTHER INFORMATION: Synthetic Construct

<400> SEQUENCE: 87

```
gcctcgagct aatacgactc actataggaa aacgtaggct tggatta                47
```

<210> SEQ ID NO 88
<211> LENGTH: 47
<212> TYPE: DNA
<213> ORGANISM: Artificial Sequence
<220> FEATURE:
<223> OTHER INFORMATION: Synthetic Construct

<400> SEQUENCE: 88

```
gcctcgagct aatacgactc actatagggc cagtgccctc ctaattg                47
```

<210> SEQ ID NO 89
<211> LENGTH: 47
<212> TYPE: DNA
<213> ORGANISM: Artificial Sequence
<220> FEATURE:
<223> OTHER INFORMATION: Synthetic Construct

<400> SEQUENCE: 89

```
gcctcgagct aatacgactc actatagaaa tccacccctt acgagtg                47
```

<210> SEQ ID NO 90
<211> LENGTH: 47
<212> TYPE: DNA
<213> ORGANISM: Artificial Sequence
<220> FEATURE:
<223> OTHER INFORMATION: Synthetic Construct

<400> SEQUENCE: 90

```
gcctcgagct aatacgactc actataggca tttaccatct cacttct                47
```

<210> SEQ ID NO 91
<211> LENGTH: 47
<212> TYPE: DNA
<213> ORGANISM: Artificial Sequence
<220> FEATURE:
<223> OTHER INFORMATION: Synthetic Construct

<400> SEQUENCE: 91

```
gcctcgagct aatacgactc actatagata aaatatgatt agttctg                47
```

<210> SEQ ID NO 92
<211> LENGTH: 48
<212> TYPE: DNA
<213> ORGANISM: Artificial Sequence
<220> FEATURE:
<223> OTHER INFORMATION: Synthetic Construct

<400> SEQUENCE: 92

```
gcctcgagct aatacgactc actataggta ggagagtgat atttgatc                48
```

<210> SEQ ID NO 93
<211> LENGTH: 47
<212> TYPE: DNA
<213> ORGANISM: Artificial Sequence
<220> FEATURE:
<223> OTHER INFORMATION: Synthetic Construct

<400> SEQUENCE: 93

```
gcctcgagct aatacgactc actatagggt atgagttttt tttgtta                47
```

<210> SEQ ID NO 94
<211> LENGTH: 48
<212> TYPE: DNA
<213> ORGANISM: Artificial Sequence
<220> FEATURE:
<223> OTHER INFORMATION: Synthetic Construct

<400> SEQUENCE: 94
gcctcgagct aatacgactc actataggcc tctcagccga tgaacagt            48

<210> SEQ ID NO 95
<211> LENGTH: 47
<212> TYPE: DNA
<213> ORGANISM: Artificial Sequence
<220> FEATURE:
<223> OTHER INFORMATION: Synthetic Construct

<400> SEQUENCE: 95
gcctcgagct aatacgactc actatagagt gttagagttt ggattag             47

<210> SEQ ID NO 96
<211> LENGTH: 47
<212> TYPE: DNA
<213> ORGANISM: Artificial Sequence
<220> FEATURE:
<223> OTHER INFORMATION: Synthetic Construct

<400> SEQUENCE: 96
gcctcgagct aatacgactc actataggtt tgtgtatgat atgtttg             47

<210> SEQ ID NO 97
<211> LENGTH: 46
<212> TYPE: DNA
<213> ORGANISM: Artificial Sequence
<220> FEATURE:
<223> OTHER INFORMATION: Synthetic Construct

<400> SEQUENCE: 97
gcctcgagct aatacgactc actataggga gtagggttag gatgag              46

<210> SEQ ID NO 98
<211> LENGTH: 47
<212> TYPE: DNA
<213> ORGANISM: Artificial Sequence
<220> FEATURE:
<223> OTHER INFORMATION: Synthetic Construct

<400> SEQUENCE: 98
gcctcgagct aatacgactc actataggac ctagttcaat gaatctg             47

<210> SEQ ID NO 99
<211> LENGTH: 47
<212> TYPE: DNA
<213> ORGANISM: Artificial Sequence
<220> FEATURE:
<223> OTHER INFORMATION: Synthetic Construct

<400> SEQUENCE: 99
gcctcgagct aatacgactc actataggga cgcctcctag tttgtta             47

<210> SEQ ID NO 100
<211> LENGTH: 47
<212> TYPE: DNA
<213> ORGANISM: Artificial Sequence
<220> FEATURE:
<223> OTHER INFORMATION: Synthetic Construct

<400> SEQUENCE: 100
gcctcgagct aatacgactc actataggca ggtgtctcct ctatctt             47

```
<210> SEQ ID NO 101
<211> LENGTH: 47
<212> TYPE: DNA
<213> ORGANISM: Artificial Sequence
<220> FEATURE:
<223> OTHER INFORMATION: Synthetic Construct

<400> SEQUENCE: 101
gcctcgagct aatacgactc actataggat tcaaattatg tgttttt          47

<210> SEQ ID NO 102
<211> LENGTH: 47
<212> TYPE: DNA
<213> ORGANISM: Artificial Sequence
<220> FEATURE:
<223> OTHER INFORMATION: Synthetic Construct

<400> SEQUENCE: 102
gcctcgagct aatacgactc actatagtca tctccggttt acaagac          47
```

COMPOSITIONS AND METHODS FOR TARGETED DEPLETION, ENRICHMENT, AND PARTITIONING OF NUCLEIC ACIDS USING CRISPR/CAS SYSTEM PROTEINS

CROSS-REFERENCE TO RELATED APPLICATIONS

This application is a continuation of U.S. patent application Ser. No. 15/573,962 filed Jun. 20, 2017, which is a national stage filing under 35 U.S.C. § 371 of International Application No. PCT/US2015/066949, filed Dec. 19, 2015, which claims the priority benefit of U.S. Provisional Application Ser. No. 62/094,980, filed on Dec. 20, 2014, and of U.S. Provisional Application Ser. No. 62/198,097, filed on Jul. 28, 2015. The contents of these applications are hereby incorporated by reference herein in their entireties.

REFERENCE TO A SEQUENCE LISTING SUBMITTED VIA EFS-WEB

The content of the ASCII text file of the sequence listing named "155949-00089 Sequence Listing.TXT" which is 18.8 kb in size was created on Jul. 30, 2020, and electronically submitted via EFS-Web herewith the application is incorporated herein by reference in its entirety.

BACKGROUND OF THE INVENTION

Many human clinical DNA samples, or sample libraries such as cDNA libraries derived from RNA, or extracted DNA samples taken from tissue, fluids, or other host material samples contain highly abundant sequences that have little informative value and increase the cost of sequencing. While methods have been developed to deplete these sequences (e.g., via hybridization capture), these methods are often time-consuming and can be inefficient. Moreover hybridization capture often looks to capture the DNA sequences of interest while discarding the remaining sequences. As a result depletion by hybridization capture is not a viable option when the DNA sequences of interest are not known in advance, e.g. when screening a sample to study all microbial or non-host DNA sequences.

While shotgun sequencing of human samples to study microbial DNA can be done, low levels of microbial DNA in many samples has precluded the shotgun sequencing of many complex and/or interesting samples, due to cost. This is true of, for example, a metagenomic analysis of a sample, where the sample contains more than one species of organism (eukaryotic, prokaryotic, or viral organisms). For example, DNA libraries derived from whole human blood often contain >99% human DNA. Therefore, to detect an infectious agent circulating in human blood from shotgun sequencing, one would need to sequence to very high coverage in order to ensure sufficient coverage. Thus much of the cost associated with sequencing high human DNA samples provides relatively little metagenomic data. As a result many human tissue DNA samples are considered unsuitable for metagenomic sequencing merely because the data yield is low compared to the resources required. Thus there is a need in the art to increase microbial DNA yield in high host DNA samples and specifically to increase the percent of microbial DNA being sequenced when sequencing high host endogenous (HHE) DNA samples.

Recent developments in DNA extraction have provided some sequencing techniques to the point that the field of metagenomics has transitioned from focusing on PCR-amplified 16S ribosomal RNA markers to shotgun sequencing of the whole metagenome. However, shotgun sequencing can yield less than desirable results when sequencing HHE DNA samples due to the low percentage of microbial DNA in the overall sample material. Moreover, shotgun sequencing often fails to provide enough information to make an accurate resolution in metagenomic analysis especially when the selected molecules (e.g., 16S ribosomal RNA) represent only a single lineage. Furthermore, 16S ribosomal RNA lineages cannot often differentiate pathogenic from non-pathogenic strains of closely related bacteria, a key goal of clinical metagenomic analysis.

Instead the use of whole genome DNA and RNA sequences is preferred for metagenetic analysis because it provides information from the entire metagenome. Thus there is a need in the art to provide a DNA and RNA sequencing technique for metagenomic analysis in order to derive improved resolution. For example, whole genome analysis of metagenomes from the fecal material of obese and normal weight patients has revealed highly reproducible differences in microbial community structure. These materials tend to have very high microbial DNA content (>99% microbe and <1% human).

In contrast, sequencing libraries derived from many other tissues including human blood, vagina, nasal mucosal membrane, and lung typically contain >90% human and <10% microbial DNA. While samples with <10% microbial DNA can still, with sufficient sequencing, yield enough information for metagenomic analyses, the required amount of sequencing of specimens with less target DNA is costly and thus untenable for many researchers.

Thus there exists a need in the art to achieve a low-cost, efficient method and compositions for metagenomic analyses. Such methods and compositions are provided herein.

All patents, patent applications, publications, documents, web links, and articles cited herein are incorporated herein by reference in their entireties.

BRIEF SUMMARY OF THE INVENTION

Provided herein are methods and compositions for depleting targeted nucleic acid sequences from a sample, enriching for sequences of interest from a sample, and/or partitioning of sequences from a sample. The methods and compositions are applicable to biological, clinical, forensic, and environmental samples.

In one aspect, provided herein is a method of enriching a sample for sequences of interest, comprising: (a) providing a sample comprising sequences of interest and targeted sequences for depletion, wherein the sequences of interest comprise less than 30% of the sample; (b) contacting the sample with a plurality of CRISPR/Cas system protein-gRNA complexes, wherein the gRNAs are complementary to the targeted sequences, and whereby the targeted sequences are cleaved. In any of the embodiments disclosed herein, the method further comprises extracting the sequences of interest and the targeted sequences for depletion from the sample. In any of the embodiments disclosed herein, the method further comprises fragmenting the extracted sequences. In any of the embodiments disclosed herein, the method further comprises adapter ligating the 5' and 3' ends of the fragmented extracted sequences. In any of the embodiments disclosed herein, the cleaved targeted sequences are removed by size-exclusion. In any of the embodiments disclosed herein, the cleaved targeted sequences are removed with the use of biotin. In any of the embodiments disclosed herein, the method further comprises amplifying the sequences of interest. In any of the embodiments disclosed herein, the targeted sequences for depletion are followed by a Protospacer Adjacent Motif or (PAM) sequence. In any of the embodiments disclosed herein, the method comprises contacting the sample with at least $10^2$ unique CRISPR/Cas system protein-gRNA complexes. In any of the embodiments disclosed herein, the sample is any one of a biological sample, a clinical sample, a forensic sample or an environmental sample. In any of the embodiments disclosed herein, the sample comprises host nucleic acid sequences targeted for depletion and non-host nucleic acid sequences of interest. In any of the embodiments disclosed herein, the non-host nucleic acid sequences comprise microbial nucleic acid sequences. In any of the embodiments disclosed herein, the microbial nucleic acid sequences are bacterial, viral or eukaryotic parasitic nucleic acid sequences. In any of the embodiments disclosed herein, the sample is contacted with CRISPR/Cas system protein-gRNA complexes, wherein the gRNAs are complementary to DNA corresponding to ribosomal RNA sequences. In any of the embodiments disclosed herein, the sample is contacted with CRISPR/Cas system protein-gRNA complexes, wherein the gRNAs are complementary to mitochondrial DNA. In any of the embodiments disclosed herein, the sample is contacted with CRISPR/Cas system protein-gRNA complexes, wherein the gRNAs are complementary to sequences encoding globin proteins, sequences encoding a transposon, sequences encoding retroviral sequences, sequences comprising telomere sequences, sequences comprising sub-telomeric repeats, sequences comprising centromeric sequences, sequences comprising intron sequences, sequences comprising Alu repeats, sequences comprising SINE repeats, sequences comprising LINE repeats, sequences comprising dinucleic acid repeats, sequences comprising trinucleic acid repeats, sequences comprising tetranucleic acid repeats, sequences comprising poly-A repeats, sequences comprising poly-T repeats, sequences comprising poly-C repeats, sequences comprising poly-G repeats, sequences comprising AT-rich sequences, or sequences comprising GC-rich sequences. In any of the embodiments disclosed herein, the extracted nucleic acids incudes any one of single stranded DNA, double stranded DNA, single stranded RNA, double stranded RNA, cDNA, synthetic DNA, artificial DNA, and DNA/RNA hybrids. In any of the embodiments disclosed herein, the sequences of interest comprise less than 10% of the extracted nucleic acids. In any of the embodiments disclosed herein, the sequences of interest comprise less than 5% of the extracted nucleic acids. In any of the embodiments disclosed herein, the CRISPR/Cas system protein is Cas9, Cpf1, Cas3, Cas8a-c, Cas10, Cse1, Csy1, Csn2, Cas4, Csm2, or Cm5. In any of the embodiments disclosed herein, the CRISPR/Cas system protein is Cas9. In any of the embodiments disclosed herein, the CRISPR/Cas system protein is catalytically dead, for example the catalytically dead CRISPR/Cas system protein is dCas9. In any of the embodiments disclosed herein, the CRISPR/Cas system protein is a CRISPR/Cas system protein nickase, for example Cas9 nickase. In any of the embodiments disclosed herein, the CRISPR/Cas System protein is thermostable. In any of the embodiments disclosed herein, method further comprises amplifying the product of step (b) using adapter-specific PCR. In any of the embodiments disclosed herein, method further comprises treating the product of step (b) with an enzyme that has exonuclease activity. In any of the embodiments disclosed herein, the enzyme is Exonuclease III or BAL-31. In any of the embodiments disclosed herein, method further comprises including the use of positive control target sequences. In any of the embodiments disclosed herein, method further comprises including the use of negative control gRNAs. In any of the embodiments disclosed herein, the sample is selected from whole blood, plasma, serum, tears, saliva, mucous, cerebrospinal fluid, teeth, bone, fingernails, feces, urine, tissue, and a biopsy.

In another aspect, provided herein is a method of enriching a sample comprising: (a) providing a sample comprising mitochondrial DNA and non-mitochondrial DNA, wherein the mitochondrial DNA and non-mitochondrial DNA are adapter-ligated, and wherein the adapters are ligated to the 5' and 3' ends of the mitochondrial DNA and non-mitochondrial DNA; (b) contacting the sample with a plurality of CRISPR/Cas system protein-gRNA complexes, wherein the gRNAs are complementary to the mitochondrial DNA, thereby generating mitochondrial DNA adapter ligated only on one end and non-mitochondrial DNA adapter ligated on both the 5' and 3' ends; and (c) enriching the sample for non-mitochondrial DNA. In any one of the embodiments disclosed herein, step (c) comprises amplifying the product of step (b) using adapter-specific PCR. In any of the embodiments disclosed herein, step (c) comprises treating the product of step (b) with an enzyme that has exonuclease activity. In any of the embodiments disclosed herein, the enzyme is Exonuclease III or BAL-31. In any of the embodiments disclosed herein, the method is carried out following a method for analyzing genomic DNA comprising treating DNA isolated from a population of cells with an insertional enzyme to produce a plurality of tagged fragments of non-mitochondrial genomic DNA, whereby also generating a residual amount of tagged mitochondrial DNA. In any of the embodiments disclosed herein, the method further comprises extracting the mitochondrial DNA and non-mitochondrial DNA from the sample. In any of the embodiments disclosed herein, the method further comprises fragmenting the extracted sequences. In any of the embodiments disclosed herein, the mitochondrial DNA is removed by size-exclusion. In any of the embodiments disclosed herein, the mitochondrial DNA is removed with the use of biotin. In any of the embodiments disclosed herein, the enriching the sample comprises amplifying the non-mitochondrial DNA. In any of the embodiments disclosed herein, the method comprises contacting the sample with at least $10^2$ unique CRISPR/Cas system protein-gRNA complexes. In any of the embodiments disclosed herein, the CRISPR/Cas system protein is Cas9, Cpf1, Cas3, Cas8a-c, Cas10, Cse1, Csy1, Csn2, Cas4, Csm2, or Cm5. In any of the embodiments disclosed herein, the CRISPR/Cas system protein is Cas9. In any of the embodiments disclosed herein, the CRISPR/Cas system protein is catalytically dead, for example dCas9. In any of the embodiments disclosed herein, the CRISPR/Cas system protein is a CRISPR/Cas system protein nickase, for example Cas9 nickase. In any of the embodiments disclosed herein, the CRISPR/Cas System protein is thermostable. In any of the embodiments disclosed herein, the enriching comprises amplifying the product of step (b) using adapter-specific PCR. In any of the embodiments disclosed herein, the enriching comprises treating the product of step (b) with an enzyme that has exonuclease activity. In any of the embodiments disclosed herein, the enzyme is Exonuclease III or BAL-31.In any of the embodiments disclosed herein, the method further comprises including the use of positive control target sequences. In any of the embodiments disclosed herein, the method further comprises including the use of negative control gRNAs. In any of the embodiments disclosed herein, the sample is selected from whole blood, plasma, serum, tears, saliva, mucous, cerebrospinal fluid, teeth, bone, fingernails, feces, urine, tissue, and a biopsy.

In another aspect, provided herein is a method of enriching a sample comprising: (a) providing a sample comprising nucleic acids from a first genome and nucleic acids from a second genome, wherein the nucleic acids from the first genome are adapter-ligated on their 5' and 3' ends and wherein the nucleic acids from the second genome are adapter-ligated on their 5' and 3' ends; (b) contacting the sample with a plurality of CRISPR/Cas system protein-gRNA complexes, wherein the gRNAs are complementary to sites targeted in the nucleic acids from the first genome, thereby generating nucleic acids from the first genome adapter ligated only on one end and nucleic acids from the second genome adapter ligated on both the 5' and 3' ends; and (c)enriching the sample for nucleic acids from the second genome. In any of the embodiments disclosed herein, the sample further comprises nucleic acids from additional genomes. In any of the embodiments disclosed herein, the first genome is a host genome, and the second genome is a non-host genome. In any of the embodiments disclosed herein, the method comprises contacting the sample with at least $10^2$ unique CRISPR/Cas system protein-gRNA complexes. In any of the embodiments disclosed herein, the nucleic acids are selected from the group consisting of single stranded DNA, single stranded RNA, double stranded DNA, double stranded RNA, DNA/RNA hybrids, cDNA, synthetic DNA, and artificial DNA. In any of the embodiments disclosed herein, the nucleic acids are double stranded DNA. In any of the embodiments disclosed herein, the nucleic acids are DNA, and wherein the contacting of step (b) generates first genome-DNA adapter ligated on the 5' end but not the 3' end and second genome DNA adapter ligated on both the 5' and 3' ends. In any of the embodiments disclosed herein, the nucleic acids are DNA. In any of the embodiments disclosed herein, the DNA is genomic DNA. In any of the embodiments disclosed herein, the CRISPR/Cas system protein is Cas9, Cpf1, Cas3, Cas8a-c, Cas10, Cse1, Csy1, Csn2, Cas4, Csm2, or Cm5. In any of the embodiments disclosed herein, the CRISPR/Cas system protein is Cas9. In any of the embodiments disclosed herein, the targeted sites in the first genome nucleic acids are followed by a Protospacer Adjacent Motif or (PAM) sequence that can be bound by Cas9. In any of the embodiments disclosed herein, the CRISPR/Cas system protein is catalytically dead, for example dCas9. In any of the embodiments disclosed herein, the CRISPR/Cas system protein is a CRISPR/Cas system protein nickase, for example Cas9 nickase. In any of the embodiments disclosed herein, the CRISPR/Cas system protein is thermostable. In any of the embodiments disclosed herein, the first genome is from an organism selected from the group consisting of a human, cow, horse, sheep, pig, monkey, dog, cat, gerbil, bird, mouse, and rat. In any of the embodiments disclosed herein, the second genome is from a prokaryotic organism. In any of the embodiments disclosed herein, the second genome is from an eukaryotic organism. In any of the embodiments disclosed herein, the second genome is from a parasite. In any of the embodiments disclosed herein, the second genome is from a virus, bacterial, fungus, or protozoa. In any of the embodiments disclosed herein, the adapter-ligated first genome nucleic acids and adapter-ligated second genome nucleic acids range from 50-1000 bp. In any of the embodiments disclosed herein, the second genome nucleic acids comprise less than 50% of the total nucleic acids in the sample. In any of the embodiments disclosed herein, the second genome nucleic acids comprise less than 5% of the total nucleic acids in the sample. In any of the embodiments disclosed herein, the sample is any one of a biological sample, a clinical sample, a forensic sample or an environmental sample. In any of the embodiments disclosed herein, step (c) comprises amplifying the product of step (b) using adapter-specific PCR. In any of the embodiments disclosed herein, step (c) comprises treating the product of step (b) with an enzyme that has exonuclease activity. In any of the embodiments disclosed herein, the enzyme is Exonuclease III or BAL-31. In any of the embodiments disclosed herein, step (c) comprises removing the first genome nucleic acids by size-exclusion. In any of the embodiments disclosed herein, step (c) comprises removing the first genome nucleic acids with the use of biotin. In any of the embodiments disclosed herein, the method further comprises amplifying the product of step (b) using adapter-specific PCR. In any of the embodiments disclosed herein, the method further comprises treating the product of step (b) with an enzyme that has exonuclease activity. In any of the embodiments disclosed herein, the enzyme is Exonuclease III or BAL-31. In any of the embodiments disclosed herein, the method further comprises including the use of positive control target sequences. In any of the embodiments disclosed herein, the method further comprises including the use of negative control gRNAs. In any of the embodiments disclosed herein, the sample is selected from whole blood, plasma, serum, tears, saliva, mucous, cerebrospinal fluid, teeth, bone, fingernails, feces, urine, tissue, and a biopsy.

In another aspect, provided herein is a method of enriching a sample comprising: (a) providing a sample comprising host nucleic acids and non-host nucleic acids, wherein the host nucleic acids and non-host nucleic acids are adapter-ligated, and wherein the adapters are ligated to the 5' and 3' ends of the host nucleic acids and the non-host nucleic acids; (b) contacting the sample with a plurality of CRISPR/Cas system protein-gRNA complexes, wherein the gRNAs are complementary to targeted sites in the host nucleic acids, thereby generating host-nucleic acids adapter ligated only on one end and non-host nucleic acids adapter ligated on both the 5' and 3' ends; and (c) enriching the sample for non-host nucleic acids. In any of the embodiments disclosed herein, the method comprises contacting the sample with at least $10^2$ unique CRISPR/Cas system protein-gRNA complexes. In any of the embodiments disclosed herein, the nucleic acids are selected from the group consisting of single stranded DNA, single stranded RNA, double stranded DNA, double stranded RNA, DNA/RNA hybrids, cDNA, synthetic DNA, and artificial DNA. In any of the embodiments disclosed herein, the nucleic acids are double stranded DNA. In any of the embodiments disclosed herein, the nucleic acids are DNA, and wherein the contacting of step (b) generates host-DNA adapter ligated on the 5' end but not the 3' end and non-host DNA adapter ligated on both the 5' and 3' ends. In any of the embodiments disclosed herein, the nucleic acids are DNA. In any of the embodiments disclosed herein, the DNA is genomic DNA. In any of the embodiments disclosed herein, the CRISPR/Cas system protein is Cas9, Cpf1, Cas3, Cas8a-c, Cas10, Cse1, Csy1, Csn2, Cas4, Csm2, or Cm5. In any of the embodiments disclosed herein, the CRISPR/Cas system protein is Cas9. In any of the embodiments disclosed herein, the targeted sites in the host nucleic acids are followed by a Protospacer Adjacent Motif or (PAM) sequence that can be bound by Cas9. In any of the embodiments disclosed herein, the CRISPR/Cas system protein is catalytically dead, for example dCas9. In any of the embodiments disclosed herein, the CRISPR/Cas system protein is a CRISPR/Cas system protein nickase, for example Cas9 nickase. In any of the embodiments disclosed herein, the CRISPR/Cas system protein is thermostable. In any of the embodiments disclosed herein, the host is selected from the group consisting of a human, cow, horse, sheep, pig, monkey, dog, cat, gerbil, bird, mouse, and rat. In any of the embodiments disclosed herein, the non-host is a prokaryotic organism. In any of the embodiments disclosed herein, the non-host is a eukaryotic organism. In any of the embodiments disclosed herein, the non-host is a parasite. In any of the embodiments disclosed herein, the non-host is selected from the group consisting of a virus, bacterial, fungus, and protozoa. In any of the embodiments disclosed herein, the adapter-ligated host nucleic acids and non-host nucleic acids range from 50-1000 bp. In any of the embodiments disclosed herein, the non-host nucleic acids comprise less than 50% of the total nucleic acids in the sample. In any of the embodiments disclosed herein, the non-host nucleic acids comprise less than 5% of the total nucleic acids in the sample. In any of the embodiments disclosed herein, the sample is any one of a biological sample, a clinical sample, a forensic sample or an environmental sample. In any of the embodiments disclosed herein, step (c) comprises amplifying the product of step (b) using adapter-specific PCR. In any of the embodiments disclosed herein, step (c) comprises treating the product of step (b) with an enzyme that has exonuclease activity. In any of the embodiments disclosed herein, the enzyme is Exonuclease III or BAL-31. In any of the embodiments disclosed herein, step (c) comprises removing the host nucleic acids by size-exclusion. In any of the embodiments disclosed herein, step (c) comprises removing the host nucleic acids with the use of biotin. In any of the embodiments disclosed herein, the method further comprises amplifying the product of step (b) using adapter-specific PCR. In any of the embodiments disclosed herein, the method further comprises treating the product of step (b) with an enzyme that has exonuclease activity. In any of the embodiments disclosed herein, the enzyme is Exonuclease III or BAL-31. In any of the embodiments disclosed herein, the method further comprises including the use of positive control target sequences. In any of the embodiments disclosed herein, the method further comprises including the use of negative control gRNAs. In any of the embodiments disclosed herein, the sample is selected from whole blood, plasma, serum, tears, saliva, mucous, cerebrospinal fluid, teeth, bone, fingernails, feces, urine, tissue, and a biopsy.

In another aspect, provided herein is a method of depleting targeted sequences in a sample comprising:(a) providing a sample comprising sequences of interest and targeted sequences for depletion; (b) contacting the sample with a plurality of CRISPR/Cas system protein-gRNA complexes, wherein the gRNAs are complementary to the targeted sequences, thereby generating cleaved targeted sequences; and (c) contacting the product of step (b) with an enzyme that has exonuclease activity. In any of the embodiments disclosed herein, the enzyme is Exonuclease III or BAL-31. In any of the embodiments disclosed herein, the CRISPR/Cas system protein is Cas9. In any of the embodiments disclosed herein, the targeted sequences for depletion comprise sequences encoding globin proteins, sequences encoding a transposon, sequences encoding retroviral sequences, sequences comprising telomere sequences, sequences comprising sub-telomeric repeats, sequences comprising centromeric sequences, sequences comprising intron sequences, sequences comprising Alu repeats, sequences comprising SINE repeats, sequences comprising LINE repeats, sequences comprising dinucleic acid repeats, sequences comprising trinucleic acid repeats, sequences comprising tetranucleic acid repeats, sequences comprising poly-A repeats, sequences comprising poly-T repeats, sequences comprising poly-C repeats, sequences comprising poly-G repeats, sequences comprising AT-rich sequences, or sequences comprising GC-rich sequences. In any of the embodiments disclosed herein, the method comprises contacting the sample with at least $10^2$ unique CRISPR/Cas system protein-gRNA complexes. In any of the embodiments disclosed herein, the sample is selected from whole blood, plasma, serum, tears, saliva, mucous, cerebrospinal fluid, teeth, bone, fingernails, feces, urine, tissue, and a biopsy.

In another aspect, provided herein is a method of generating cleaved targeted sequences in a sample comprising:(a) providing a sample comprising sequences of interest and targeted sequences for cleavage; (b) contacting the sample with a plurality of CRISPR/Cas system protein-gRNA complexes, wherein the gRNAs are complementary to the targeted sequences, thereby generating cleaved targeted sequences; (c) dissociating the CRISPR/Cas system protein from the cleaved targeted sequences; (d) generating additional cleaved targeted sequences; and (e) recovering the uncut sequences of interest. In any of the embodiments disclosed herein, the CRISPR/Cas system protein is thermostable. In any of the embodiments disclosed herein, the thermostable CRISPR/Cas system protein is thermostable Cas9. In any of the embodiments disclosed herein, the dissociating of the CRISPR/Cas system protein from the cleaved targeted sequences is achieved by elevating the temperature of the mixture of step (b) to at least 75°. In any of the embodiments disclosed herein, the generating of additional cleaved targeted sequences is achieved by lowering the temperature of the mixture of step (b) to at least 50°. In any of the embodiments disclosed herein, step (e) comprises amplifying the product of step (d) using adapter-specific PCR. In any of the embodiments disclosed herein, step (e) comprises treating the product of step (d) with an enzyme that has exonuclease activity. In any of the embodiments disclosed herein, the enzyme is Exonuclease III or BAL-31. In any of the embodiments disclosed herein, the CRISPR/Cas system protein is Cas9. In any of the embodiments disclosed herein, the targeted sequences for cleavage comprise sequences encoding globin proteins, sequences encoding a transposon, sequences encoding retroviral sequences, sequences comprising telomere sequences, sequences comprising sub-telomeric repeats, sequences comprising centromeric sequences, sequences comprising intron sequences, sequences comprising Alu repeats, sequences comprising SINE repeats, sequences comprising LINE repeats, sequences comprising dinucleic acid repeats, sequences comprising trinucleic acid repeats, sequences comprising tetranucleic acid repeats, sequences comprising poly-A repeats, sequences comprising poly-T repeats, sequences comprising poly-C repeats, sequences comprising poly-G repeats, sequences comprising AT-rich sequences, or sequences comprising GC-rich sequences. In any of the embodiments disclosed herein, the method comprises contacting the sample with at least $10^2$ unique CRISPR/Cas system protein-gRNA complexes. In any of the embodiments disclosed herein, the sample is selected from whole blood, plasma, serum, tears, saliva, mucous, cerebrospinal fluid, teeth, bone, fingernails, feces, urine, tissue, and a biopsy.

In another aspect, provided herein is a method of depleting targeted sequences in a sample comprising:(a)providing a sample comprising sequences of interest and targeted sequences for cleavage; (b) contacting the sample with a plurality of CRISPR/Cas system protein-gRNA complexes, wherein the gRNAs are complementary to the targeted sequences, thereby generating cleaved targeted sequences, and wherein the CRISPR/Cas system protein is thermostable; (c) elevating the temperature of the mixture of step (b) to at least 75°; (d) lowering the temperature of the mixture of step (b) at least 50°; (e) repeating steps (c) and (d) at least once; and (f) recovering the uncut sequences of interest. In any of the embodiments disclosed herein, step (f) comprises amplifying the product of step (e) using adapter-specific PCR. In any of the embodiments disclosed herein, step (f) comprises treating the product of step (e) with an enzyme that has exonuclease activity. In any of the embodiments disclosed herein, the enzyme is Exonuclease III or BAL-31. In any of the embodiments disclosed herein, the CRISPR/Cas system protein is Cas9. In any of the embodiments disclosed herein, the targeted sequences for cleavage comprise sequences encoding globin proteins, sequences encoding a transposon, sequences encoding retroviral sequences, sequences comprising telomere sequences, sequences comprising sub-telomeric repeats, sequences comprising centromeric sequences, sequences comprising intron sequences, sequences comprising Alu repeats, sequences comprising SINE repeats, sequences comprising LINE repeats, sequences comprising dinucleic acid repeats, sequences comprising trinucleic acid repeats, sequences comprising tetranucleic acid repeats, sequences comprising poly-A repeats, sequences comprising poly-T repeats, sequences comprising poly-C repeats, sequences comprising poly-G repeats, sequences comprising AT-rich sequences, or sequences comprising GC-rich sequences. In any of the embodiments disclosed herein, the method comprises contacting the sample with at least $10^2$ unique CRISPR/Cas system protein-gRNA complexes. In any of the embodiments disclosed herein, the sample is selected from whole blood, plasma, serum, tears, saliva, mucous, cerebrospinal fluid, teeth, bone, fingernails, feces, urine, tissue, and a biopsy.

In another aspect, provided herein is a method for serially depleting targeted nucleic acids in a sample comprising:(a) providing a sample comprising host nucleic acids and non-host nucleic acids, wherein the non-host nucleic acids comprise nucleic acids from at least one known non-host organism and nucleic acids from at least one unknown non-host organism; (b) contacting the sample with a plurality of CRISPR/Cas system protein-gRNA complexes, wherein the gRNAs are configured to hybridize to targeted sequences in the host nucleic acids, whereby a portion of the host nucleic acids are cleaved; (c) contacting the sample with a plurality of CRISPR/Cas system protein-gRNA complexes, wherein the gRNAs are configured to hybridize to targeted sequences in the at least one known non-host nucleic acids, whereby a portion of the at least one known non-host nucleic acids are cleaved; and (d) isolating the nucleic acids from the unknown non-host organism. In any of the embodiments disclosed herein, the method comprises contacting the sample with at least $10^2$ unique CRISPR/Cas system protein-gRNA complexes configured to hybridize to targeted sequences in the host nucleic acids. In any of the embodiments disclosed herein, the method comprises contacting the sample with at least $10^2$ unique CRISPR/Cas system protein-gRNA complexes configured to hybridize to targeted sequences in the at least one known non-host nucleic acids. In any of the embodiments disclosed herein, the sample is selected from whole blood, plasma, serum, tears, saliva, mucous, cerebrospinal fluid, teeth, bone, fingernails, feces, urine, tissue, and a biopsy. In any of the embodiments disclosed herein, the nucleic acids from an unknown non-host organism comprise less than 5% of the total nucleic acids in the sample. In any of the embodiments disclosed herein, the host is a human. In any of the embodiments disclosed herein, the at least one known non-host organism is a species of *Streptococcus*.

In another aspect, provided herein is a method for analyzing genomic DNA, comprising:(a) treating DNA isolated from a population of cells from a sample with an insertional enzyme to produce a plurality of tagged fragments of non-mitochondrial genomic DNA, whereby also generating a residual amount of tagged mitochondrial DNA; (b) enriching the product of step (a) for non-mitochondrial DNA according to any of the relevant methods provided herein. For example, such a method of enriching a sample can comprise: (a) providing a sample comprising mitochondrial DNA and non-mitochondrial DNA, wherein the mitochondrial DNA and non-mitochondrial DNA are adapter-ligated, and wherein the adapters are ligated to the 5' and 3' ends of the mitochondrial DNA and non-mitochondrial DNA; (b) contacting the sample with a plurality of CRISPR/Cas system protein-gRNA complexes, wherein the gRNAs are complementary to the mitochondrial DNA, thereby generating mitochondrial DNA adapter ligated only on one end and non-mitochondrial DNA adapter ligated on both the 5' and 3' ends; and (c) enriching the sample for non-mitochondrial DNA. In any of the embodiments disclosed herein, the method further comprises (a) sequencing at least some of the tagged fragments to produce a plurality of sequence reads; and (b) making an epigenetic map of a region of the genome of said cells by mapping information obtained from the sequence reads to the region. In any of the embodiments disclosed herein, the sample is selected from whole blood, plasma, serum, tears, saliva, mucous, cerebrospinal fluid, teeth, bone, fingernails, feces, urine, tissue, and a biopsy.

In another aspect, provided herein is a composition comprising a mixture of DNA from a first genome and DNA from a second genome, wherein the first genome DNA and the second genome DNA are adapter-ligated, and wherein the first genome DNA is complexed to a gRNA-CRISPR/Cas system protein complex. In any of the embodiments disclosed herein, the first genome is from a host organism and the second genome is from a non-host organism. In any of the embodiments disclosed herein, the CRISPR/Cas system protein is Cas9. In any of the embodiments disclosed herein, the CRISPR/Cas system protein is thermostable.

In another aspect, provided herein are kits. In another aspect, provided herein is a kit comprising: (a) CRISPR/Cas system protein; and (b) gRNAs, wherein the gRNAs are complementary to mitochondrial DNA. In another aspect, provided herein is a kit comprising (a) a CRISPR/Cas system protein; (b) gRNAs, wherein the gRNAs are complementary to a target of interest; and (c) an enzyme having exonuclease activity. In another aspect, provided herein is a kit comprising (a) a CRISPR/Cas system protein, wherein the CRISPR/Cas system protein is thermostable; and (b) gRNAs, wherein the gRNAs are complementary to a target of interest. In another aspect, provided herein is a kit comprising (a) a CRISPR/Cas system protein; and (b) a first set of gRNAs, wherein the gRNAs are complementary to target sequences of interest; and (c) a control set of reagents. In another aspect, provided herein is a kit comprising: (a) reagents for isolating DNA from a population of cells; (b) an insertional enzyme; (c) a CRISPR/Cas system protein; and (d) a plurality of gRNAs, wherein the gRNAs are complementary to mitochondrial DNA. In any of the kits disclosed herein, the kit further comprises a collection of Y-shaped adapters or poly-G adapters. In any of the kits disclosed herein, the CRISPR/Cas system protein is Cas9. In any of the kits disclosed herein, the kits further comprise a positive control set of reagents, for example the positive control set of reagents comprise a collection of nucleic acid fragments, wherein the fragments comprise the target sequences of interest, to which the gRNAs are at least 85% complementary. In any of the kits disclosed herein, the kits further comprise a negative control set of reagents, for example, the negative control set of reagents comprise a second set of gRNAs, wherein the second set of gRNAs exhibit reduced binding to the target sequences of interest, as compared to the first set of gRNAs; or for example the negative control set of reagents can comprise a collection of nucleic acid fragments, wherein the fragments are no more than 90% complementary to the first set of gRNAs. In any one of the kits disclosed herein, the kit further comprises at least $10^2$ unique gRNAs.

In another aspect the invention provides a method of depleting targeted sequences in a sample comprising: providing a sample comprising sequences of interest and targeted sequences for depletion; and contacting the sample with a plurality of CRISPR/Cas system protein-gRNA complexes, wherein the gRNAs are complementary to the targeted sequences, thereby generating cleaved targeted sequences. In a related aspect, the invention provides a method for one of depletion and partitioning of targeted sequences in a sample comprising: providing nucleic acids extracted from a sample, wherein the extracted nucleic acid sequences comprise sequences of interest and targeted sequences for one of depletion and partitioning; providing a plurality of guide RNAs (gRNA)-CRISPR/Cas system protein complexes, wherein the gRNAs are configured to hybridize to different targeted sequences; mixing the nucleic acids with the gRNA-CRISPR/Cas system protein complexes, wherein at least a portion of the plurality of gRNA-CRISPR/Cas system protein complexes hybridizes to the targeted sequences. In any one of the embodiments disclosed herein, the method further comprises extracting the nucleic acid sequences from the sample. In any one of the embodiments disclosed herein the CRISPR/Cas system protein is Cas9. In any one of the embodiments disclosed herein, the method further comprises fragmenting the extracted nucleic acids. In any one of the embodiments disclosed herein, the method further comprises adapter ligating the 5' and 3' ends of the fragmented extracted nucleic acids. In any one of the embodiments disclosed herein, the method further comprises incubating the mixture to cleave the targeted sequences. In any one of the embodiments disclosed herein, each sequence targeted for depletion is followed by a Protospacer Adjacent Motif or (PAM) sequence that can be bound by a Cas9 protein derived from a bacterial species but wherein the sequences of interest (for enrichment) are not targeted by the gRNAs. In any one of the embodiments disclosed herein, the Cas9 protein comprises a catalytically dead Cas9 that includes an affinity tag previously attached thereto, further comprising partitioning the mixture into a first portion that includes the complementary target specific nucleic sequence present in the mixture that include a guide RNA/Cas9 complex and a second portion that includes fragmented extracted nucleic acid sequences that are not bound by a guide RNA/Cas9 complex, wherein the partitioning is performed using the affinity tag. In any one of the embodiments disclosed herein, the cleaved extracted nucleic acid sequences are smaller than the fragmented extracted nucleic acid sequences that have not been cleaved, the method further comprising, removing the cleaved extracted nucleic acid sequences from the mixture by size selective exclusion. In any one of the embodiments disclosed herein, the method further comprises amplifying the fragmented extracted nucleic acid sequences that have not been cleaved. In any one of the embodiments disclosed herein, the method further comprises analyzing each of the first and second portions by amplification and sequencing. In any one of the embodiments disclosed herein, the sample is any one of a biological sample, a clinical sample, a forensic sample or an environmental sample. In any one of the embodiments disclosed herein, the extracted nucleic acids comprise host nucleic acid sequences and non-host nucleic acid sequences. In any one of the embodiments disclosed herein, the non-host nucleic acid sequences comprise microbial nucleic acid sequences. In any one of the embodiments disclosed herein, the microbial nucleic acid sequences include any one of bacterial, viral and eukaryotic parasitic nucleic acid sequences. In any one of the embodiments disclosed herein, at least a portion of the host nucleic acid sequences are included in the sequences being targeted for one of depletion and partitioning. In any one of the embodiments disclosed herein, substantially all of the host nucleic acid sequences are included in the sequences being targeted for one of depletion and partitioning. In any one of the embodiments disclosed herein, the extracted nucleic acids comprise a plurality of different ribosomal RNA sequences and the plurality of different target specific gRNAs comprise at least a portion of the target nucleic acid sequences configured to hybridize to a portion of the plurality of different ribosomal RNA sequences. In any one of the embodiments disclosed herein, the extracted nucleic acid sequences comprise a plurality of different mitochondrial nucleic acid sequences and the plurality of different target specific gRNAs comprise one or more target nucleic acid sequence configured to hybridize to a portion of the plurality of different mitochondrial nucleic acid sequences. In any one of the embodiments disclosed herein, the extracted nucleic acid sequences comprise a plurality of different repetitive nucleic acid sequences in the nucleic acid sequences being targeted for depletion and the plurality of different target specific gRNAs comprise at least one target nucleic acid sequence that can hybridize to a portion of the plurality of different repetitive nucleic acid sequences. In any one of the embodiments disclosed herein, the extracted nucleic acids incudes any one of single stranded DNA, double stranded DNA, single stranded RNA, double stranded RNA, cDNA, synthetic DNA, artificial DNA, and DNA/RNA hybrids. In any one of the embodiments disclosed herein, the sequences of interest comprise less than 50% of the extracted nucleic acids. In any one of the embodiments disclosed herein, the sequences of interest comprise less than 5% of the extracted nucleic acids.

In another aspect the invention provides a guide RNA library comprising a plurality of target-specific guide RNAs, each configured to hybridize to a selected target nucleic acid sequence, wherein each guide RNA comprises a sequence that can be bound by a Cas9 protein. In any one of the embodiments disclosed herein, each selected target nucleic acid sequence is immediately followed by a protospacer adjacent motif. In any one of the embodiments disclosed herein, target specific gRNAs include gRNAs suitable for hybridizing with selected target nucleic acid sequences in the human genome. In any one of the embodiments disclosed herein, the human genome includes nucleic acid sequences comprising a plurality of different repetitive nucleic acid sequences and the target-specific gRNAs includes guide elements suitable for hybridizing with each of the plurality of different repetitive nucleic acid sequences.

In another aspect, the technology disclosed herein relates to methods and systems for selective or targeted depletion and/or selective or targeted partitioning of nucleic acid samples using a Cas9-enzyme-mediated method.

In another aspect, the technology disclosed herein relates to forming a library of gRNAs wherein each gRNA is suitable to hybridize to a nucleic acid sequence being targeted for removal from the overall nucleic acid sample wherein the sequence being targeted is followed by a Protospacer Adjacent Motif (PAM) sequence. By mixing the gRNAs with nucleic acid samples and a Cas9 protein derived from a bacterial species the gRNAs hybridize to the nucleic acid sequence being targeted for removal and the Cas9 enzyme forms a guide RNA/Cas9 complex that bonds to the nucleic acid sequence being targeted for removal. Thereafter the guide RNA/Cas9 complex can be incubated to cut the targeted nucleic acid sequences so that cut sequences can be separated from uncut nucleic acid sequences or so that targeted sequences that are bonded by a guide RNA/Cas9 complex can be partitioned from DNA sequences that are not bonded to by a guide RNA/Cas9 complex.

In another aspect, the technology disclosed herein is also useful for depleting host molecules from nucleic acid samples that contain low levels (e.g. <50%) of non-host nucleic acids.

In another aspect, the technology disclosed herein comprises: 1) combining a genomic DNA sample or sequencing library with a mixture of Cas9-gRNA complexes, wherein the Cas9-gRNA complexes comprise a Cas9 protein and Cas9-associated gRNAs that are complementary to a pre-defined site in the genome; and b) incubating the reaction mixture to cut only the target regions. In the embodiment in which a sequencing library is targeted, Cas9 cutting would separate the two sequencing adapters and hence make these fragments unable to be amplified. In the embodiment in which genomic DNA is targeted, Cas9 cutting would make these fragments small enough to be removed by size selection.

BRIEF DESCRIPTION OF THE DRAWINGS

FIG. 11 illustrates using a thermostable Cas9 to increase the efficiency of Cas9-mediated depletion.

DETAILED DESCRIPTION OF THE INVENTION

Definitions

Figure 1:
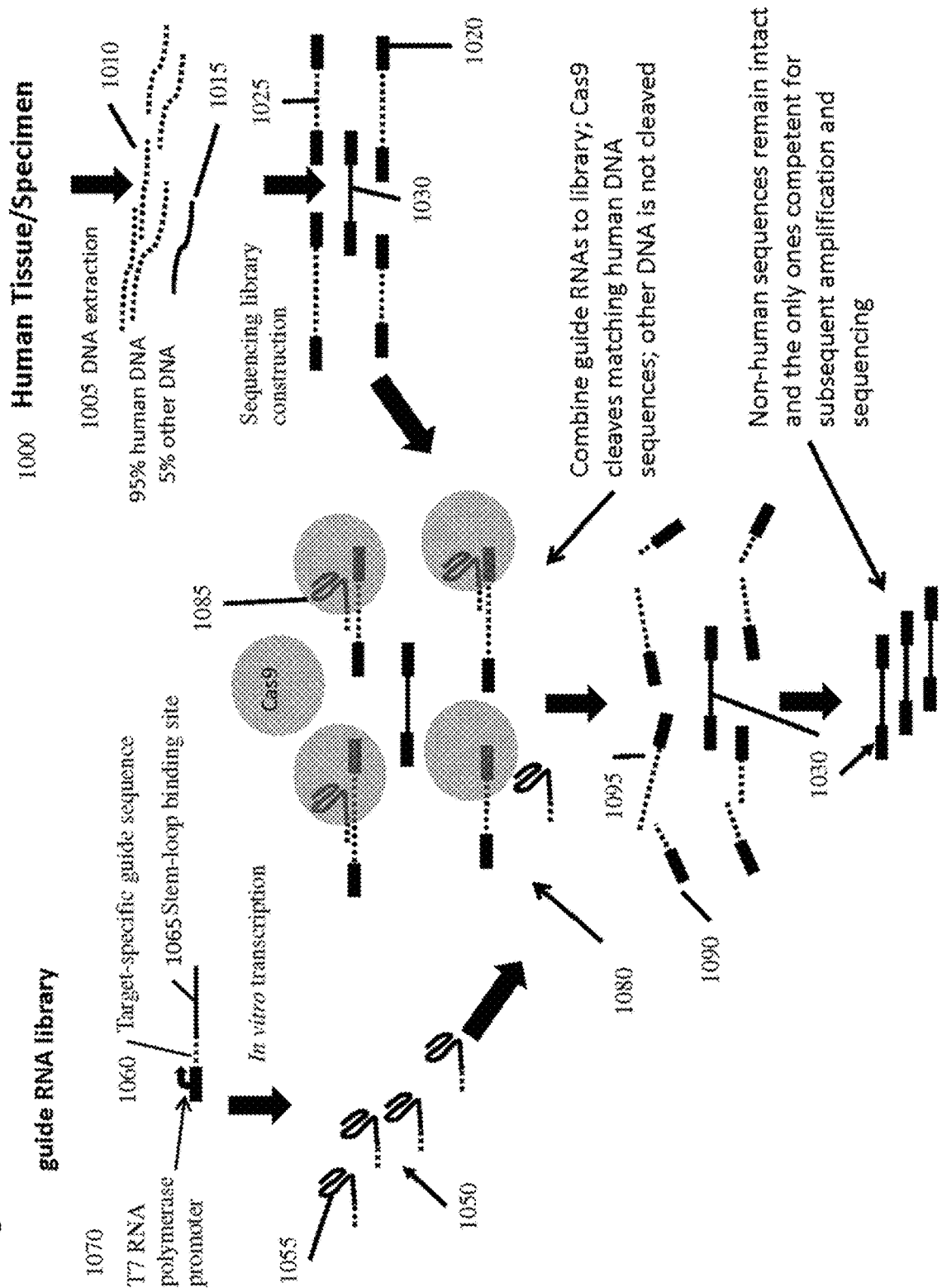
FIG. 1 illustrates a general schematic of the depletion method using Cas9 to selectively cleave target sequences in a library.

Unless defined otherwise herein, all technical and scientific terms used herein have the same meaning as commonly understood by one of ordinary skill in the art to which this invention belongs. Although any methods and materials similar or equivalent to those described herein can be used in the practice or testing of the present invention, the preferred methods and materials are described.

The headings provided herein are not limitations of the various aspects or embodiments of the invention. Accordingly, the terms defined immediately below are more fully defined by reference to the specification as a whole.

Unless defined otherwise, all technical and scientific terms used herein have the same meaning as commonly understood by one of ordinary skill in the art to which this invention belongs. Singleton, et al., DICTIONARY OF MICROBIOLOGY AND MOLECULAR BIOLOGY, 2D ED., John Wiley and Sons, New York (1994), and Hale & Markham, THE HARPER COLLINS DICTIONARY OF BIOLOGY, Harper Perennial, N.Y. (1991) provide one of skill with the general meaning of many of the terms used herein. Still, certain terms are defined below for the sake of clarity and ease of reference.

Numeric ranges are inclusive of the numbers defining the range.

The term "sample" as used herein relates to a material or mixture of materials, typically, although not necessarily, in liquid form, containing one or more analytes of interest.

The term "nucleic acid sample," as used herein denotes a sample containing nucleic acids. Nucleic acid samples used herein may be complex in that they contain multiple different molecules that contain sequences. Genomic DNA from a mammal (e.g., mouse or human) are types of complex samples. Complex samples may have more then $10^4$, $10^5$, $10^6$ or $10^7$ different nucleic acid molecules. A DNA target may originate from any source such as genomic DNA, cDNA, or an artificial DNA construct. Any sample containing nucleic acid, e.g., genomic DNA made from tissue culture cells or a sample of tissue may be employed herein.

The term "nucleotide" is intended to include those moieties that contain not only the known purine and pyrimidine bases, but also other heterocyclic bases that have been modified. Such modifications include methylated purines or pyrimidines, acylated purines or pyrimidines, alkylated riboses or other heterocycles. In addition, the term "nucleotide" includes those moieties that contain hapten or fluorescent labels and may contain not only conventional ribose and deoxyribose sugars, but other sugars as well. Modified nucleosides or nucleotides also include modifications on the sugar moiety, e.g., wherein one or more of the hydroxyl groups are replaced with halogen atoms or aliphatic groups, or are functionalized as ethers, amines, or the like.

The term "nucleic acids" and "polynucleotides" are used interchangeably herein. Polynucleotide is used to describe a nucleic acid polymer of any length, e.g., greater than about 2 bases, greater than about 10 bases, greater than about 100 bases, greater than about 500 bases, greater than 1000 bases, up to about 10,000 or more bases composed of nucleotides, e.g., deoxyribonucleotides or ribonucleotides, and may be produced enzymatically or synthetically (e.g., PNA as described in U.S. Pat. No. 5,948,902 and the references cited therein) which can hybridize with naturally occurring nucleic acids in a sequence specific manner analogous to that of two naturally occurring nucleic acids, e.g., can participate in Watson-Crick base pairing interactions. Naturally-occurring nucleotides include guanine, cytosine, adenine and thymine (G, C, A and T, respectively). DNA and RNA have a deoxyribose and ribose sugar backbone, respectively, whereas PNA's backbone is composed of repeating N-(2-aminoethyl)-glycine units linked by peptide bonds. In PNA various purine and pyrimidine bases are linked to the backbone by methylene carbonyl bonds. A locked nucleic acid (LNA), often referred to as inaccessible RNA, is a modified RNA nucleotide. The ribose moiety of an LNA nucleotide is modified with an extra bridge connecting the 2' oxygen and 4' carbon. The bridge "locks" the ribose in the 3'-endo (North) conformation, which is often found in the A-form duplexes. LNA nucleotides can be mixed with DNA or RNA residues in the oligonucleotide whenever desired. The term "unstructured nucleic acid," or "UNA," is a nucleic acid containing non-natural nucleotides that bind to each other with reduced stability. For example, an unstructured nucleic acid may contain a G' residue and a C' residue, where these residues correspond to non-naturally occurring forms, i.e., analogs, of G and C that base pair with each other with reduced stability, but retain an ability to base pair with naturally occurring C and G residues, respectively. Unstructured nucleic acid is described in US20050233340, which is incorporated by reference herein for disclosure of UNA.

The term "oligonucleotide" as used herein denotes a single-stranded multimer of nucleotides.

Unless otherwise indicated, nucleic acids are written left to right in 5' to 3' orientation; amino acid sequences are written left to right in amino to carboxy orientation, respectively.

The term "cleaving," as used herein, refers to a reaction that breaks the phosphodiester bonds between two adjacent nucleotides in both strands of a double-stranded DNA molecule, thereby resulting in a double-stranded break in the DNA molecule.

The term "cleavage site, as used herein, refers to the site at which a double-stranded DNA molecule has been cleaved.

The term "hybridization" refers to the process by which a strand of nucleic acid joins with a complementary strand through base pairing as known in the art. A nucleic acid is considered to be "selectively hybridizable" to a reference nucleic acid sequence if the two sequences specifically hybridize to one another under moderate to high stringency hybridization and wash conditions. Moderate and high stringency hybridization conditions are known (see, e.g., Ausubel, et al., Short Protocols in Molecular Biology, 3rd ed., Wiley & Sons 1995 and Sambrook et al., Molecular Cloning: A Laboratory Manual, Third Edition, 2001 Cold Spring Harbor, N.Y.). One example of high stringency conditions includes hybridization at about 42° C. in 50% formamide, 5×SSC, 5×Denhardt's solution, 0.5% SDS and 100 µg/ml denatured carrier DNA followed by washing two times in 2×SSC and 0.5% SDS at room temperature and two additional times in 0.1×SSC and 0.5% SDS at 42° C.

The term "duplex," or "duplexed," as used herein, describes two complementary polynucleotides that are base-paired, i.e., hybridized together.

The term "amplifying" as used herein refers to generating one or more copies of a target nucleic acid, using the target nucleic acid as a template.

The term "depleting," with respect to a genome, refers to the removal of one part of the genome from the remainder of the genome to produce a product that is isolated from the remainder of the genome. The term "depleting" also encompasses removal of DNA from one species while retaining DNA from another species.

The term "genomic region," as used herein, refers to a region of a genome, e.g., an animal or plant genome such as the genome of a human, monkey, rat, fish or insect or plant. In certain cases, an oligonucleotide used in the method described herein may be designed using a reference genomic region, i.e., a genomic region of known nucleotide sequence, e.g., a chromosomal region whose sequence is deposited at NCBI's Genbank database or other databases, for example.

The term "genomic sequence," as used herein, refers to a sequence that occurs in a genome. Because RNAs are transcribed from a genome, this term encompasses sequence that exist in the nuclear genome of an organism, as well as sequences that are present in a cDNA copy of an RNA (e.g., an mRNA) transcribed from such a genome.

The term "genomic fragment," as used herein, refers to a region of a genome, e.g., an animal or plant genome such as the genome of a human, monkey, rat, fish or insect or plant. A genomic fragment may be an entire chromosome, or a fragment of a chromosome. A genomic fragment may be adapter ligated (in which case it has an adapter ligated to one or both ends of the fragment, or to at least the 5' end of a molecule), or may not be adapter ligated.

In certain cases, an oligonucleotide used in the method described herein may be designed using a reference genomic region, i.e., a genomic region of known nucleotide sequence, e.g., a chromosomal region whose sequence is deposited at NCBI's Genbank database or other databases, for example. Such an oligonucleotide may be employed in an assay that uses a sample containing a test genome, where the test genome contains a binding site for the oligonucleotide.

The term "ligating," as used herein, refers to the enzymatically catalyzed joining of the terminal nucleotide at the 5' end of a first DNA molecule to the terminal nucleotide at the 3' end of a second DNA molecule.

If two nucleic acids are "complementary," each base of one of the nucleic acids base pairs with corresponding nucleotides in the other nucleic acid. The term "complementary" and "perfectly complementary" are used synonymously herein.

The term "separating," as used herein, refers to physical separation of two elements (e.g., by size or affinity, etc.) as well as degradation of one element, leaving the other intact.

In a cell, DNA usually exists in a double-stranded form, and as such, has two complementary strands of nucleic acid referred to herein as the "top" and "bottom" strands. In certain cases, complementary strands of a chromosomal region may be referred to as "plus" and "minus" strands, the "first" and "second" strands, the "coding" and "noncoding" strands, the "Watson" and "Crick" strands or the "sense" and "antisense" strands. The assignment of a strand as being a top or bottom strand is arbitrary and does not imply any particular orientation, function or structure. Until they become covalently linked, the first and second strands are distinct molecules. For ease of description, the "top" and "bottom" strands of a double-stranded nucleic acid in which the top and bottom strands have been covalently linked will still be described as the "top" and "bottom" strands. In other words, for the purposes of this disclosure, the top and bottom strands of a double-stranded DNA do not need to be separated molecules. The nucleotide sequences of the first strand of several exemplary mammalian chromosomal regions (e.g., BACs, assemblies, chromosomes, etc.) is known, and may be found in NCBI's Genbank database, for example.

The term "top strand," as used herein, refers to either strand of a nucleic acid but not both strands of a nucleic acid. When an oligonucleotide or a primer binds or anneals "only to a top strand," it binds to only one strand but not the other. The term "bottom strand," as used herein, refers to the strand that is complementary to the "top strand." When an oligonucleotide binds or anneals "only to one strand," it binds to only one strand, e.g., the first or second strand, but not the other strand. If an oligonucleotide binds or anneals to both strands of a double-stranded DNA, the oligonucleotide may have two regions, a first region that hybridizes with the top strand of the double-stranded DNA, and a second region that hybridizes with the bottom strand of the double-stranded DNA.

The term "double-stranded DNA molecule" refers to both double-stranded DNA molecules in which the top and bottom strands are not covalently linked, as well as double-stranded DNA molecules in which the top and bottom stands are covalently linked. The top and bottom strands of a double-stranded DNA are base paired with one other by Watson-Crick interactions.

The term "denaturing," as used herein, refers to the separation of at least a portion of the base pairs of a nucleic acid duplex by placing the duplex in suitable denaturing conditions. Denaturing conditions are well known in the art. In one embodiment, in order to denature a nucleic acid duplex, the duplex may be exposed to a temperature that is above the Tm of the duplex, thereby releasing one strand of the duplex from the other. In certain embodiments, a nucleic acid may be denatured by exposing it to a temperature of at least 90° C. for a suitable amount of time (e.g., at least 30 seconds, up to 30 mins). In certain embodiments, fully denaturing conditions may be used to completely separate the base pairs of the duplex. In other embodiments, partially denaturing conditions (e.g., with a lower temperature than fully denaturing conditions) may be used to separate the base pairs of certain parts of the duplex (e.g., regions enriched for A-T base pairs may separate while regions enriched for G-C base pairs may remain paired). Nucleic acid may also be denatured chemically (e.g., using urea or NaOH).

The term "genotyping," as used herein, refers to any type of analysis of a nucleic acid sequence, and includes sequencing, polymorphism (SNP) analysis, and analysis to identify rearrangements.

The term "sequencing," as used herein, refers to a method by which the identity of consecutive nucleotides of a polynucleotide are obtained.

The term "next-generation sequencing" refers to the so-called parallelized sequencing-by-synthesis or sequencing-by-ligation platforms, for example, those currently employed by Illumina, Life Technologies, and Roche, etc. Next-generation sequencing methods may also include nanopore sequencing methods or electronic-detection based methods such as Ion Torrent technology commercialized by Life Technologies.

The term "host nucleic acids" refers to nucleic acids that originate from the multicellular eukaryotic subject from which the sample was obtained. Host nucleic acids can be, e.g., plant or animal, including mammals particularly humans. The term "host nucleic acids" includes nuclear nucleic acids as well as nucleic acids present in other organelles, e.g., the mitochondria and chloroplast (if the host is a plant), but not the nucleic acids from microbes that often grow on or in the subject.

The term "non-host nucleic acids" refers to nucleic acids not belonging to the host from which the sample was obtained. Non-host nucleic acids can be viral, bacterial, or other microbial DNA.

The term "microbial nucleic acids" refers to nucleic acids that is microbial (e.g., bacterial or viral or from a eukaryotic parasite) in origin that is present in a sample.

The term "host DNA" refers to DNA that originates from the multicellular eukaryotic subject from which the sample was obtained. Host DNA can be, e.g., plant or animal, including mammals particularly humans. The term "host DNA" includes nuclear DNA as well as DNA present in other organelles, e.g., the mitochondria and chloroplast (if the host is a plant), but not the DNA from microbes that often grow on or in the subject.

The term "non-host DNA" refers to DNA not belonging to the host from which the sample was obtained. Non-host DNA can be viral, bacterial, or other microbial DNA.

The term "microbial DNA" refers to genomic DNA that is microbial (e.g., bacterial or viral or from a eukaryotic parasite) in origin that is present in a sample.

The term "complementary DNA" or cDNA refers to a double-stranded DNA sample that was produced from an RNA sample by reverse transcription of RNA (using primers such as random hexamers or oligo-dT primers) followed by second-strand synthesis by digestion of the RNA with RNaseH and synthesis by DNA polymerase.

The term "RNA promoter adapter" is an adapter that contains a promoter for a bacteriophage RNA polymerase, e.g., the RNA polymerase from bacteriophage T3, T7, SP6 or the like.

The term "metagenomics sample" refers to a sample that contains more than one species of organism (eukaryotic, prokaryotic, or viral organisms).

The term "metagenomics analysis" refers to the analysis of a metagenomics sample.

Other definitions of terms may appear throughout the specification.

Objects of the Invention

In view of the problems associated with conventional methods and apparatus set forth above it is an object of the present invention to deplete selected nucleic acids from a nucleic acid sample using an enzyme mediated cutting mechanism.

It is another object of the present invention to provide a method that depletes selected host nucleic acids from sequencing libraries that include host and non-host nucleic acids in order to increase the proportion of non-host nucleic acid fragments for the purposes of pursuing downstream applications, including, but not limited to amplification, sequencing, cloning, etc.

It is another object of the present invention to provide a metagenomic analysis method that is unbiased relative to the fragments from across the genome of a particular species by selectively depleting some or all of the particular species' genome from a metagenomics sample.

It is further object of the present invention to gain better resolution in metagenomic analysis by increasing the number of sample reads that map to the a species' metagenome without increasing and in some instances while decreasing the amount of sequencing.

It is a further object of the present invention to provide methods and compositions to deplete mitochondrial DNA from a sample comprising mitochondrial DNA and non-mitochondrial DNA.

Nucleic Acids, Samples

Nucleic acids of the invention (targeted for enrichment, partitioning, or depletion) can be single stranded DNA, single stranded RNA, double stranded DNA, double stranded RNA, artificial DNA, artificial RNA, synthetic DNA, synthetic RNA, and RNA/DNA hybrids.

The nucleic acids of the invention can be a genomic fragment, comprising a region of the genome, or the whole genome itself. In one embodiment, the genome is a DNA genome. In another embodiment, the genome is a RNA genome.

Nucleic acids of the invention can be obtained from a eukaryotic or prokaryotic organism; from a mammalian organism or a non-mammalian organism; from an animal or a plant; from a bacteria or virus; from an animal parasite; or from a pathogen.

Nucleic acids of the invention can be obtained from any mammalian organism. In one embodiment the mammal is a human. In another embodiment the mammal is a livestock animal, for example a horse, a sheep, a cow, a pig, or a donkey. In another embodiment, a mammalian organism is a domestic pet, for example a cat, a dog, a gerbil, a mouse, a rat. In another embodiment the mammal is a type of a monkey.

Nucleic acids of the invention can be obtained from any bird or avian organism. An avian organism includes, but is not limited to, a chicken, turkey, duck and goose.

Nucleic acids of the invention can be obtained from a plant. In one embodiment, the plant is rice, maize, wheat, rose, grape, coffee, fruit, tomato, potato, or cotton.

In some embodiments, nucleic acids of the invention are obtained from a species of bacteria. In one embodiment, the bacteria are tuberculosis-causing bacteria.

In some embodiments, nucleic acids of the invention are obtained from a virus.

In some embodiments, nucleic acids of the invention are obtained from a species of fungi.

In some embodiments, nucleic acids of the invention are obtained from a species of algae.

In some embodiments, nucleic acids of the invention are obtained from any mammalian parasite.

In some embodiments, nucleic acids of the invention are obtained from any mammalian parasite. In one embodiment, the parasite is a worm. In another embodiment, the parasite is a malaria-causing parasite. In another embodiment, the parasite is a Leishmaniasis-causing parasite. In another embodiment, the parasite is an amoeba.

In one embodiment, the nucleic acids of the invention include nucleic acids that are targets of gRNAs (also referred to interchangeably herein as gRNA elements) and nucleic acids that are not the targets of the gRNAs, in the same sample.

In one embodiment, the nucleic acids in a sample include target nucleic acids/targeted sequences (targets of gRNAs) and nucleic acids of interest/sequences of interest (not targeted by gRNAs).

In one embodiment, the nucleic acids all belong to the same organism, but a subset is targeted for depletion or partitioning. For example nucleic acids of little informative value may be targeted. Examples of nucleic acids of little informative value include, but are not limited to: mitochondrial DNA, mitochondrial RNA, mitochondrial rRNA, repetitive sequence, multi-copy sequence, sequence encoding globin proteins, sequence encoding a transposon, sequence encoding retroviral sequence, sequence comprising telomere sequence, sequence comprising sub-telomeric repeats, sequence comprising centromeric sequence, sequence comprising intron sequence, sequence comprising Alu repeats, SINE repeats, LINE repeats, dinucleic acid repeats, trinucleic acid repeats, tetranucleic acid repeats, poly-A repeats, poly-T repeats, poly-C repeats, poly-G repeats, AT-rich sequence, or GC-rich sequence.

In one embodiment, a sample is contacted with CRISPR/Cas system protein-gRNA complexes, wherein the gRNAs are complementary to target sequences for depletion, the target sequences encoding globin proteins, sequences encoding a transposon, sequences encoding retroviral sequences, sequences comprising telomere sequences, sequences comprising sub-telomeric repeats, sequences comprising centromeric sequences, sequences comprising intron sequences, sequences comprising Alu repeats, sequences comprising SINE repeats, sequences comprising LINE repeats, sequences comprising dinucleic acid repeats, sequences comprising trinucleic acid repeats, sequences comprising tetranucleic acid repeats, sequences comprising poly-A repeats, sequences comprising poly-T repeats, sequences comprising poly-C repeats, sequences comprising poly-G repeats, sequences comprising AT-rich sequences, or sequences comprising GC-rich sequences.

In one exemplary embodiment, ribosomal RNA may be targeted for depletion or partitioning. In another exemplary embodiment repetitive DNA may be targeted for depletion or partitioning. In such an embodiment, the present method is usable to deplete the ribosomal or repetitive DNA or any other DNA that has little informative value in order to reduce the cost of sequencing these elements of the DNA extraction and improve data yield.

In one embodiment, the target DNA may be non-mitochondrial DNA (e.g. genomic DNA), and the DNA of interest may be the mitochondrial DNA, and the mitochondrial DNA is enriched by targeting and depleting the non-mitochondrial human DNA.

In one embodiment, the target DNA for depletion may be mitochondrial DNA, and the DNA of interest may be the non-mitochondrial DNA, and the non-mitochondrial DNA is enriched by targeting and depleting the mitochondrial human DNA. In an exemplary embodiment, an ATAC-Seq procedure (for example see WO2014/189957 is carried out resulting in unwanted residual mitochondrial DNA; the methods of the invention can be used to deplete unwanted mitochondrial DNA from the sample.

In one embodiment, the nucleic acids to be depleted or partitioned out may be a non-mappable region of a genome; and the nucleic acids to be retained for further analysis/sequencing/cloning may be mappable regions of a genome. In one embodiment, the nucleic acids to be depleted or partitioned out may be a mappable region of a genome; and the nucleic acids to be retained for further analysis/sequencing/cloning may be non-mappable regions of a genome. Examples of non mappable regions include telomeres, centromeres, repetitive regions, or other genomic regions that contain features harder to map.

In some embodiments, the methods of the invention are carried out on samples comprising host nucleic acids and non-host nucleic acids. In one embodiment, the host nucleic acids are mammalian, and the non-host nucleic acids are not mammalian (e.g., bacterial, viral, fungal, protozoan). In one embodiment, the host nucleic acids are human and the non-host nucleic acids are bacterial. In one embodiment, the host nucleic acids are human and the non-host nucleic acids are viral. In one embodiment, the host nucleic acids are human and the non-host nucleic acids are fungal. In one embodiment, the host nucleic acids are human and the non-host nucleic acids are protozoan. In one embodiment, the host nucleic acids are from a type of livestock. In one embodiment, the host nucleic acids are from a monkey. In one specific embodiment, the host nucleic acids are human and the non-host nucleic acids are from an unidentified pathogen, for example a known or unknown virus, or a known or unknown bacteria, or a known or unknown animal parasite. In one specific embodiment, the host nucleic acids are from a cow and the non-host nucleic acids are viral, bacterial, fungal, or protozoan.

In samples that contain both host and non-host nucleic acids, the host and non-host may have, for example, a host-pathogen relationship or a symbiotic relationship. In some embodiments, the non-host fraction of a total nucleic acid sample is obtained from a host may be derived from the microbiome that is associated with the host.

In one embodiment, a sample obtained from a host organism (e.g. a human host) contains nucleic acids from more than one non-host organism, e.g. from a plurality of non-host organisms comprising at least one unknown non-host organism to be identified. The compositions and methods of the invention can be utilized to serially process the nucleic acids in the sample to first deplete/partition out the host-DNA, and then subsequently deplete/partition out other known non-host nucleic acids that are not of interest, to arrive at a remaining pool of nucleic acids that represent a particular non-host of interest. For example, such an embodiment would be applicable in a situation where it a host would be expected to be harboring more than one known bacteria, for example existing symbiotically. For example, such an embodiment would be applicable to detect an unknown pathogen in a saliva sample from an individual, the saliva being known to harbor several species of bacteria, for example species of *Streptococcus*. In another example, the sample may be a fecal sample from a mammalian host, comprising known and unknown non-host nucleic acids.

In one embodiment, a sample obtained from a known host organism (e.g., a human host) contains non-host nucleic acids but the non-host is not known (e.g. an unknown pathogenic bacteria, virus, or other pathogen in the human blood) until the host nucleic acids are depleted or partitioned, such that the non-host nucleic acids are enriched and be subjected to further downstream analysis.

In an exemplary embodiment, where the DNA includes host-DNA and non-host DNA the present method is usable to deplete substantially all of the host DNA in order to build a library of non-host DNA for further analysis. In cases where the DNA includes nucleic and mitochondrial DNA the present method is usable to deplete the mitochondrial DNA in order to build a library of nuclear DNA for further analysis; or to deplete the nuclear DNA in order to build a library of mitochondrial DNA for further analysis. In cases where the DNA includes abundant sequences of ribosomal RNA or repetitive DNA that may have little informative value, the present method is usable to deplete the ribosomal or repetitive DNA or any other DNA that has little informative value in order to reduce the cost of sequencing these elements of the DNA extraction and improve data yield. In each application, the resulting DNA has significantly fewer DNA fragments to sequence thereby reducing sequencing cost and complexity. Moreover according to the methods of the present invention the depleted sample still provides all of the DNA material present in the biological sample that was not actively depleted which provides the advantage of reducing the sequencing costs as well as improving the data yield by sequencing smaller less diverse DNA samples.

In one embodiment, the nucleic acids of the invention are obtained from a biological sample. The biological sample from which the nucleic acids are obtained include but are not limited to whole blood, plasma, serum, tears, saliva, mucous, cerebrospinal fluid, teeth, bone, fingernails, feces, urine, tissue, biopsy, etc. The biological sample may include forensic samples such as teeth, bone, fingernails or the like. The biological sample may include tissue, a tissue biopsy, for example a resected lung tissue. The biological sample may include a clinical sample, which refers to a sample obtained in a clinical setting, such as a in a hospital, or clinic.

In one embodiment, the nucleic acids of the invention are obtained from an environmental sample, for example from water, soil, air, or rock.

In one embodiment, the nucleic acids of the invention are obtained from a forensic sample, for example, a sample obtained from an individual at a crime scene, from a piece of evidence, post-mortem, as a part of an ongoing investigation or the like.

In on embodiment, the nucleic acids of the invention are provided in a library.

The nucleic acids of the invention are either provided or extracted from a sample. Extraction can extract substantially all the nucleic acid sequences from a specimen. This can be, for example, nucleic acid sequences of the host and nucleic acid sequences of any non-human or non-host organism present in the specimen.

An extraction may produce host nucleic acids and non-host nucleic acids at a ratio of anywhere between 99.999:0.001 to 0.001:99.999. An extraction may produce targeted nucleic acids and nucleic acids of interest at a ratio of anywhere between 99.999:0.001 to 0.001:99.999. An extraction may produce nucleic acids to be depleted to nucleic acids to be retained/analyzed/sequenced at a ratio of anywhere between 99.999:0.001 to 0.001:99.999. An extraction may produce nucleic acids to be partitioned to nucleic acids to be retained/analyzed/sequenced at a ratio of anywhere between 99.999:0.001 to 0.001:99.999. An extraction from a biological sample may produce host nucleic acids to be depleted to nucleic acids from more than one non-host, to be retained/analyzed/sequenced, at a ratio of anywhere between 99.999:0.001 to 0.001:99.999. In these embodiments, the ratios can be equal to or fall anywhere in between 99.999:0.001 to 0.001:99.999, for example the ratio can be 99:1, 95:5, 90:10, 85:15, 80:20, 75:25, 70: 30, 65:35, 60:40, 55:45, 50:50, 45:55, 40:60, 35:65, 30:70, 25:75, 20:80, 15:85, 10:90, 5:95, and 1:99.

After the extraction, the extracted nucleic sequences can be fragmented to reduce the lengths of each extracted nucleic acids to a more manageable length for amplifying, sequencing or the like.

As provided herein, depletion of at least 10%, 15%, 20%, 25%, 30%, 40%, 50%, 60%, 70%, 80%, 90% of the starting nucleic acid material can be depleted or partitioned. This depletion or partitioning can be achieved in no greater than 10 minutes, 15 minutes, 20 minutes, 30 minutes, 45 minutes, 60 minutes, 75 minutes, 90 minutes, 105 minutes, 120 minutes, 150 minutes, 3 hours, 4 hours, 5 hours, 6 hours, 7 hours, 8 hours, 9 hours, 10 hours, 11 hours or 12 hours.

In one embodiment, the nucleic acids of the invention are adapter-ligated. Nucleic acids of the invention to be adapter-ligated can range from 10 bp to 1000 bp. For example the nucleic acid to be adapter-ligated may be at least 10, 15, 20, 25, 50, 75, 100, 125, 150, 175, 200, 25, 300, 350, 400, 450, 500, 550, 600, 650, 700, 750, 800, 850, 900, 950, or 1000 bp.

In one specific embodiment, the nucleic acid to be adapter ligated is 100 bp. In one specific embodiment, the nucleic acid to be adapter ligated is 200 bp. In one specific embodiment, the nucleic acid to be adapter ligated is 300 bp. In one specific embodiment, the nucleic acid to be adapter ligated is 400 bp. In one specific embodiment, the nucleic acid to be adapter ligated is 500 bp.

In some embodiments a sample comprises a library of nucleic acid fragments, wherein the nucleic acid fragments are adapter-ligated on their 5' and 3' ends. In such embodiments an adapter is ligated to each end of each of the nucleic acid fragments, at the 5' and 3' ends. In other embodiments an adapter may be ligated to only one end of each of the fragments. In some embodiments, adapters further comprise intervening sequence between the 5' terminal end and/or the 3' terminal end. For example an adapter can further comprise a barcode sequence.

In some embodiments the adapter is a nucleic acid that is ligatable to both strands of a double-stranded DNA molecule.

In some embodiments, adapters are ligated prior to depletion/enrichment. In other embodiments, adapters are ligated at a later step.

In some embodiments the adapters are linear. In some embodiments the adapters are linear Y-shaped. In some embodiments the adapters are linear circular. In some embodiments the adapters are hairpin adapters.

In various embodiments the adapter may be a hairpin adapter i.e., one molecule that base pairs with itself to form a structure that has a double-stranded stem and a loop, where the 3' and 5' ends of the molecule ligate to the 5' and 3' ends of the double-stranded DNA molecule of the fragment, respectively.

Alternately, the adapter may be a Y-adapter ligated to one end or to both ends of a fragment, also called a universal adapter. Alternately, the adapter may itself be composed of two distinct oligonucleotide molecules that are base paired with one another. Additionally a ligatable end of the adapter may be designed to be compatible with overhangs made by cleavage by a restriction enzyme, or it may have blunt ends or a 5' T overhang.

The adapter may include double-stranded as well as single-stranded molecules. Thus the adapter can be DNA or RNA, or a mixture of the two. Adapters containing RNA may be cleavable by RNase treatment or by alkaline hydrolysis.

Adapters can be 10 to 100 bp in length although adapters outside of this range are usable without deviating from the present invention. In specific embodiments, the adapter is at least 10 bp, at least 15 bp, at least 20 bp, at least 25 bp, at least 30 bp, at least 35 bp, at least 40 bp, at least 45 bp, at least 50 bp, at least 55 bp, at least 60 bp, at least 65 bp, at least 70 bp, at least 75 bp, at least 80 bp, at least 85 bp, at least 90 bp, or at least 95 bp in length.

In certain cases, an adapter may comprise an oligonucleotide designed to match a nucleotide sequence of a particular region of the host genome, e.g., a chromosomal region whose sequence is deposited at NCBI's Genbank database or other databases. Such an oligonucleotide may be employed in an assay that uses a sample containing a test genome, where the test genome contains a binding site for the oligonucleotide. In further examples the fragmented nucleic acid sequences may be derived from one or more DNA sequencing libraries. An adapter may be configured for a next generation sequencing platform, for example for use on an Illumina sequencing platform or for use on an Ion-Torrents platform, or for use with Nanopore technology.

Guide RNAs

Provided herein are guide RNAs (gRNAs), wherein the gRNAs are complementary to (selective for, can hybridize with) targeted sites or targeted sequences in the nucleic acids, for example in genomic DNA from a host. In one embodiment, the present invention provides a guide RNA library which comprises a collection of gRNAs, configured to hybridize with a nucleic acid sequence targeted for depletion or partitioning.

In one embodiment, the gRNAs are selective for target nucleic acids (or targeted sequences) in a sample, but are not selective for sequences of interest in the sample.

In one embodiment, the gRNAs are selective for host nucleic acids in a biological sample from a host, but are not selective for non-host nucleic acids in the sample from a host. In one embodiment, the gRNAs are selective for non-host nucleic acids from a biological sample from a host but are not selective for the host nucleic acids in the sample. In one embodiment, the gRNAs are selective for both host nucleic acids and a subset of the non-host nucleic acids in a biological sample from a host. For example, where a complex biological sample comprises host nucleic acids and nucleic acids from more than one non-host organisms, the gRNAs may be selective for more than one of the non-host species. In such embodiments, the gRNAs are used to serially deplete or partition the sequences that are not of interest. For example, saliva from a human contains human DNA, as well as the DNA of more than one bacterial species, but may also contain the genomic material of an unknown pathogenic organism. In such an embodiment, gRNAs directed at the human DNA and the known bacteria can be used to serially deplete the human DNA, and the DNA of the known bacterial, thus resulting in a sample comprising the genomic material of the unknown pathogenic organism.

In an exemplary embodiment, the gRNAs are selective for human host DNA obtained from a biological sample from the host, but do not hybridize with DNA from an unknown organism (e.g. pathogen(s)) also in the sample.

In some embodiments, the gRNAs are selective for a target nucleic acid sequences which are followed by Protospacer Adjacent Motif (PAM) sequences that can be bound by a Cas9. In some embodiments, the sequence of the gRNAs is determined by the CRISPR/Cas system protein type. For example, in various embodiments the gRNAs may be tailored to different Cas9 types as the PAM sequence can vary by the species of the bacteria from which Cas9 is derived.

gRNAs can range in size for example, from 50-250 base pairs. For example a gRNA can be at least 50 bp, 55 bp, 60 bp, 65 bp, 70 bp, 75 bp, 80 bp, 85 bp, 90 bp, 95 bp, 100 bp, 110 bp, 120 bp, 125 bp, 130 bp, 140 bp, 150 bp, 160 bp, 170 bp, 175 bp, 180 bp, 190 bp, or 195 bp. In specific embodiments, the gRNA is 80 bp, 90 bp, 100 bp, or 110 bp. Each target-specific gRNA comprises a base pair sequence that is complementary to a pre-defined site in a target nucleic acid that is followed by a Protospacer Adjacent Motif or (PAM) sequence that can be bound by a CRISPR/Cas system protein, for example a Cas9 protein, derived from a bacterial species. In specific embodiments, the base pair sequence of the gRNA that is complementary to a pre-defined site in a target nucleic acid is 15, 16, 17, 18, 19, 20, 25, 30, 35, 40, 45, or 50 base pairs.

The present invention also provides for gRNA libraries. A gRNA library can comprise a number of different species-specific gRNAs each, configured to hybridize with (be selective for) a nucleic acid sequence being targeted for depletion or partitioning. Each gRNA includes a target-specific guide sequence and a stem loop binding site that is formed to bind with a particular CRISPR/Cas system protein, for example with a Cas9 protein. The library can comprise a plurality of different guide RNAs, each having a different 15 to 20 base pair sequence that is complementary to a different pre-defined site in the nucleic acid being targeted, that is followed by an appropriate PAM sequence that can be bound by a CRISPR/Cas system protein. For each guide RNA the PAM sequence is present in the pre-defined DNA target sequence of the nucleic acid of interest but is not present in the corresponding target specific guide sequence.

Generally according to the present invention, any nucleic acid sequence in a genome of interest, with a pre-defined target sequence followed by the appropriate PAM sequence can be hybridized by a corresponding guide RNA provided in the guide RNA library and bound by CRISPR/Cas system protein, for example Cas9. In various embodiments the gRNA library may be tailored to different CRISPR/Cas system proteins, for example different Cas9 types since the PAM sequence can vary by the species of the bacteria from which protein is derived.

Different target specific sequences in the gRNAs can be generated. This can be done by using a promoter for a bacteriophage RNA polymerase, e.g., the RNA polymerase from bacteriophage T3, T7, SP6 or the like. Accordingly each different T7 RNA polymerase promoter provides a different target specific sequence suitable for hybridizing to a different target nucleic acid sequence. A non-limiting exemplary set of forward primers usable for both annealing and subsequent PCR reactions is listed in Tables 1 and 2 of Example 1 provided below.

Without being limited to theory, the distance between gRNAs to arrive at >95% cleavage of the target nucleic acid can be computed, if the gRNAs display ~100% efficacy: this can be computed by measuring the distribution of library size and determining the mean, N and the standard deviation SD; N−2SD=minimum size for >95% of the library, ensuring that there is one guide RNA per fragment of this size to ensure >95% depletion. This can also be described as the Maximum distance between guide RNAs=Mean of library size−2× (standard deviation of library size).

In the embodiments provided herein a gRNA library can be amplified to include a large number of copies of each different gRNA as well as a large number of different gRNAs as may be suitable to for the desired depletion results. The number of unique gRNAs in a given guide RNA library may range from 1 unique gRNAs to as many as $10^{10}$ unique gRNAs or approximately 1 unique guide RNA sequence for every 2 base pairs in the human genome. In some embodiments, the library comprises, at least $10^2$ unique gRNAs. In some embodiments library comprises at least $10^2$, at least $10^3$, at least $10^4$, at least $10^5$, at least $10^6$, at least $10^7$, at least $10^8$, at least $10^9$, at least $10^{10}$ unique gRNAs. In one exemplary embodiment, the library comprises about $10^3$ unique gRNAs.

In the embodiments provided herein, the methods comprise contacting a sample comprising nucleic acids with a plurality of CRISPR/Cas9 system protein-gRNA complexes, wherein the gRNAs are complementary to target sequences, such sequences targeted for depletion. In some embodiments, the method comprises using gRNAs which can base-pair with the targeted sites, wherein the sample is contacted with at least $10^2$ unique gRNAs. In some embodiments the sample is contacted with at least $10^2$, at least $10^3$, at least $10^4$, at least $10^5$, at least $10^6$, at least $10^7$, at least $10^8$, at least $10^9$, at least $10^{10}$ unique gRNAs. In one exemplary embodiment, the sample is contacted with about $10^3$ unique gRNAs.

In the embodiments provided herein, the methods comprise contacting a sample with at least $10^2$ unique CRISPR/Cas system protein-gRNA complexes, where the unique nature of the complex is determined by the unique nature of the gRNA itself. For example, 2 unique CRISPR/Cas system protein-gRNA complexes may share the same CRISPR/Cas system protein, but the gRNAs differ, even if by only 1 nucleotide. Thus, in some embodiments, the method comprises contacting a sample with at least $10^2$ unique CRISPR/Cas system protein-gRNA complexes. In some embodiments the sample is contacted with at least $10^2$, at least $10^3$, at least $10^4$, at least $10^5$, at least $10^6$, at least $10^7$, at least $10^8$, at least $10^9$, at least $10^{10}$ unique CRISPR/Cas system protein-gRNA complexes. In one exemplary embodiment, the sample is contacted with about $10^3$ unique CRISPR/Cas system protein-gRNA complexes.

In the embodiments provided herein, the methods comprise contacting a sample comprising a genomic DNA with a plurality of CRISPR/Cas9 system protein-gRNA complexes, wherein the gRNAs are complementary to sites targeted in the genome for depletion. In some embodiments, the method comprises using gRNAs which can base-pair with the targeted DNA, wherein the target site of interest is spaced at least every 1 bp, at least every 2 bp, at least every 3 bp, at least every 4 bp, at least every 5 bp, at least every 6 bp, at least every 7 bp, at least every 8 bp, at least every 9 bp, at least every 10 bp, at least every 11 bp, at least every 12 bp, at least every 13 bp, at least every 14 bp, at least every 15 bp, at least every 16 bp, at least every 17 bp, at least every 18 bp, at least every 19 bp, 20 bp, at least every 25 bp, at least every 30 bp, at least every 40 bp, at least every 50 bp, at least every 100 bp, at least every 200 bp, at least every 300 bp, at least every 400 bp, at least every 500 bp, at least every 600 bp, at least every 700 bp, at least every 800 bp, at least every 900 bp, at least every 1000 bp, at least every 2500 bp, at least every 5000 bp, at least every 10,000 bp, at least every 15,000 bp, at least every 20,000 bp, at least every 25,000 bp, at least every 50,000 bp, at least every 100,000 bp, at least every 250,000 bp, at least every 500,000 bp, at least every 750,000 bp, or even at least every 1,000,000 bp across a genome of interest.

In the embodiments provided herein, the methods comprise contacting a sample comprising nucleic acids targeted for depletion with a plurality of CRISPR/Cas9 system protein-gRNA complexes, wherein the gRNAs are complementary to the nucleic acids targeted for depletion. In some embodiments the molar ratio of the gRNA:nucleic acids targeted for depletion is 1:1, 5:1, 10:1, 50:1, 100:1, 150:1, 250:1,500:1,750:1,1000:1, 1500:1, 2000:1, 2500:1, 5000:1, 7500:1, or even 10,000:1. In an exemplary embodiment the molar ratio of the gRNA:nucleic acids targeted for depletion is 500:1.

In the embodiments provided herein, the methods comprise contacting a sample comprising nucleic acids targeted for depletion with a plurality of CRISPR/Cas9 system protein-gRNA complexes, wherein the gRNAs are complementary to the nucleic acids targeted for depletion. In some embodiments the weight to weight ratio of the gRNA:nucleic acids targeted for depletion is 1:1, 5:1, 10:1, 20:1, 30:1, 40:1, 50:1, 60:1, 70:1, 80:1, 90:1, 100:1, 150:1, 250:1,500:1,750:1,1000:1, 1500:1, 2000:1, 2500:1, 5000:1, 7500:1, or even 10,000:1. In an exemplary embodiment the weight to weight ratio of the gRNA:nucleic acids targeted for depletion is ranges between 50:1 and 100:1.

The following description refers to FIG. 1 as an exemplary embodiment. In FIG. 1, a guide RNA library (1050) comprises a large number of different human specific gRNAs (1055) each configured to hybridize with a human DNA or nucleic acid sequence being targeted for depletion from the collection of DNA extraction fragments (1025) or any other DNA fragments that can be depleted because they are not of interest. In this embodiment, the nucleic acid sequences being targeted for depletion are not sequences that are present in the non-human genetic fragments (1030) that are of interest for further analyzed. Each guide RNA (1055) includes a target specific guide sequence (1060) and a stem loop binding site (1065) that is formed to bind with a Cas9 protein. Each target specific guide sequence (1060) is a 15 to 20 base pair sequence that is complementary to a pre-defined site in the human genome that is followed by a Protospacer Adjacent Motif or (PAM) sequence that can be bound by a Cas9 protein derived from a bacterial species. Other base pair lengths are usable ranging from about 8 to 100 base pairs without deviating from the present invention.

In FIG. 1, the different target specific sequence (1060) is generated by a different T7 RNA polymerase promoter sequences (1070) that contains a promoter for a bacteriophage RNA polymerase, e.g., the RNA polymerase from bacteriophage T3, T7, SP6 or the like. Accordingly each different T7 RNA polymerase promoter (1070) provides a different target specific sequence (1060) suitable for hybridizing to a different human DNA sequence.

In FIG. 1, the guide RNA library (1050) is amplified to include a large number of copies of each different gRNA (1055) as well as a large number of different gRNAs e.g. (1055a) (1055b) (1055n) as may be suitable to for the desired depletion results.

CRISPR/Cas System Proteins

Provided herein compositions and methods for the depletion of unwanted nucleic acids, and/or enrichment of sequences of interest in a sample. These compositions and methods utilize a CRISPR/Cas system protein.

In some embodiments, CRISPR/Cas system proteins include proteins from CRISPR Type I systems, CRISPR Type II systems, and CRISPR Type III systems.

In some embodiments, CRISPR/Cas system proteins can be from any bacterial or archaeal species.

In some embodiments, the CRIPR/Cas system proteins are from, or are derived from CRISPR/Cas system proteins from *Streptococcus pyogenes, Staphylococcus aureus, Neisseria meningitidis, Streptococcus thermophiles, Treponema denticola, Francisella tularensis, Pasteurella multocida, Campylobacter jejuni, Campylobacter lari, Mycoplasma gallisepticum, Nitratifractor salsuginis, Parvibaculum lavamentivorans, Roseburia intestinalis, Neisseria cinerea, Gluconacetobacter diazotrophicus, Azospirillum, Sphaerochaeta globus, Flavobacterium columnare, Fluviicola taffensis, Bacteroides coprophilus, Mycoplasma mobile, Lactobacillus farciminis, Streptococcus pasteurianus, Lactobacillus johnsonii, Staphylococcus pseudintermedius, Filifactor alocis, Legionella pneumophila, Suterella wadsworthensis,* or *Corynebacter diphtheria.*

In some embodiments, examples of CRISPR/Cas system proteins can be naturally occurring or engineered versions.

In some embodiments, naturally occurring CRISPR/Cas system proteins include Cas9, Cpf1, Cas3, Cas8a-c, Cas10, Cse1, Csy1, Csn2, Cas4, Csm2, and Cm5. In an exemplary embodiment, the CRISPR/Cas system protein comprises Cas9.

A "CRISPR/Cas system protein-gRNA complex" refers to a complex comprising a CRISPR/Cas system protein and a guide RNA. The guide RNA may be composed of two molecules, i.e., one RNA ("crRNA") which hybridizes to a target and provides sequence specificity, and one RNA, the "tracrRNA", which is capable of hybridizing to the crRNA. Alternatively, the guide RNA may be a single molecule (i.e., a gRNA) that contains crRNA and tracrRNA sequences. A CRISPR/Cas system protein may be at least 60% identical (e.g., at least 70%, at least 80%, or 90% identical, at least 95% identical or at least 98% identical or at least 99% identical) to a wild type CRISPR/Cas system protein. The CRISPR/Cas system protein may have all the functions of a wild type CRISPR/Cas system protein, or only one or some of the functions, including binding activity, nuclease activity, and nuclease activity.

The term "CRISPR/Cas system protein-associated guide RNA" refers to a guide RNA as described above (comprising a crRNA molecule and a tracrRNA molecule, or comprising a single RNA molecule that includes both crRNA and tracrRNA sequences). The CRISPR/Cas system protein-associated guide RNA may exist as isolated RNA, or as part of a CRISPR/Cas system protein-gRNA complex.

Cas9

In some embodiments, the CRISPR/Cas system protein comprises Cas9. The Cas9 of the present invention can be isolated, recombinantly produced, or synthetic.

Cas9 proteins that can be used in the embodiments herein can be found in http://www.nature.com/nature/journal/v520/n7546/full/nature14299.html.

In some embodiments, the Cas9 is a Type II CRISPR system derived from *Streptococcus pyogenes, Staphylococcus aureus, Neisseria meningitidis, Streptococcus thermophiles, Treponema denticola, Francisella tularensis, Pasteurella multocida, Campylobacter jejuni, Campylobacter lari, Mycoplasma gallisepticum, Nitratifractor salsuginis, Parvibaculum lavamentivorans, Roseburia intestinalis, Neisseria cinerea, Gluconacetobacter diazotrophicus, Azospirillum, Sphaerochaeta globus, Flavobacterium columnare, Fluviicola taffensis, Bacteroides coprophilus, Mycoplasma mobile, Lactobacillus farciminis, Streptococcus pasteurianus, Lactobacillus johnsonii, Staphylococcus pseudintermedius, Filifactor alocis, Legionella pneumophila, Suterella wadsworthensis,* or *Corynebacter diphtheria.*

In some embodiments, the Cas9 is a Type II CRISPR system derived from *S. pyogenes* and the PAM sequence is NGG located on the immediate 3' end of the target specific guide sequence. The PAM sequences of Type II CRISPR systems from exemplary bacterial species can also include: *Streptococcus pyogenes* (NGG), *Staph aureus* (NNGRRT), *Neisseria meningitidis* (NNNNGA TT), *Streptococcus thermophiles* (NNAGAA) and *Treponema denticola* (NAAAAC) which are all usable without deviating from the present invention. ((http://www.nature.com/nature/journal/v520/n7546/full/nature14299.html)).

In one exemplary embodiment, Cas9 sequence can be obtained, for example, from the pX330 plasmid (available from Addgene), re-amplified by PCR then cloned into pET30 (from EMD biosciences) to express in bacteria and purify the recombinant 6His tagged protein.

The "Cas9-gRNA complex" refers to a complex comprising a Cas9 protein and a guide RNA. The guide RNA may be composed of two molecules, i.e., one RNA ("crRNA") which hybridizes to a target and provides sequence specificity, and one RNA, the "tracrRNA", which is capable of hybridizing to the crRNA. Alternatively, the guide RNA may be a single molecule (i.e., a gRNA) that contains crRNA and tracrRNA sequences. A Cas9 protein may be at least 60% identical (e.g., at least 70%, at least 80%, or 90% identical, at least 95% identical or at least 98% identical or at least 99% identical) to a wild type Cas9 protein, e.g., to the *Streptococcus pyogenes* Cas9 protein. The Cas9 protein may have all the functions of a wild type Cas9 protein, or only one or some of the functions, including binding activity, nuclease activity, and nuclease activity.

The term "Cas9-associated guide RNA" refers to a guide RNA as described above (comprising a crRNA molecule and a tracrRNA molecule, or comprising an RNA molecule that includes both crRNA and tracrRNA sequences). The Cas9-associated guide RNA may exist as isolated RNA, or as part of a Cas9-gRNA complex.

Catalytically Dead CRISPR/Cas System Proteins

In some embodiments, engineered examples of CRISPR/Cas system proteins include catalytically dead CRISPR/Cas system proteins. The term "catalytically dead" generally refers to a CRISPR/Cas system protein that has inactivated HNH and RuvC nucleases. Such a protein can bind to a target site in any nucleic acid (where the target site is determined by the guide RNA), but the protein is unable to cleave or nick the double-stranded DNA.

In some embodiments, the catalytically dead CRISPR/Cas system protein is dCas9, dCpf1, dCas3, dCas8a-c, dCas10, dCse1, dCsy1, dCsn2, dCas4, dCsm2, or dCm5.

Figure 2:
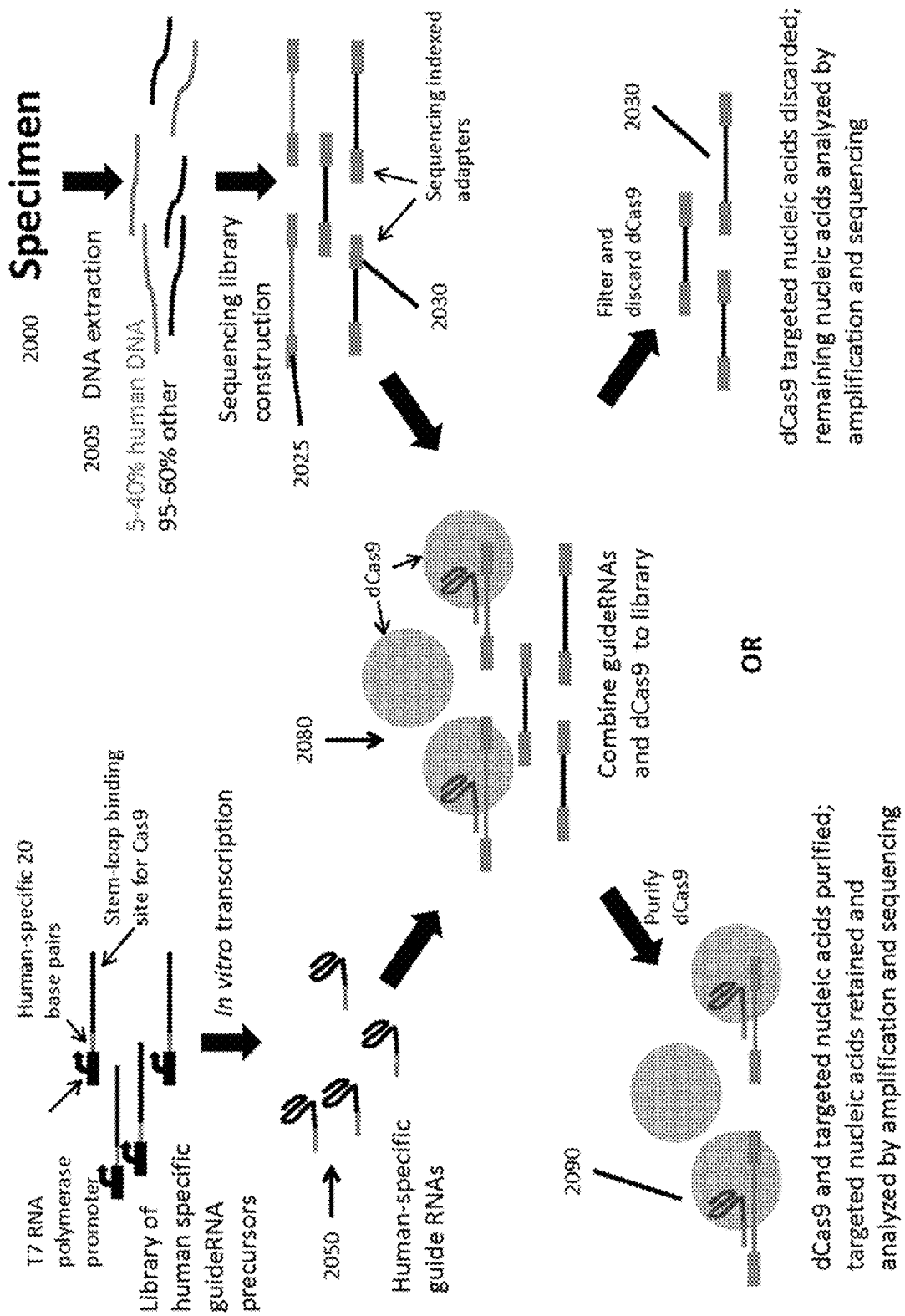
FIG. 2 illustrates a general schematic of the depletion method using catalytically dead Cas9 to partition libraries into target and non-target sequences.
Figure 3:
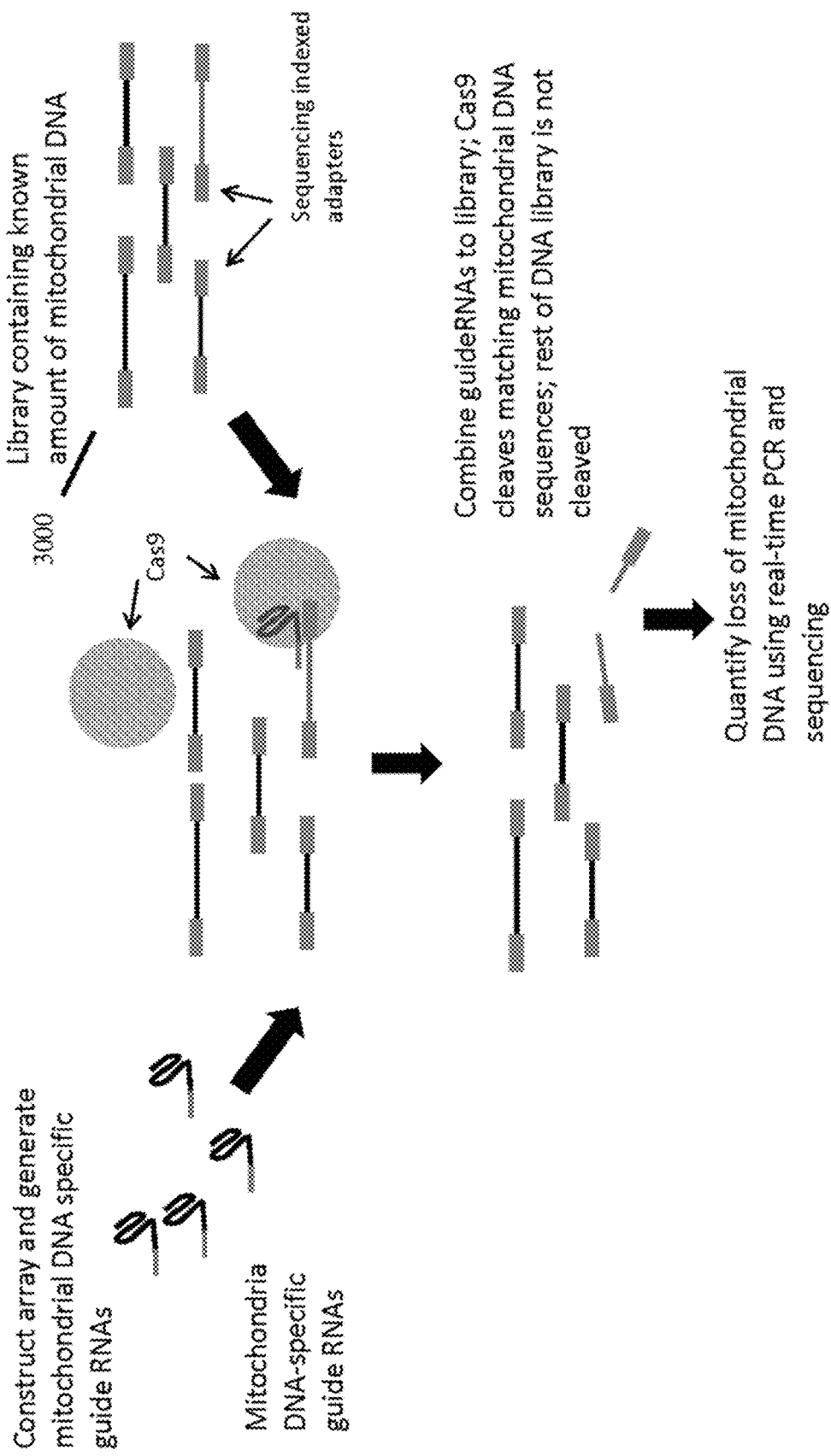
FIG. 3 illustrates an exemplary strategy to deplete mitochondrial DNA from a sequencing library, leaving only non-mitochondrial DNA for sequencing.

In one embodiment the catalytically dead CRISPR/Cas system protein is a dCas9. Accordingly the dCas9 allows partition of the mixture into unbound nucleic acids and dCas9-bound fragments targeted for partitioning. In one embodiment, a dCas9/gRNA complex binds to targets determined by the gRNA sequence. The dCas9 bound can prevent cutting by Cas9 while other manipulations proceed. This is depicted in FIG. 2. In one embodiment, the dCas9/gRNA complex binds to the targets determined by the gRNA sequence, and the bound portion of the target nucleic acid sample can be removed by binding of an affinity tag (e.g., biotin) previously attached to the dCas9 protein. The bound nucleic acid sequences can be eluted from the Cas9/gRNA complex by denaturing conditions and then amplified and sequenced. Conversely, in another embodiment, those dCas9 targeted nucleic acids can be discarded, and the remaining nucleic acids can be analyzed by amplification and sequencing.

CRISPR/Cas System Protein Nickases

In some embodiments, engineered examples of CRISPR/Cas system proteins also include Cas nickases. A Cas nickase refers to a modified version of a CRISPR/Cas system protein, containing a single inactive catalytic domain.

In some embodiments, the CRISPR/Cas system protein nickase is Cas9 nickase, Cpf1 nickase, Cas3 nickase, Cas8a-c nickase, Cas10 nickase, Cse1 nickase, Csy1 nickase, Csn2 nickase, Cas4 nickase, Csm2 nickase, or Cm5 nickase.

In one embodiment, the CRISPR/Cas system protein nickase is Cas9 nickase.

In some embodiments, a Cas9 nickase can be used to bind to target sequence. The term "Cas9 nickase" refers to a modified version of the Cas9 protein, containing a single inactive catalytic domain, for example, either the RuvC- or the HNH-domain. With only one active nuclease domain, the Cas9 nickase cuts only one strand of the target DNA, creating a single-strand break or "nick". Depending on which mutant is used, the guide RNA-hybridized strand or the non-hybridized strand may be cleaved. Cas9 nickases bound to 2 gRNAs that target opposite strands can create a double-strand break in the DNA. This "dual nickase" strategy increases the specificity of cutting because it requires that both Cas9/gRNA complexes be specifically bound at a site before a double-strand break is formed.

Figure 7:
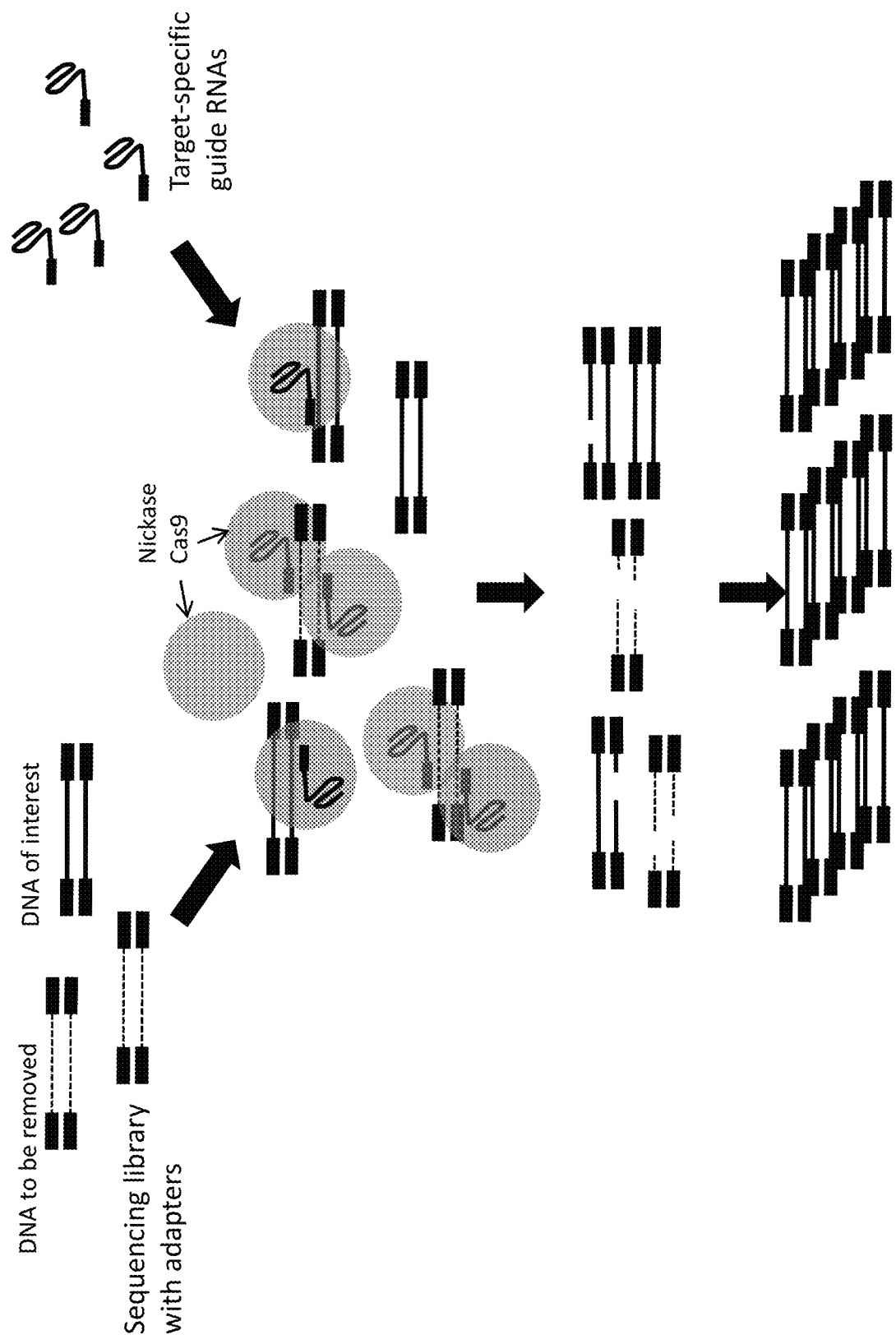
FIG. 7 illustrates Cas9 Nickase-mediated depletion of DNA.

In an exemplary embodiment, depletion of DNA can be carried out using a Cas9 nickase. In one embodiment, the method comprises: making a DNA sequencing library comprising DNA to be removed (for example human DNA not of interest) and DNA of interest (for example an DNA from an unknown pathogen); designing guide RNAs so that all the DNA to be depleted will have two guide RNA binding sites in close proximity (for example, less than 15 bases apart) on opposite DNA strands; adding Cas9 Nickase and guide RNA to the DNA library. In this embodiment, the Cas9 Nickase recognizes its target sites on the DNA to be removed and cuts only one strand. For DNA to be depleted, two separate Cas9 Nickases can cut both strands of the DNA to be removed (e.g. human DNA) in close proximity; only the DNA to be removed (e.g. human DNA) will have two Cas9 nickase sites in close proximity which creates a double stranded break. If a Cas9 Nickase recognizes non-specifically or at low affinity a site on the DNA of interest (e.g. pathogen DNA), it will only cut one strand which would not prevent subsequent PCR amplification or downstream processing of the DNA molecule. This is pictorially depicted in FIG. 7. In this embodiment, the chances of two guide RNAs recognizing two sites non-specifically in close enough proximity is negligible ($<1\times10-14$). This embodiment would be particularly useful if regular, Cas9-mediated cleavage cuts too much of the DNA of interest.

Dissociable and Thermostable CRISPR/Cas System Proteins

Although CRISPR/Cas System proteins can be used in combination with a library of guide RNAs to efficiently deplete a collection of target DNA, large amounts (e.g. >30 pmoles) of CRISPR/Cas System proteins and guide RNAs may be needed. One reason for this usually >100 fold excess amount over target DNA is that, unlike classical restriction enzymes such as EcoRI, which detach completely from their target DNA after cleavage, CRISPR/Cas System proteins are not completely recycled after completion of the cutting reaction. CRISPR/Cas System proteins, for example Cas9, can remain bound to one of the two daughter DNA product molecules (see FIG. 11, open circles on the left). As a result, more CRISPR/Cas System proteins and gRNA may need to be provided in order to achieve complete depletion of unwanted DNA.

In some embodiments, to overcome this problem, dissociable CRISPR/Cas System proteins are provided herein. For example upon cleavage of targeted sequences, the CRISPR/Cas System protein can be made to dissociate from the gRNA, or from the target. In some embodiments, the dissociation is induced by elevating the temperature of the reaction. This can act to increase processivity of the enzyme, by allowing it to complex with available gRNAs, re-associate with additional target sequences and generate additional cleaved target sequences.

In some embodiments to overcome this problem, thermostable CRISPR/Cas System proteins are provided herein. In such embodiments, the reaction temperature is elevated, inducing dissociation of the protein; the reaction temperature is lowered, allowing for the generation of additional cleaved target sequences. In some embodiments, thermostable CRISPR/Cas system proteins maintain at least 50% activity, at least 55% activity, at least 60% activity, at least 65% activity, at least 70% activity, at least 75% activity, at least 80% activity, at least 85% activity, at least 90% activity, at least 95% activity, at least 96% activity, at least 97% activity, at least 98% activity, at least 99% activity, or 100% activity, when maintained for at least 75° C. for at least 1 minute. In some embodiments, thermostable CRISPR/Cas system proteins maintain at least 50% activity, when maintained for at least 1 minute at least at 75° C., at least at 80° C., at least at 85° C., at least at 90° C., at least at 91° C., at least at 92° C., at least at 93° C., at least at 94° C., at least at 95° C., 96° C., at least at 97° C., at least at 98° C., at least at 99° C., or at least at 100° C. In some embodiments, thermostable CRISPR/Cas system proteins maintain at least 50% activity, when maintained at least at 75° C. for at least 1 minute, 2 minutes, 3 minutes, 4 minutes, or 5 minutes. In some embodiments, a thermostable CRISPR/Cas system protein maintains at least 50% activity when the temperature is elevated, lowered to 25° C.-50° C. In some embodiments, the temperature is lowered to 25° C., to 30° C., to 35° C., to 40° C., to 45° C., or to 50° C. In one exemplary embodiment, a thermostable enzyme retains at least 90% activity after 1 min at 95° C.

In some embodiments, the thermostable CRISPR/Cas system protein is thermostable Cas9, thermostable Cpf1, thermostable Cas3, thermostable Cas8a-c, thermostable Cas10, thermostable Cse1, thermostable Csy1, thermostable Csn2, thermostable Cas4, thermostable Csm2, or thermostable Cm5.

In some embodiments the thermostable CRISPR/Cas system protein is thermostable Cas9.

In one exemplary embodiment, thermostable Cas9 complexed with a guide RNAs (for example a gRNA library against human DNA) can be applied to a sequencing library of DNA mixture (containing for example 95% human DNA and 5% viral DNA). As depicted in FIG. 11 (grey circles on the right), after allowing Cas9 to digest for a period of time, the temperature of the sample mixture can be elevated, for example up to 95° C. or greater, which can cause DNA denaturation, as well as dissociation of gRNA and Cas9 from the DNA targets. The binding of Cas9 to gRNAs can be increased so that the Cas9-gRNA dissociates from the DNA target as an intact complex, despite of DNA denaturation. Dimethyl sulfoxide can be added to reduce the temperature required for DNA denaturation, so that the Cas9 protein structure is not be affected. Cas9 preferentially binds to target sites that have not been cut, and a thermostable Cas9 can retain activity after boiling. Because of these features, by elevating the temperature, for example up to 100☐C, and cooling down the reaction to, for example, 37° C., a thermostable Cas9 can remain capable of binding to its gRNA and cutting more of its substrate. By allowing the recycling of Cas9, the depletion efficiency can be increased, and as less Cas9 will be needed in the reaction, the off-target (non-specific) cleavage probability can also be decreased.

Thermostable CRISPR/Cas System proteins can be isolated, for example, identified by sequence homology in the genome of thermophilic bacteria *Streptococcus thermophilus* and *Pyrococcus furiosus*. CRISPR/Cas system genes can then be cloned into an expression vector. In one exemplary embodiment, a thermostable Cas9 protein is isolated.

In another embodiment, a thermostable CRISPR/Cas system protein can be obtained by in vitro evolution of a non-thermostable CRISPR/Cas system protein. The sequence of a CRISPR/Cas system protein can be mutagenized to improve its thermostability. In some embodiments, this can be achieved by site-directed mutagenesis to remove excess loop sequences, increasing the number of ionic bridges between protein domains, or by diluting into droplets and PCR to create a pool of potential mutants. In one exemplary embodiment, a thermostable Cas9 is produced by in vitro evolution of a non-thermostable Cas9.

Methods of the Invention

Enrichment of Sequences of Interest/Depletion of Targeted Sequences

Provided herein are methods of enriching a sample for sequences of interest, by depleting targeted sequences that are not of interested (target sequences are sequences targeted for depletion).

In one embodiment, a method of enriching a sample for sequences of interest, comprises:

providing a sample comprising sequences of interest and targeted sequences for depletion, wherein the sequences of interest comprise less than 50%, less than 45%, less than 40%, less than 35%, less than 30%, less than 25%, less than 20%, less than 15%, less than 10%, less than 9%, less than 8%, less than 7%, less than 6%, less than 5%, less than 4%, less than 3%, less than 2%, less than 1%, less than 0.5%, less than 0.1%, less than 0.05%, less than 0.01%, less than 0.005%, or even less than 0.001% of the sample; contacting the sample with a plurality of CRISPR/Cas system protein-gRNA complexes, wherein the gRNAs are complementary to the targeted sequences, whereby the targeted sequences are cleaved. In an exemplary embodiment the CRISPR/Cas system protein is Cas9.

In one embodiment, a method of enriching a sample for non-mitochondrial DNA comprises: (a) providing a sample comprising mitochondrial DNA and non-mitochondrial DNA, wherein the mitochondrial DNA and non-mitochondrial DNA are adapter-ligated, and wherein the adapters are ligated to the 5' and 3' ends of the mitochondrial DNA and non-mitochondrial DNA; (b) contacting the sample with a plurality of CRISPR/Cas system protein-gRNA complexes, wherein the gRNAs are complementary to the mitochondrial DNA, thereby generating mitochondrial DNA adapter ligated only on one end and non-mitochondrial DNA adapter ligated on both the 5' and 3' ends; and (c) enriching the sample for non-mitochondrial DNA. In some embodiments the sample is enriched using adapter-specific PCR. In some embodiments, the enriching comprises treating the product of step (b) with an enzyme that has exonuclease activity, for example Exonuclease III or BAL-31. For example, if Exonuclease III is utilized, the adapters may be Y-shaped. If BAL-31 is utilized, the adapters may comprise poly-G tails. In some embodiments the sample is enriched by purification of the sequences of interest.

In another embodiment, a method of enriching a sample comprises: (a) providing a sample comprising nucleic acids from a first genome and nucleic acids from a second genome, wherein the nucleic acids from the first genome are adapter-ligated on their 5' and 3' ends and wherein the nucleic acids from the second genome are adapter-ligated on their 5' and 3' ends; (b) contacting the sample with a plurality of CRISPR/Cas system protein-gRNA complexes, wherein the gRNAs are complementary to sites on the nucleic acids from the first genome, thereby generating nucleic acids from the first genome adapter ligated only on one end and nucleic acids from the second genome adapter ligated on both the 5' and 3' ends; and (c) enriching the sample for nucleic acids from the first genome. In some embodiments the sample is enriched using adapter-specific PCR. In some embodiments, the enriching comprises treating the product of step (b) with an enzyme that has exonuclease activity, for example Exonuclease III or BAL-31. For example, if Exonuclease III is utilized, the adapters may be Y-shaped. If BAL-31 is utilized, the adapters may comprise poly-G tails. In some embodiments the sample is enriched by purification of the sequences of interest.

In another embodiment, a method of enriching a sample for non-host nucleic acids comprises: providing a sample comprising host nucleic acids and non-host nucleic acids, wherein the host nucleic acids and non-host nucleic acids are adapter-ligated, and wherein the adapters are ligated to the 5' and 3' ends of the host nucleic acids and the non-host nucleic acids; contacting the sample with a plurality of CRISPR/Cas system protein-gRNA complexes, wherein the gRNAs are complementary to targeted sites in the host nucleic acids, thereby generating host-nucleic acids adapter ligated only on one end and non-host nucleic acids adapter ligated on both the 5' and 3' ends; and amplifying the products using adapter-specific PCR or purifying, or treatment with exonuclease.

In another embodiment, provided herein is a method for serially depleting targeted nucleic acids in a sample comprising:(a) providing a sample comprising host nucleic acids and non-host nucleic acids, wherein the non-host nucleic acids comprise nucleic acids from at least one known non-host organism and nucleic acids from at least one unknown non-host organism; (b) contacting the sample with a plurality of CRISPR/Cas system protein-gRNA complexes, wherein the gRNAs are configured to hybridize to targeted sequences in the host nucleic acids, whereby a portion of the host nucleic acids are cleaved; (c) contacting the sample with a plurality of CRISPR/Cas system protein-gRNA complexes, wherein the gRNAs are configured to hybridize to targeted sequences in the at least one known non-host nucleic acids, whereby a portion of the at least one known non-host nucleic acids are cleaved; and (d) isolating the nucleic acids from the unknown non-host organism.

FIG. 1 provides a first non-limiting exemplary method relates to processing a human tissue specimen (1000). In a first step (1005) a DNA extraction extracts substantially all the nucleic acid sequences from the specimen (1000) including nucleic acid sequences of the human host and nucleic acid sequences of any non-human or non-host organism present in the specimen (1000). The DNA extraction step (1005) may produce about 95% human DNA (1010) and about 5% non-human DNA (1015) wherein the non-human DNA (1015) largely comprises microbial DNA and in the present example method embodiment the microbial or non-human DNA (1015) is of primary interest for further DNA analysis. After the DNA extraction step (1005) the extracted nucleic sequences (1010) and (1015) are fragmented to reduce the lengths of each extracted nucleic sequence to a more manageable length for amplifying, sequencing or the like. An adapter (1020) is ligated to each end of each of the fragments. Each extracted nucleic sequence fragment or genomic fragment comprises a region of a genome, e.g., each fragment (1025) includes a nucleic acid sequence, shown as a dashed line between two adapters (1020), from a region of the human genome while each fragment (1030) includes a nucleic acid sequence, shown as a solid line between two adapters (1020), from a region of one of the non-host organisms extracted from the tissue sample. Each extracted nucleic acid or genomic fragment comprises a region of a genome, e.g., each fragment (1025) includes a nucleic acid sequence, shown as a dashed line between two adapters (1020), from a region of the human genome while each fragment (1030) includes a nucleic acid sequence, shown as a solid line between two adapters (1020), from a region of one of the non-host organisms extracted from the tissue sample. However, it will be recognized that the sequences are indistinguishable without further analysis.

An exemplary application of the compositions and methods described herein is provided in FIG. 1. The figure depicts a non-limiting exemplary embodiment of the present invention that includes a depletion method for depleting a DNA extraction of a biological sample. In FIG. 1, the entire fragmented DNA extraction (1025) and (1030) as well as the entire guide RNA library (1050) is mixed with a Cas9 protein in a mixture (1080). While in the mixture (1080) each target specific guide sequence (1060) hybridizes to matching nucleic acid sequences found in human DNA fragments (1025) and the Cas9 protein and the guide RNA stem binding sites (1065) form a guide RNA/Cas9 complex (1085) that binds guide RNA (1055) to the human DNA fragments (1025). If the guide RNA library (1050) is well designed, substantially all the human DNA fragments (1025) will be bound by a guide RNA/Cas9 complex. Thereafter the mixture (1080) is incubated in a manner that cases the Cas9 protein to cut or cleave both strands of each human DNA fragment (1025) that is bound by a guide RNA/Cas9 complex. After cutting, the human DNA fragment (1025) are in two pieces (1090) (1095) and any uncut DNA fragment (1030) remain intact with adapter (1020) still attached to each end and ready for amplification and further study.

In various further processing steps occurring after the depletion targets have been cut or cleaved the mixture (1080) may be sized-selectively filtered to separate uncut fragments (1030) from cut fragments (1090) and (1095). Thereafter the uncut fragments (1030) can be amplified and sequenced. Alternately the amplification process can be used to sort the cut from the uncut segments since in some amplification systems only segments having an adapter (1020) at each end of the fragment is amplified.

Another exemplary application of the compositions and methods described herein is provided in FIG. 2. FIG. 2 depicts a second non-limiting exemplary method relates to processing a specimen or sequencing library (2000) that involves partitioning, and not depletion. In a first step (2005) a DNA extraction extracts substantially all the nucleic acid sequences from the specimen (2000) including nucleic acid sequences of a human host and nucleic acid sequences of any other non-host organism present in the specimen (2000). In the present example the DNA extraction step (2005) may produce about 5 to 40% human DNA and about 95 to 60% non-human DNA. As described with respect to FIG. 1 above, the DNA extraction sample is fragmented and adapter ligated. A further described with respect to FIG. 1 above, a guide RNA library (2050) of gRNAs is developed to hybridize with a large number of different human specific gRNAs (2055) each configured to hybridize with a human DNA or nucleic acid sequence being targeted for binding by a Cas9 complex. However instead of cutting the targeted sequences, the method shown in FIG. 2 is used to partition the fragmented nucleic acid sample into two fractions which can each be amplified separately. As described above the guide library (2050) and fragmented DNA extraction sample are combined with Cas9 in a mixture (2080). However in the present example embodiment the CAs9 comprises a catalytically dead Cas9 (dCas9). The term "catalytically dead" refers to a Cas protein that has inactivated HNH and RuvC nucleases. Such a protein can bind to a target site in double-stranded DNA (where the target site is determined by the guide RNA), but the protein is unable to cleave or nick the double-stranded DNA. Accordingly the dCas9 partitions the mixture (2080) into unbound non-human DNA fragments (2030) and dCas9 bound human DNA fragments (2090). The dCas9/gRNA complex only binds to the targets determined by the gRNA sequence, and the bound portion of the target nucleic acid sample is removed by binding of an affinity tag (e.g., biotin) previously attached to the dCas9 protein. The bound nucleic acid sequences (2090) can be eluted from the Cas9/gRNA complex by denaturing conditions and then amplified and sequenced. Similarly, the unbound nucleic acid sequences (2030) can be amplified and sequenced.

Depletion of Large Fragments of DNA Without Adapters

In some embodiments, the methods provided herein are used for depletion. However, instead of cleaving a library containing adapters, the guide RNAs are chosen to cleave multiple times in a pool of fragmented DNA of a large size (e.g., anywhere from 100 bp-10 kb). Following cleavage with CRISPR/Cas system protein-gRNA complexes, the DNA is subjected to size selection to remove small fragments (e.g., at least ½ or ⅓ of the average size of intact fragments). This is assisted, for example, by treatment with Lambda exonuclease, which is a 5'phosphate specific-exonuclease that proceeds in a 5' to 3' direction and would attack any fragments that had previously been cut with the CRISPR/Cas system protein. The resulting libraries can then be subjected to sequencing by single-molecule sequencers that do not require sequencing adapters; or adapters can be ligated for downstream analyses.

Depletion Using Thermostable CRISPR/Cas System Proteins

In another embodiment, a method of generating cleaved targeted sequences in a sample comprises: (a) providing a sample comprising sequences of interest and targeted sequences for cleavage; (b) contacting the sample with a plurality of CRISPR/Cas system protein-gRNA complexes, wherein the gRNAs are complementary to the targeted sequences, thereby generating cleaved targeted sequences; (c) dissociating the CRISPR/Cas system protein from the cleaved targeted sequences; (d) generating additional cleaved targeted sequences; and (e) recovering the uncut sequences of interest. In some embodiments, the CRISPR/Cas system protein is thermostable. In some embodiments, the dissociating of the CRISPR/Cas system protein from the cleaved targeted sequences is achieved by elevating the temperature of the mixture of step (b) to at least 75°. In some embodiments, the generating of additional cleaved targeted sequences is achieved by lowering the temperature of the mixture of step (b) to at least 50°.

In another embodiment, a method of depleting targeted sequences in a sample comprises: (a) providing a sample comprising sequences of interest and targeted sequences for depletion; (b) contacting the sample with a plurality of CRISPR/Cas system protein-gRNA complexes, wherein the gRNAs are complementary to the targeted sequences, thereby generating cleaved targeted sequences, and wherein the CRISPR/Cas system protein is thermostable; (c) elevating the temperature of the mixture of step (b) to at least 75°; (d) lowering the temperature of the mixture of step (b) at least 50°; repeating steps (c) and (d) at least once; and (f) recovering the uncut sequences of interest.

CRISPR/Cas System Protein-Mediated Depletion in the Presence of a CRISPR/Cas Protein Nickase In some embodiments, depletion of unwanted, targeted nucleic acids can be carried out using a CRISPR/Cas system protein nickase. In one embodiment, the method comprises: making a DNA sequencing library comprising DNA to be removed (for example human DNA not of interest) and DNA of interest (for example an DNA from an unknown pathogen); designing guide RNAs so that all the DNA to be depleted will have two guide RNA binding sites in close proximity (for example, less than 15 bases apart) on opposite DNA strands; adding CRISPR/Cas system protein Nickase and guide RNAs to the DNA library. In this embodiment, the CRISPR/Cas system protein Nickase can recognize its target sites on the DNA to be removed and cuts only one strand. For DNA to be depleted, two separate CRISPR/Cas system protein Nickases can cut both strands of the DNA to be removed (e.g. human DNA) in close proximity; only the DNA to be removed (e.g. human DNA) will have two CRISPR/Cas system protein nickase sites in close proximity which creates a double stranded break. If a CRISPR/Cas system protein Nickase recognizes non-specifically or at low affinity a site on the DNA of interest (e.g. pathogen DNA), it can only cut one strand which would not prevent subsequent PCR amplification or downstream processing of the DNA molecule. This is pictorially depicted in FIG. 7. In this embodiment, the chances of two guide RNAs recognizing two sites non-specifically in close enough proximity is negligible ($<1\times10^{-14}$). This embodiment would be particularly useful if regular, CRISPR/Cas system protein-mediated cleavage cuts too much of the DNA of interest.

CRISPR/Cas System Protein-Mediated Depletion and Biotin Labeling

In some embodiments, the CRISPR/Cas system protein cleaved products are eliminated with the use of biotin. For example in a sample originally comprising <5% DNA of interest and >95% DNA targeted for depletion, the >95% DNA is fragmented and depleted, and the uncut (<5% DNA of interest) DNA comprises a biotin label is purified by binding to streptavidin beads. This example illustrates a method of removing unwanted DNA (depleted DNA fragmented) after CRISPR/Cas system protein-mediated cleavage without the use of an exonuclease.

Figure 10:
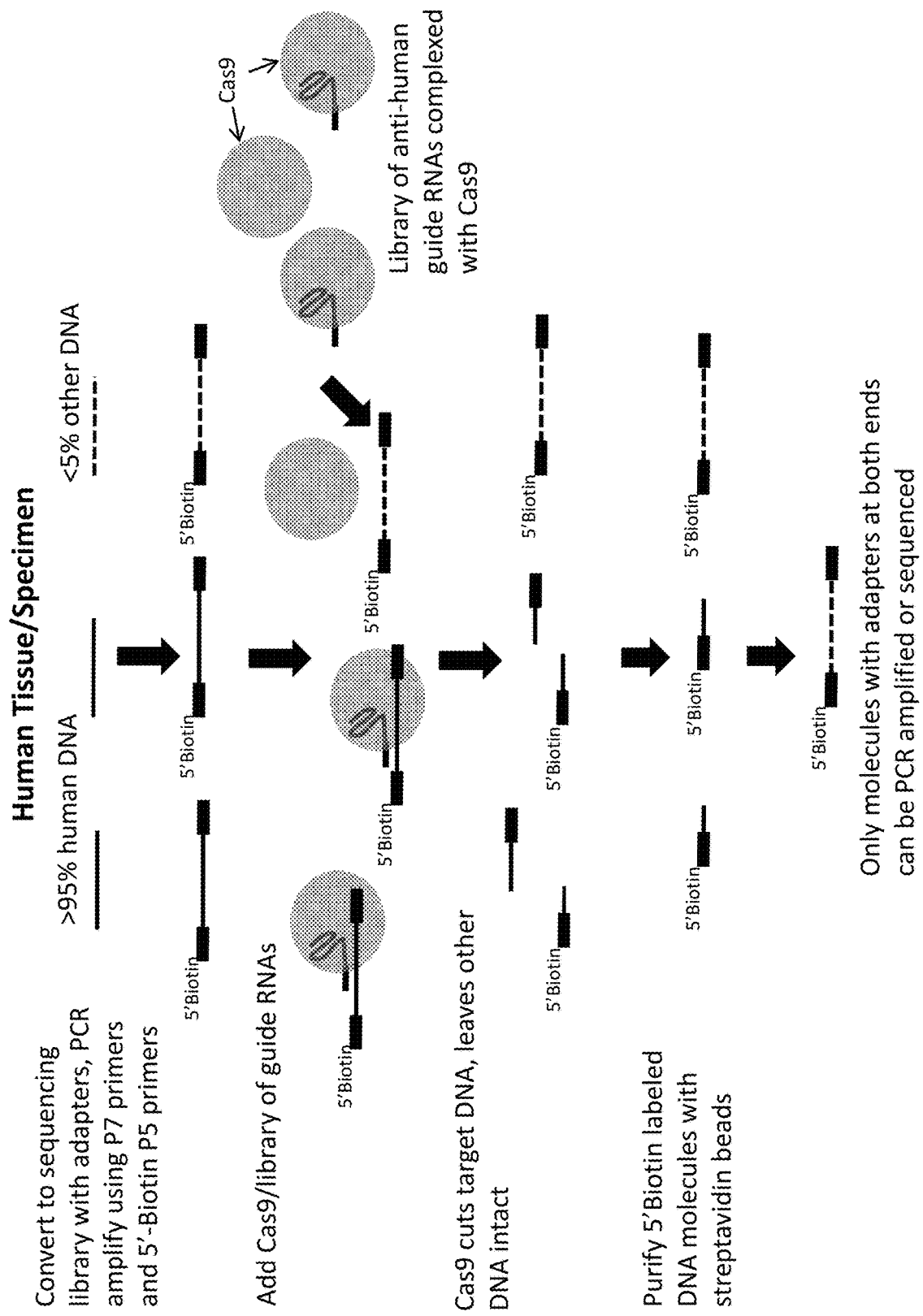
FIG. 10 illustrates biotin labeling during Cas-9 mediated depletion

An exemplary embodiment is depicted in FIG. 10. In this exemplary embodiment a DNA mixture (containing >95% unwanted human DNA, and <5% other DNA of interest) is fragmented, end-repaired and ligated to adapters following regular protocols, then amplified by PCR using primers of Biotin-P5, (for example 5'Biotin-AATGATACGGCGAC-CACCGA) and P7 (for example, 5'-CAAGCAGAA-GACGGCATACGA). This ensures that the entire sequencing library possesses a 5'Biotin label only on one end of the DNA molecules. The DNA mixture is then subjected to CRISPR/Cas system protein (for example, Cas9) digestion, complexed with, for example for this case, a guide RNA library against mitochondrial DNA (the unwanted DNA). DNA molecules that have been cleaved by the CRISPR/Cas system protein (for example in this case, mitochondrial DNA) will lose the Biotin labeled adaptor, and thus cannot be sequenced or PCR amplified; while intact DNA libraries uncut by Cas9 (for example in this case, non-mitochondrial DNA of interest) still carry the Biotin label. As a result, intact DNA uncut by the CRISPR/Cas system protein can then be recovered by adding streptavidin beads. Samples can then be subject to further downstream applications, such as sequencing, cloning, for further enrichment.

Exonuclease Treatment Following Depletion

In some embodiments, it is desirable to remove cut fragments prior to PCR amplification or sequencing.

In one embodiment, CRISPR/Cas system protein-mediated depletion is followed by an exonuclease treatment. The exonuclease treatment can further degrade a CRISPR/Cas system protein cleaved nucleic acid, while leaving the uncut nucleic acid comprising sequences of interest intact.

In one embodiment, a method of depleting targeted sequences in a sample comprises: providing a sample comprising sequences of interest and targeted sequences for depletion; contacting the sample with a plurality of CRISPR/Cas system protein-gRNA complexes, wherein the gRNAs are complementary to the targeted sequences, thereby generating cleaved targeted sequences; and contacting the product of step (b) with an exonuclease. In one embodiment the exonuclease is Exonuclease III. In another embodiment, the exonuclease is BAL-31.

Figure 8:
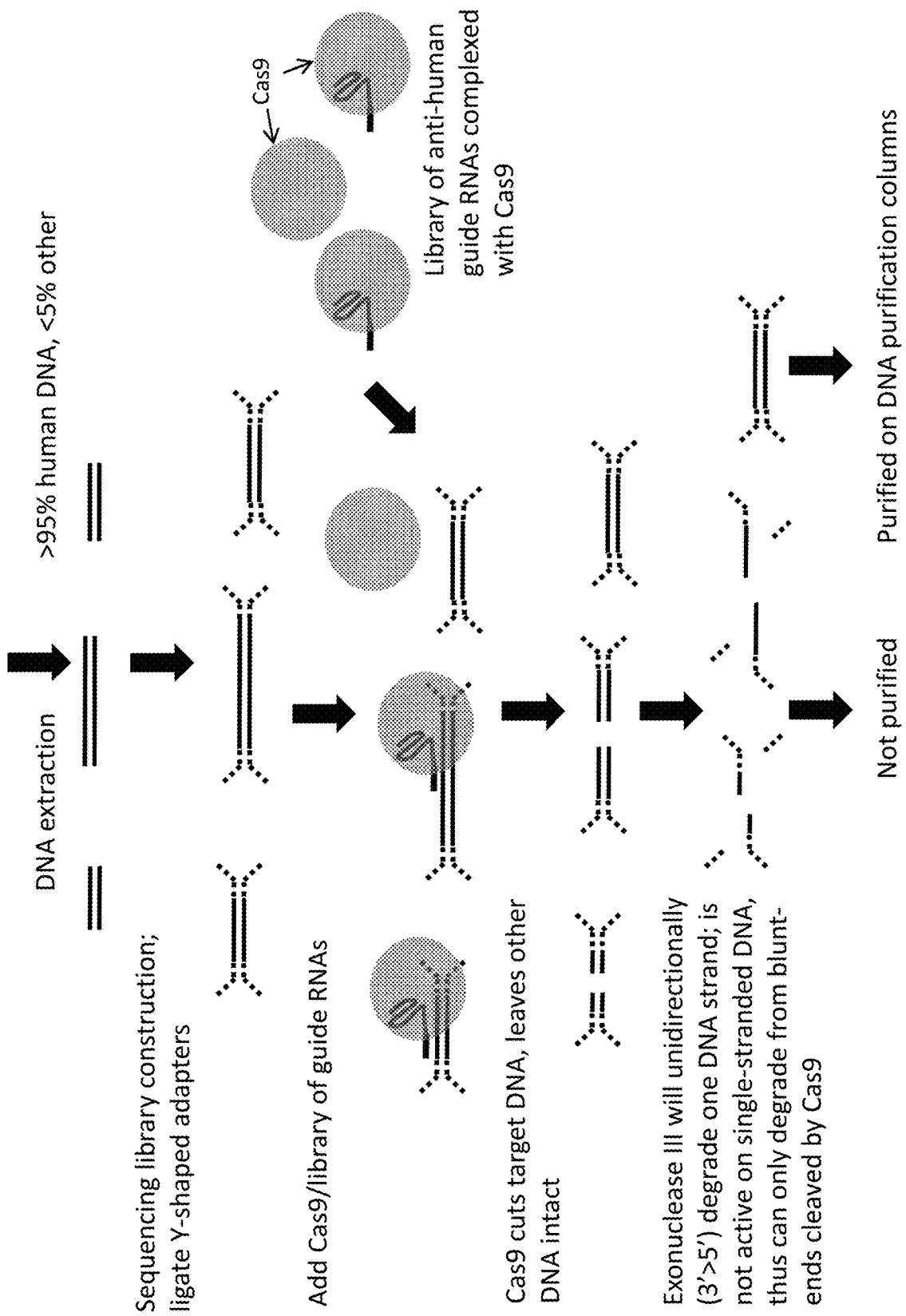
FIG. 8 illustrates Cas9-mediated depletion followed by Exonuclease III treatment.

In one exemplary embodiment, DNA is extracted from a biological sample and fragmented and a library, for example a sequencing library, comprising the fragments of DNA, is thus created. Y-shaped adapters or circular adapters are ligated to the DNA fragments. The DNA fragments comprise DNA sequences of interest, and targeted sequences (DNA not of interest). The library is contacted with a plurality of CRISPR/Cas system protein-gRNA complexes, and the CRISPR/Cas system protein cuts the target DNA not of interest and leaves the other DNA sequences of interest intact. The resulting products are contacted with Exonuclease III. Exonuclease III can initiate unidirectional 3'>5' degradation of one DNA strand by using blunt end or 5' overhangs, yielding single-stranded DNA and nucleotides; it is not active on single-stranded DNA, and thus 3' overhangs, such as the Y-shaped adapter ends, are resistant to degradation. As a result, intact double-stranded DNA libraries uncut by the CRISPR/Cas system protein is not digested by Exonuclease III, while DNA molecules that have been cleaved by the CRISPR/Cas system protein are degraded by Exonuclease III with its 3'>5' activity from the blunt ends cut by Cas9 towards the adaptors. FIG. 8 illustrates an exemplary embodiment. A DNA mixture (containing >95% unwanted human DNA, and <5% other DNA of interest is fragmented, end-repaired and ligated to Y-shaped adapters (or circular adapters) following regular protocols, but not amplified by PCR. The DNA mixture is then subjected to Cas9 digestion, complexed with, for example for this case, a guide RNA library against mitochondrial DNA. Exonuclease III is added. Unwanted mitochondrial DNA is digested. The remaining intact double-stranded DNA libraries are then recovered by column-purification and/or PCR-amplified.

Figure 9:
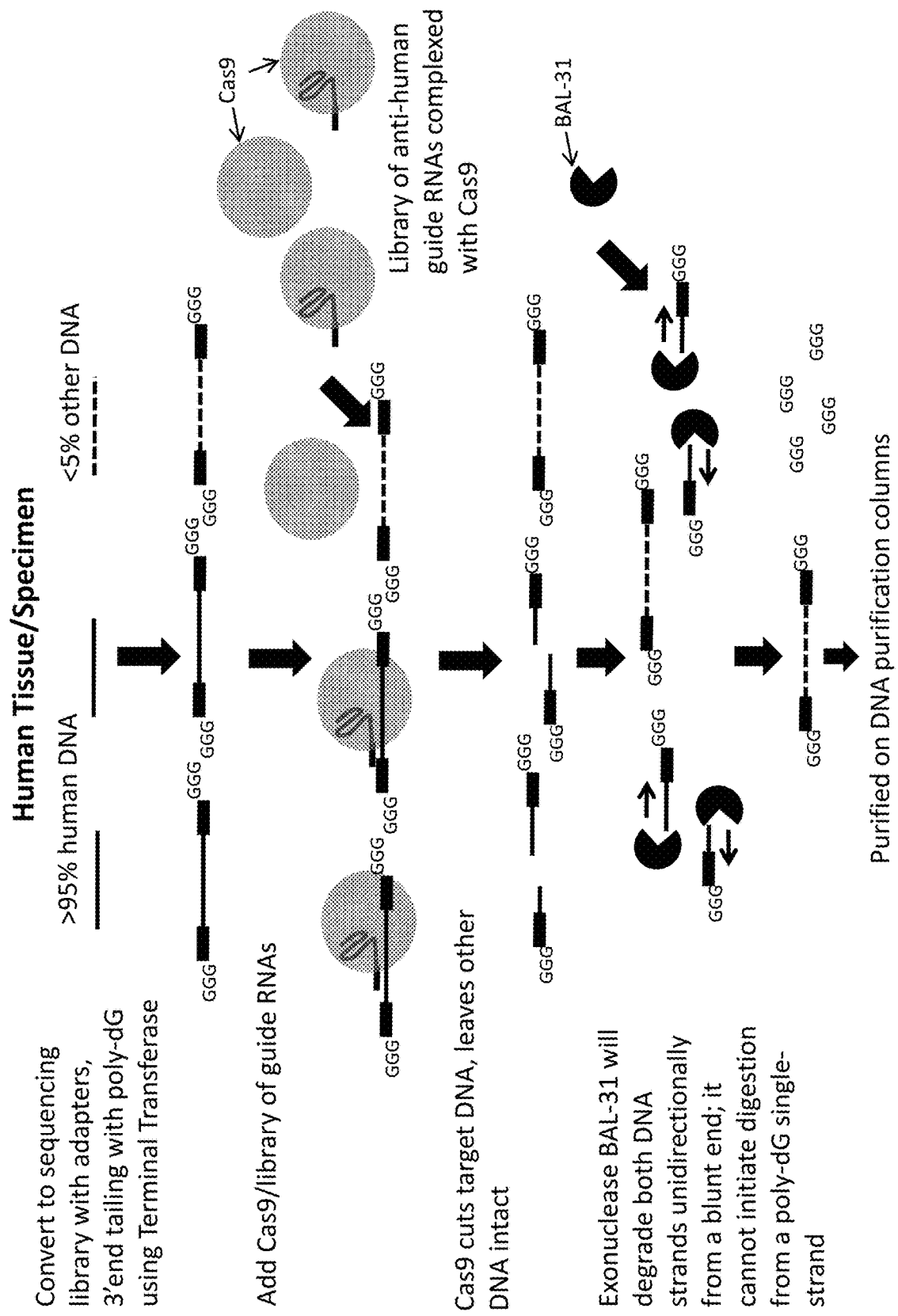
FIG. 9 illustrates Cas9-mediated depletion followed by Exonuclease Bal-31 treatment.

In another exemplary embodiment, Exonuclease BAL-31 is used degrade CRISPR/Cas system protein-cleaved DNA while leaving the uncut DNA of interest intact. In one exemplary embodiment, DNA is extracted from a biological sample and fragmented and a library, for example a sequencing library, comprising the fragments of DNA, is thus created. The DNA fragments comprise DNA sequences of interest, and targeted sequences (DNA not of interest). The 3' ends of the fragments are tailed with poly-dG using terminal transferase. The library is contacted with a plurality of CRISPR/Cas system protein-gRNA complexes, and the CRISPR/Cas system protein cuts the target DNA not of interest and leaves the other DNA sequences of interest intact. The resulting products are contacted with Exonuclease BAL-31. Exonuclease BAL-31 has two activities: double-stranded DNA exonuclease activity, and single-stranded DNA/RNA endonuclease activity. The double-stranded DNA exonuclease activity allows BAL-31 to degrade DNA from open ends on both strands, thus reducing the size of double-stranded DNA. The longer the incubation, the greater the reduction in size of the double-stranded DNA, making it useful for depleting medium to large DNA (>200 bp). It was noted that the single-stranded endonuclease activity of BAL-31 allows it to digest poly-A, -C or -T very rapidly, but is extremely low in digesting poly-G (Marrone and Ballantyne, 2008). Because of this nature, adding single-stranded poly-dG at 3' ends of the libraries serves as a protection from being degraded by BAL-31. As a result, DNA molecules that have been cleaved by a CRISPR/Cas system protein can be degraded by BAL-31 with its double-stranded DNA exonuclease activity from the double-stranded blunt end cut by the CRISPR/Cas system protein towards the other end carrying poly-dG, effecting depletion; while intact DNA libraries uncut by the CRISPR/Cas system protein are not digested by BAL-31 due to their 3' end poly-dG protection. FIG. 9 depicts an exemplary embodiment of this approach. Sequencing libraries (containing, for example >95% human DNA and <5% other are prepared. The libraries are tailed with poly-dG at 3' ends using Terminal Transferase. poly-dG tailed libraries are then subjected to Cas9 digestion, complexed with a guide RNA library, for example a guide RNA library against mitochondrial DNA. The products are then incubated with Exonuclease BAL-31, which initiates digestion of ends not capped by the poly-dG. The products are then subject to further PCR or purified on DNA purification columns. The remaining intact double stranded DNA libraries can then be recovered by column purification or PCR-amplified.

Controls for Monitoring Depletion

In the embodiments discussed, it is desirable to provide positive and/or negative controls. A positive control can ensure depletion of target nucleic acids proceeds with fidelity.

In some embodiments, a control set of reagents is a positive control set of reagents, positive control target sequences. In an exemplary embodiment, the positive control set of reagents comprise a collection of nucleic acid fragments, wherein the fragments comprise the target sequences, to which the gRNAs are at least 80%, at least 85%, at least 90%, at least 95%, at least 96%, at least 97%, at least 98%, at least 99%, or 100% complementary. This control could be run alongside a user's reaction to ensure that all components are working properly. After depletion with a CRISPR/Cas system protein, elimination of the positive control target sequences could be measured by gel electrophoresis or qPCR.

In some embodiments, the control set of reagents is a negative control set of reagents. In some embodiments a negative control ensures that off-target cutting is minimal or nonexistent. In an exemplary embodiment, the negative control set of reagents comprise a second set of gRNAs, wherein the second set of gRNAs exhibit reduced binding to the target sequences, as compared to the first set of gRNAs. In some embodiments, the second set of gRNAs exhibit 5%, 10%, 15%, 20%, 25%, 30%, 35%, 40%, 45%, 50%, 55%, 60%, 65%, 70%, 75%, 80%, or 85% reduced binding to the target sequences, as compared to the first set of RNAs. In another exemplary embodiment, the negative control set of reagents comprise a second set of gRNAs, wherein the second set of gRNAs are no more than 50%, 55%, 60%, 65%, 70%, 75%, 80%, 85%, 90%, or 95% complementary to target sequences. The negative control could be a set of gRNAs with less than 100% identity to the gRNAs used; for example, with 1, 2, 3, 4, 5, or more mismatches to the target-specific sequence. In some embodiments, the negative control set of reagents comprise a collection of nucleic acid fragments, wherein the fragments are no more than 50%, 55%, 60%, 65%, 70%, 75%, 80%, 85%, 90%, or 95% complementary to the first set of gRNAs. The DNA library could have with less than 100% identity to the targeted sequences of gRNAs used in the kit; for example, with 1, 2, 3, 4, 5, or more mismatches to the complementary sequence of the gRNA. This control could be run alongside a user's reaction to ensure that all components are working properly and to measure any off-target activity of the enzyme. After depletion with CRISPR/Cas system protein, the amount of off-target depletion can be measured by gel electrophoresis or qPCR.

With respect to the positive and negative controls contemplated herein, complementarity of the gRNA to its target as provided herein can refer to the complementarity of the gRNA along the entire length of the target. In some embodiments, however the complementarity may be more impacted by mismatches of nucleic acids at the terminal end of the gRNA, at the area binding closest to the PAM sequence. Mismatches in this region may impact the capacity to bind the target in a greater manner than mismatches of nucleic acids elsewhere along the gRNA. Likewise, mismatches in the gRNA further away from the PAM sequence may impact the capacity to bind the target less than mismatches of nucleic acids elsewhere along the gRNA. In some embodiments, the negative control gRNA has a lower complimentarily near the PAM sequence, but higher complementarity farther away from the PAM sequence. For example, in some embodiments, the negative control gRNA has 50%-70% complementarity near the PAM sequence, but 70%-100% complementarity farther away from the PAM sequence. In some embodiments, the negative control gRNA has 50%, 55%, 60%, 65%, 70%, 75%, 80%, 85%, 90%, or 95% complementarity along the entire length of the target.

Depleting Mitochondrial DNA Following ATAC-Seq

The Assay for Transposase-Accessible Chromatin Using Sequencing (ATAC-seq) technique is used in molecular biology to study chromatin, namely its accessible sites. The method is based on tagging open chromatin regions with sequencing adaptors by transposase, such that DNA fragments from these open chromatin regions can be amplified and subjected to high-throughput sequencing (WO2014/189957; Buenrostro et al., Nature Methods, Vol. 10, No. 12, December 2013, p. 1213). Although ATAC-seq requires much less starting material compared to other assays for genome-wide chromatin accessibility, one of the main drawbacks is that the sequencing library is often contaminated with high percentage of mitochondrial DNA (which is also open DNA), and requires many more sequencing reads for standard accessibility studies of the human genome, such as DNase-seq and FAIRE-seq (M. Tsompana and M J. Buck, 2014). Therefore there is a need in the art to remove unwanted mitochondrial DNA contamination from the sequencing library following an ATAC-Seq procedure, in order to decrease sequencing costs. The present disclosure provides a method to selectively deplete mitochondrial DNA from a sample that has undergone ATAC-Seq.

Provided herein is a method for analyzing genomic DNA, comprising: (a) treating DNA isolated from a population of cells with an insertional enzyme to produce a plurality of tagged fragments of non-mitochondrial genomic DNA, whereby also generating a residual amount of tagged mitochondrial DNA; (b) enriching the product of step (a) for non-mitochondrial DNA according to any of the enrichment or depletion methods provided herein. In some embodiments, the method further comprises sequencing at least some of the tagged fragments to produce a plurality of sequence reads; and making an epigenetic map of a region of the genome of said cells by mapping information obtained from the sequence reads to the region.

In another aspect, the present disclosure provides a method for assisting the determination of accessibility of a polynucleotide at a site, wherein the polynucleotide is from a cell sample, said method comprising: inserting a plurality of molecular tags with an insertional enzyme into the polynucleotide and using the molecular tags to determine accessibility at the site, and removing unwanted DNA contamination using the CRISPR/Cas system-based depletion methods described herein. The cell sample can be from a primary source. The cell sample may consist of a single cell. The cell sample may consist of a finite number of cells (e.g. less than about 500,000 cells).

The insertional enzyme can be any enzyme capable of inserting a nucleic acid sequence into a polynucleotide. In some cases, the insertional enzyme can insert the nucleic acid sequence into the polynucleotide in a substantially sequence-independent manner. The insertional enzyme can be prokaryotic or eukaryotic. Examples of insertional enzymes include, but are not limited to, transposases, HERMES, and HIV integrase. The transposase can be a Tn transposase (e.g. Tn3, Tn5, Tn7, Tn10, Tn552, Tn903), a MuA transposase, a Vibhar transposase (e.g. from Vibrio harveyi), Ac-Ds, Ascot-I, BsI, Cin4, Copia, En/Spm, F element, hobo, Hsmar1, Hsmar2, IN (HIV), ISI, IS2, IS3, IS4, IS5, IS6, ISIO, IS2I, IS30, IS50, ISSI, ISI50, IS256, IS407, IS427, IS630, IS903, IS911, IS982, IS103I, ISL2, LI, Mariner, P element, Tam3, Tel, Tc3, Tel, THE-I, Tn/O, TnA, Tn3, Tn5, Tn7, TnlO, Tn552, Tn903, Toll, Tol2, TnlO, Tyl, any prokaryotic transposase, or any transposase related to and/or derived from those listed above. In certain instances, a transposase related to and/or derived from a parent transposase can comprise a peptide fragment with at least about 50%, about 55%, about 60%, about 65%, about 70%, about 75%, about 80%, about 85%, about 90%, about 91%, about 92%, about 93%, about 94%, about 95%, about 96%, about 97%, about 98%, or about 99% amino acid sequence homology to a corresponding peptide fragment of the parent transposase. The peptide fragment can be at least about 10, about 15, about 20, about 25, about 30, about 35, about 40, about 45, about 50, about 60, about 70, about 80, about 90, about 100, about 150, about 200, about 250, about 300, about 400, or about 500 amino acids in length. For example, a transposase derived from Tn5 can comprise a peptide fragment that is 50 amino acids in length and about 80% homologous to a corresponding fragment in a parent Tn5 transposase. In some cases, the insertion can be facilitated and/or triggered by addition of one or more cations. The cations can be divalent cations such as, for example, $Ca^{2+}$, $Mg^{2+}$ and $Mn^{2+}$.

The molecular tags can comprise sequencing adaptors, locked nucleic acids (LNAs), zip nucleic acids (ZNAs), RNAs, affinity reactive molecules (e.g. biotin, dig), self-complementary molecules, phosphorothioate modifications, azide or alkyne groups. In some cases, the sequencing adaptors can further comprise a barcode label. Further, the barcode labels can comprises a unique sequence. The unique sequences can be used to identify the individual insertion events. Any of the tags can further comprise fluorescence tags (e.g. fluorescein, rhodamine, Cy3, CyS, thiazole orange, etc.).

Kits and Articles of Manufacture

The present application provides kits comprising any one or more of the compositions described herein, not limited to adapters, gRNAs, gRNA libraries, and the like.

In one embodiment, the kit comprises a collection or library of gRNAs wherein the gRNAs are targeted to human DNA sequences. In another embodiment, the kit comprises a collection or library of gRNAs wherein the gRNAs are targeted to bovine DNA sequences. In another embodiment, the kit comprises a collection or library of gRNAs wherein the gRNAs are targeted to human ribosomal RNA sequences. In another embodiment, the kit comprises a collection or library of gRNAs wherein the gRNAs are targeted to human mitochondrial DNA sequences.

In some embodiments, the kit comprises: a CRISPR/Cas system protein and gRNAs, wherein the gRNAs are complementary to mitochondrial DNA; or wherein the gRNAs are complementary to the entire genome; or the wherein the gRNAs are complementary to a cDNA made from a whole transcriptome; or wherein the gRNAs are complementary to cDNA made form at least 10, at least 25, at least 50, at least 100, at least 250, at least 500, at least 750, at least $10^2$, at least $10^3$, at least $10^4$, at least $10^5$, at least $10^6$, at least $10^7$, at least $10^8$, at least $10^9$, at least $10^{10}$ unique transcripts; or wherein the gRNAs are complementary to cDNA made from the most abundant transcripts in a transcriptome, for example the most abundant 100, 75, 50, 25, 20, 15, or 10 transcripts in a transcriptome; or wherein the gRNAs are complementary to cDNA made from a subset of the most abundant 100, 75, 50, 25, 20, 15, or 10 transcripts in a transcriptome.

In some embodiments, the kit comprises: a CRISPR/Cas system protein and gRNAs, wherein the CRISPR/Cas system protein comprises a mixture of CRISPR/Cas system proteins from different bacteria; or wherein the CRISPR/Cas system protein is engineered; wherein the gRNAs are complementary to mitochondrial DNA; or wherein the gRNAs are complementary to genomic DNA, representing the entire genome; or wherein the gRNAs are complementary to cDNA libraries derived from the whole transcriptome; or wherein the gRNAs are complementary to cDNA libraries derived from at least 10, at least 25, at least 50, at least 100, at least 250, at least 500, at least 750, at least $10^2$, at least $10^3$, at least $10^4$, at least $10^5$, at least $10^6$, at least $10^7$, at least $10^8$, at least $10^9$, at least $10^{10}$ unique transcripts; or wherein the gRNAs are complementary to the cDNA libraries derived from the most abundant 100, 75, 50, 25, 20, 15, or 10 transcripts in a transcriptome; or wherein the gRNAs are complementary to the cDNA libraries derived from a subset of the most abundant 100, 75, 50, 25, 20, 15, or 10 transcripts in a transcriptome; or wherein the gRNAs comprise a mixture of gRNAs capable of targeting a CRISPR/Cas system protein from different bacterial species to the target sequences.

In some embodiments, the kit comprises: a CRISPR/Cas system protein; gRNAs, wherein the gRNAs are complementary to a target of interest; and an enzyme having exonuclease activity. In one embodiment, the exonuclease is Exonuclease III. In one embodiment, the exonuclease is BAL-31.

In some embodiments, the kit comprises: a CRISPR/Cas system protein, wherein the CRISPR/Cas system protein is thermostable; and gRNAs, wherein the gRNAs are complementary to a target of interest.

In some embodiments, the kit comprises: a CRISPR/Cas system protein; and a first set of gRNAs, wherein the gRNAs are complementary to target sequences of interest; and a control set of reagents. In one embodiment, the control set of reagents is a positive control set of reagents. In an exemplary embodiment, the positive control set of reagents comprise a collection of nucleic acid fragments, positive control target sequences, wherein the fragments comprise the target sequences, to which the gRNAs are complementary. In one embodiment, the control set of reagents is a negative control set of reagents. In an exemplary embodiment, the negative control set of reagents comprise a second set of gRNAs, wherein the second set of gRNAs exhibit reduced binding to the target sequences, as compared to the first set of gRNAs. In another exemplary embodiment, the negative control set of reagents comprise a collection of nucleic acid fragments, wherein the fragments are no more than 90% complementary to the first set of gRNAs.

In some embodiments, the kit comprises: reagents for isolating DNA from a population of cells; an insertional enzyme; a CRISPR/Cas system protein; and a plurality of gRNAs, wherein the gRNAs are complementary to mitochondrial DNA; or wherein the gRNAs are complementary to the entire genome; or the wherein the gRNAs are complementary to the whole transcriptome; or wherein the gRNAs are complementary to the top 100, 75, 50, 25, 20, 15, or 10 genes in a transcriptome.

The present application also provides articles of manufacture comprising any one of the kits described herein. Examples of an article of manufacture include vials (including sealed vials).

The following examples are included for illustrative purposes and are not intend to limit the scope of the invention.

EXAMPLES

Example 1

Depletion of Mitochondrial DNA from ATAC-Seq Libraries, Library 1

Overview

Figure 4:
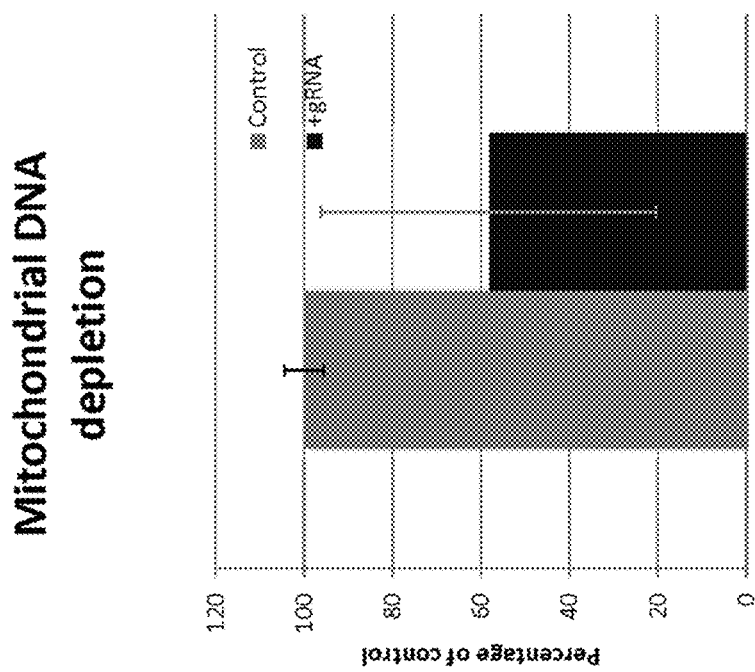
FIG. 4 illustrates the results of a depletion experiment in which mitochondrial DNA was depleted by ~44% (measured by qPCR).

As depicted in FIG. 4, the depletion method was tested on a human DNA library, which has been previously sequenced and shown to consist of 94% human nuclear DNA and 6% mitochondrial DNA (Library 1). Depletion was performed using recombinant Cas9 and a library of 25 guide RNAs specifically designed for mitochondrial DNA. A control depletion was performed using an unrelated guide RNA that does not target mitochondrial DNA. About 40% of the human mitochondrial DNA was depleted. The depletion was completed in 20 minutes, followed by PCR to amplify the library.

Expression of Cas9

Cas9 (from *S. pyogenes*) was cloned into the pET30 expression vector (EMD biosciences) to insert the hexahistidine tag immediately upstream of the Cas9 start codon. The resulting plasmid was transformed into the Rosetta (DE3) BL21 bacterial strain (EMD biosciences) and grown in 1L of LB media with vigorous aeration until optical density of the culture (OD at 600 nm) reached 0.4. The temperature was lowered to 25° C., 0.2 mM IPTG was added and the culture grown for another four hours. Cells were then harvested by centrifugation (1,000×g for 20 min at 4° C.), resuspended in 10 ml binding buffer (20 mM Tris pH8, 0.5 M NaCl, 5 mM Imidazole, 0.05% NP40) and lysed by sonication (7×10 second bursts at 30% power, Sonifier 250, Branson). Insoluble cell debris were removed by centrifugation at 10,000×g for 20 min; supernatant containing soluble protein was then mixed with 0.4 ml of NTA beads (Qiagen) and loaded onto a column. Beads were washed three times with 4 ml binding buffer, then eluted with 3×0.5 ml of binding buffer supplemented with 250 mM Imidazole. Eluted fractions were then concentrated and buffer exchanged with storage buffer (10 mM Tris pH8, 0.3 M NaCl, 0.1 mM EDTA, 1 mM DTT, 50% glycerol) using a 30,000 MWCO protein concentrator (Life Technologies), verified by SDS PAGE followed by Colloidal Blue staining (Life Technologies), quantified, then stored at −20° C. for later use.

A mutant Cas9 nickase, a D10A mutant of *S. pyogenes* Cas9, was produced and purified using the same procedures used to produce Cas9 as above.

Preparation of Guide RNA Libraries

Twenty-five constructs were designed with each one containing the T7 RNA polymerase promoter, 20 base pairs of mitochondrial DNA specific sequence, and the guide RNA scaffold from *S. pyogenes*. For each construct two oligonucleotides were ordered (see Tables 1 and 2 for sequences) and combined at 1 µM final concentration in 5 µl, then heated at 98° C. for 3 minutes, then cooled at a rate of 5° C./minute to 55° C., and finally incubated at 55° C. for 5 minutes.

Annealed oligos were then ligated to the T7GRNE vector which contains the guide RNA scaffold by golden gate cloning; annealed oligos were combined to 500 ng of T7GRNE plasmid, 1 µl of BsaI restriction enzyme and 1 µl of T7 DNA ligase in a total volume of 20 µl. Reactions were incubated in a thermal cycler for 10 cycles of 37° C. for 15 minutes followed by 20° C. for 10 minutes, followed by a single cycle at 80° C. for 15 minutes. Products were then PCR amplified using the specific forward primer (see Tables 1 and 2) and the reverse primer (5'-CAGAGCGAGGTATGTAGG-3'). Cycling conditions were as follows: 30 cycles of 95° C. for 1 min, 57° C. for 30 s, and 72° C. for 90 s. Successful reactions were confirmed by the presence of a 1.6 kb fragment by agarose gel electrophoresis and SYBR safe staining. Successful reactions were pooled together and purified using a PCR cleanup kit (Thermo Fisher Scientific).

Guide RNAs were designed using the following rules:

Rule 1: Found the following sequence (5'>3' direction) in the genomic region of interest (for example the entire exome or mitochondrial genome) on any strand:

<u>NNNNNNNNNNNNNNNNNNNN</u>GG

Rule 2: Underlined sequence (20-mer) is the targeting part of guide RNA included in the oligonucleotide ordered.
  a. Eliminated any 20-mer that has more than 55% GC content
  b. Eliminated any 20-mer that has more than 13 stem loop forming base pairs (predicted for example, by either Mfold or Vienna softwares)
  c. If first nucleotide of 20-mer is not A/G, then one G residue was added at 5' end to yield a 21-mer
  d. Rule 3: Added the T7 promoter and primer binding site to yield the following primer (5'>3'):

GCCTCGAGCTAATACGACTCACTATAG(G)
<u>NNNNNNNNNNNNNNNNNNNN</u>

(G) indicates the G to be added if the 20-mer does not have a purine at the 5'end In Vitro Transcription To transcribe the guide libraries into guide RNA, we assembled the following in vitro transcription reaction mixture: 10 µl purified library (~500 ng), 6.5 µl of H2O, of 2.25 µl of ATP, 2.25 µl of CTP, 2.25 µl of GTP, 2.25 µl of UTP, 2.25 µl 10× reaction buffer (NEB) and 2.25 µl of T7 RNA polymerase mix. The reaction was incubated at 37° C. for 24 hours, then diluted 10-fold in H2O. A single reaction produced ~40 µg of RNA. The yield and size of the RNA (~150 base pairs) was checked by running 1 µl of the reaction on a 5% TBE/Urea gel and staining with SYBR Gold (Life Technologies).

DNA-Specific Cas9-Mediated Depletion

Diluted guide RNA (1 µl, equivalent to 2 pmol) was combined with 3 µl 10× Cas9 reaction buffer (NEB), 20 µl H2O and 1 µl of recombinant Cas9 enzyme (NEB, 1 pmol/µl). A control reaction using a control guide RNA targeting the following sequence (5'-GGATTTATA-CAGCACTTTAA-3') was performed separately, using the same parameters. This sequence is absent from either the human chromosomal or mitochondrial DNA. Reactions were incubated for 15 min at 37° C., then supplemented with 5 µl diluted DNA library (50 pg/µl) and incubation at 37° C. continued for 90 min. The reactions were terminated by adding RNase A (Thermo Fisher Scientific) at a 1:100 dilution, heating to 98° C. for 5 min, then cooling to room temperature and adding 100 µl H2O. Reactions were then stored at −20° C. until use.

Quantification of Mitochondrial DNA after Depletion

For each reaction (each test condition and the reaction using the control guide RNA) two separate 5 µl samples were analyzed by real time PCR using both control and test primers. For control primers reactions, samples were incubated with 2 µl H2O, 0.25 µl of 10 µM primer P5 (5'-AATGATACGGCGACCACCGA-3'), and 0.25 µl of 10 µM P7, (5'-CAAGCAGAAGACGGCATACGA-3') and 7.5 µl of 2× Maxima SYBR Green master mix (Thermo Fisher Scientific). For test primers reactions, samples were incubated with 1.75 µl H2O, 0.5 µl of 10 µM mitochondrial primers (see tables 1 and 2), and 0.25 µl of 10 µM P7, (5'-CAAGCAGAAGACGGCATACGA-3') and 7.5 µl of 2× Maxima SYBR Green master mix (Thermo Fisher Scientific). Reactions were incubated in an iCycler real-time PCR thermal cycler (BioRad) using the following 2-step cycling conditions: 95° C. for 3 min, followed by 40 cycles of 95° C. for 10 s, 55° C. for 45 s.

For the two real time PCR conditions, using control and test primers, a calibration curve was performed. The diluted DNA library (50 µg/µl) was further diluted 1:10, 1:100,1:1000, 1:10,000 and these dilutions were analyzed by real time PCR using the same reaction conditions, instrument and cycling conditions described above.

The amount of total DNA and mitochondrial DNA was deduced from the results of the control and test primers reactions, respectively. For each DNA library depletion experiment, the ratio of mitochondrial DNA:total DNA was determined and normalized to the experiment using the control guide RNA, then plotted as a column graph shown in FIG. 4.

TABLE 2

| Forward primers-used in both the annealing and subsequent PCR reactions | |
|---|---|
| Oligo Name | Sequence |
| T7-13-F | GCC TCG AGC TAA TAC GAC TCA CTA TAG GCT CTT AAA ACT AGG CGG CTA G |
| T7-39-F | GCC TCG AGC TAA TAC GAC TCA CTA TAG ATT TAC ACT CAC AAC ACC CTG |
| T7-41-F | GCC TCG AGC TAA TAC GAC TCA CTA TAG AAC AGC TAT CCA TTG GTC TTG |
| T7-43-F | GCC TCG AGC TAA TAC GAC TCA CTA TAG GCA GCC GGA AGC CTA TTC GCG |

TABLE 2

| Forward primers-used in both the annealing and subsequent PCR reactions | |
|---|---|
| Oligo Name | Sequence |
| T7-61-F | GCC TCG AGC TAA TAC GAC TCA CTA TAG GTA ATG AGG ATG TAA GCC CGG |
| T7-63-F | GCC TCG AGC TAA TAC GAC TCA CTA TAG ATA TTT ACA AGA GGA AAA CCG |
| T7-65-F | GCC TCG AGC TAA TAC GAC TCA CTA TAG GTT TGA AGC TTA GGG AGA GCT G |
| T7-67-F | GCC TCG AGC TAA TAC GAC TCA CTA TAG GTA TGG CTT TGA AGA AGG CGG |
| T7mtgRNA3 | GCC TCG AGC TAA TAC GAC TCA CTA TAG TAG ATG ACG GGT TGG GCC AGG |
| T7mtgRNA7 | GCC TCG AGC TAA TAC GAC TCA CTA TAG AGC TTT ACA GTG GGC TCT AGG |
| T7mtgRNA11 | GCC TCG AGC TAA TAC GAC TCA CTA TAG ATG GCA GCT TCT GTG GAA CGG |
| T7mtgRNA15 | GCC TCG AGC TAA TAC GAC TCA CTA TAG GTG GTA AGG GCG ATG AGT GTG |
| T7mtgRNA31 | GCC TCG AGC TAA TAC GAC TCA CTA TAG TCC ATA ACG CTC CTC ATA CTG |
| T7mtgRNA33 | GCC TCG AGC TAA TAC GAC TCA CTA TAG TCT CCC TTC ACC ATT TCC GAG |
| T7mtgRNA35 | GCC TCG AGC TAA TAC GAC TCA CTA TAG GCC TAT GAG TGA CTA CAA AAG |
| T7mtgRNA37 | GCC TCG AGC TAA TAC GAC TCA CTA TAG CTT TGC CGC CTG CGA AGC AGG |
| T7mtgRNA57 | GCC TCG AGC TAA TAC GAC TCA CTA TAG ATG TCT CCA TCT ATT GAT GAG |
| T7mtgRNA79 | GCC TCG AGC TAA TAC GAC TCA CTA TAG GGA GGC CTG CCC CCG CTA ACG |
| T7mtgRNA81 | GCC TCG AGC TAA TAC GAC TCA CTA TAG CGA GCC GAG CTG GGC CAG CCG |
| T7mtgRNA83 | GCC TCG AGC TAA TAC GAC TCA CTA TAG GCG AGC AGG AGT AGG AGA GAG |
| T7mtgRNA85 | GCC TCG AGC TAA TAC GAC TCA CTA TAG CAA CAC TTT CTC GGC CTA TCG |
| T7mtgRNA87 | GCC TCG AGC TAA TAC GAC TCA CTA TAG ACT TTG ACA AAG TTA TGA AAG |
| T7mtgRNA89 | GCC TCG AGC TAA TAC GAC TCA CTA TAG TCA AAT CAA TTG GCC ACC AAG |
| T7mtgRNA91 | GCC TCG AGC TAA TAC GAC TCA CTA TAG ACT CAT TCA ACC AAT AGC CCG |
| T7mtgRNA93 | GCC TCG AGC TAA TAC GAC TCA CTA TAG GTG CTC ACA CGA TAA ACC CTG |

| Reverse primers-used during the anneal reaction and the real time PCR reactions | |
|---|---|
| Oligo Name | Sequence |
| mtgRNA2 | aaaacTTCTAAACGCTAATCCAAGCct |
| mtgRNA14 | aaaacTAGCCGCCTAGTTTTAAGAGct |
| mtgRNA40 | aaaacAGGGTGTTGTGAGTGTAAATct |
| mtgRNA42 | aaaacAAGACCAATGGATAGCTGTTct |
| mtgRNA44 | aaaacGCGAATAGGCTTCCGGCTGCct |
| mtgRNA62 | aaaacCGGGCTTACATCCTCATTACct |
| mtgRNA64 | aaaacGGTTTTCCTCTTGTAAATATct |
| mtgRNA66 | aaaacAGCTCTCCCTAAGCTTCAAAct |
| mtgRNA68 | aaaacCGCCTTCTTCAAAGCCATACct |
| mtgRNA4 | aaaacCTGGCCCAACCCGTCATCTAct |
| mtgRNA8 | aaaacCTAGAGCCCACTGTAAAGCTct |
| mtgRNA12 | aaaacCGTTCCACAGAAGCTGCCATct |
| mtgRNA16 | aaaacACACTCATCGCCCTTACCACct |
| mtgRNA32 | aaaacAGTATGAGGAGCGTTATGGACct |
| mtgRNA34 | aaaacTCGGAAATGGTGAAGGGAGAct |
| mtgRNA36 | aaaacTTTTGTAGTCACTCATAGGCct |
| mtgRNA38 | aaaacCTGCTTCGCAGGCGGCAAAGct |
| mtgRNA58 | aaaacTCATCAATAGATGGAGACATct |
| mtgRNA80 | aaaacGTTAGCGGGGCAGGCCTCCt |
| mtgRNA82 | aaaacGGCTGGCCCAGCTCGGCTCGct |
| mtgRNA84 | aaaacTCTCTCCTACTCCTGCTCGCct |
| mtgRNA86 | aaaacGATAGGCCGAGAAAGTGTTGct |
| mtgRNA88 | aaaacTTTCATAACTTTGTCAAAGTct |
| mtgRNA90 | aaaacTTGGTGGCCAATTGATTTGAct |
| mtgRNA92 | aaaacGGGCTATTGGTTGAATGAGTct |
| mtgRNA94 | aaaacAGGGTTTATCGTGTGAGCACct |

Example 2

Depletion of Mitochondrial DNA from ATAC-seq Libraries, Library 2

Overview

Figure 5:
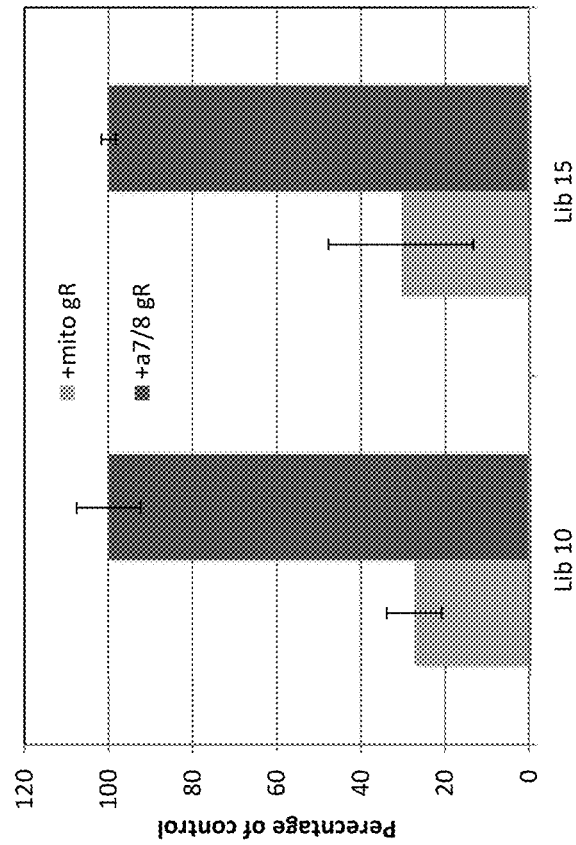
FIG. 5 illustrates the results of a second experiment in which a higher number of guide RNAs was used and mitochondrial DNA was depleted by ~70% (measured by qPCR).
Figure 6A:
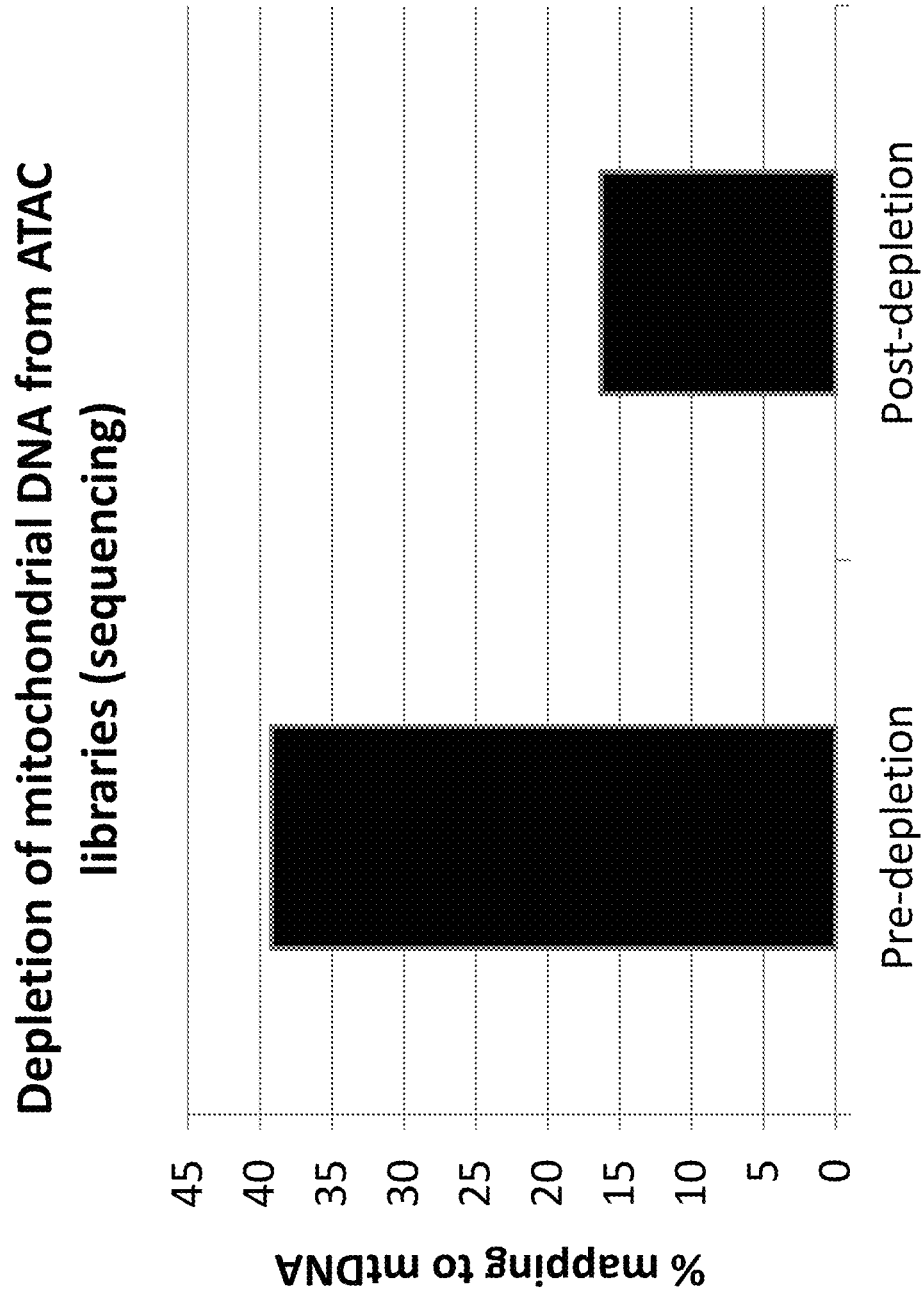
FIG. 6A illustrates the results of sequencing a library before and after depletion of mitochondrial DNA.
Figure 6B:
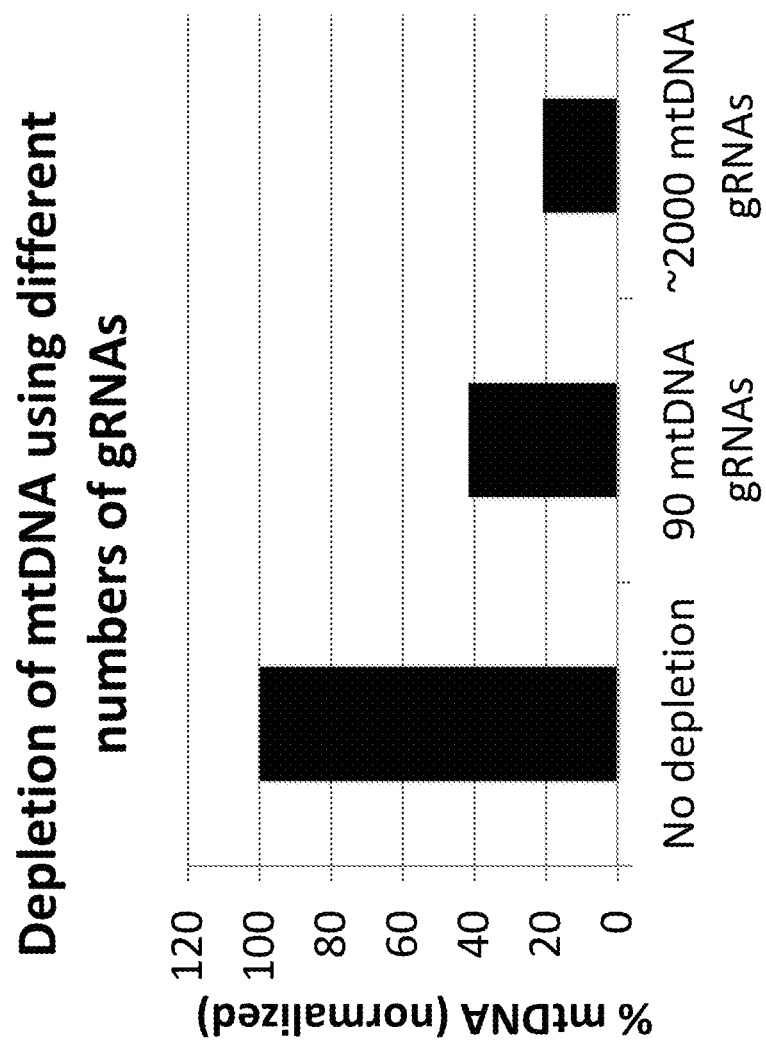
FIG. 6B illustrates depletion of mitochondrial DNA using different numbers of gRNAs.

As depicted in FIGS. 5 and 6, the depletion method was tested on a human DNA library, which has been previously sequenced and shown to consist of 55% human nuclear DNA and 45% mitochondrial DNA (Library 2). Depletion was performed using recombinant Cas9 and a library of 90 guide RNAs specifically designed for mitochondrial DNA, no gaps in the mitochondrial genome were left. A control depletion was performed using an unrelated guide RNA that does not target mitochondrial DNA.

The pre- and post-capture libraries were quantified by real time PCR using two different sets of primers: P5 with P7, which amplifies all DNA library fragments or mitochondrial DNA specific primers which only amplify mitochondrial DNA. The ratio of these two separate reactions was used to quantify the depletion of mitochondrial DNA The pre- and post-capture libraries were also sequenced on an Illumina MiSeq platform, and the resulting reads were mapped to the human genome to determine mitochondrial DNA content.

Expression of Cas9

Cas9 (from *S. pyogenes*) was cloned into the pET30 expression vector (EMD biosciences) to insert the hexahistidine tag immediately upstream of the Cas9 start codon. The resulting plasmid was transformed into the Rosetta (DE3) BL21 bacterial strain (EMD biosciences) and grown in 1L of LB media with vigorous aeration until optical density of the culture (OD at 600 nm) reached 0.4. The temperature was lowered to 25° C., 0.2 mM IPTG was added and the culture grown for another four hours. Cells were then harvested by centrifugation (1,000×g for 20 min at 4° C.), resuspended in 10 ml binding buffer (20 mM Tris pH8, 0.5 M NaCl, 5 mM Imidazole, 0.05% NP40) and lysed by sonication (7×10 second bursts at 30% power, Sonifier 250, Branson). Insoluble cell debris were removed by centrifugation at 10,000×g for 20 min; supernatant containing soluble protein was then mixed with 0.4 ml of NTA beads (Qiagen) and loaded onto a column. Beads were washed three times with 4 ml binding buffer, then eluted with 3×0.5 ml of binding buffer supplemented with 250 mM Imidazole. Eluted fractions were then concentrated and buffer exchanged with storage buffer (10 mM Tris pH8, 0.3 M NaCl, 0.1 mM EDTA, 1 mM DTT, 50% glycerol) using a 30,000 MWCO protein concentrator (Life Technologies), verified by SDS PAGE followed by Colloidal Blue staining (Life Technologies), quantified, then stored at −20° C. for later use.

A mutant Cas9 nickase, a D10A mutant of *S. pyogenes* Cas9, was produced and purified using the same procedures used to produce Cas9 as above.

Preparation of Guide RNA Libraries

T7-guideRNA oligonucleotides (Table 3) and a separate oligonucleotide, stlgR (sequence, GT TTT AGA GCT AGA AAT AGC AAG TTA AAA TAA GGC TAG TCC GTT ATC AAC TTG AAA AAG TGG CAC CGA GTC GGT GCT TTT TTT GGA TCC GAT GC) were ordered and synthesized (IDT).

The stlgR oligonucleotide (300 pmol) was sequentially 5' phosphorylated using T4 PNK (New England Biolabs) and then 5' adenylated sing the 5'adenylation kit (New England Biolabs), according to the manufacturer's instructions. T7-guide RNAs oligonucleotides (5 pmol) and the 5'adenylated stlgR (10 pmol) were then ligated using thermostable 5'App DNA/RNA ligase (New England Biolabs) at 65C for one hour. Ligation reactions were heat inactivated at 90° C. for 5 min, then amplified by PCR (using OneTaq, New England Biolabs, 30 cycles of 95° C. 30 secs, 57° C. 20 secs, 72° C., 20 secs) with primers ForT7 (sequence GCC TCG AGC TAA TAC GAC TCA C) and gRU (sequence AAAAAAAGCACCGACTCGGTG). PCR products were purified using PCR cleanup kit (Life Technologies) and verified by agarose gel electrophoresis and sequencing.

Verified products were then used as templates for in vitro transcription reactions using the HiScribe T7 transcription kit (New England Biolabs). 500-1000 ng of template was incubated overnight at 37° C. according to the manufacturer's instruction. The resulting guide RNA(s) was purified using the RNA cleanup kit (Life Technologies), eluted into 100 μl of RNase-free water, quantified and stored at −20° C. until use.

In Vitro Transcription

To transcribe the guide libraries into guide RNA, we assembled the following in vitro transcription reaction mixture: 10 μl purified library (~500 ng), 6.5 μl of H2O, of 2.25 μl of ATP, 2.25 μl of CTP, 2.25 μl of GTP, 2.25 μl of UTP, 2.25 μl 10× reaction buffer (NEB) and 2.25 μl of T7 RNA polymerase mix. The reaction was incubated at 37° C. for 24 hours, then diluted 10-fold in H2O. A single reaction produced ~40 μg of RNA. The yield and size of the RNA (~150 base pairs) was checked by running 1 μl of the reaction on a 5% TBE/Urea gel and staining with SYBR Gold (Life Technologies).

DNA-Specific Cas9-Mediated Depletion

Multiple guide RNAs (from single or multiple in vitro transcription reactions) were selected to ensure that >95% of target DNA to be depleted contained at least one guide RNA target sequence. This can be computed by measuring the distribution of library size and determining the mean, N and the standard deviation SD; N-2SD=minimum size for >95% of the library, ensuring that there is one guide RNA per this size to ensure >95% depletion. This can also be described as the Maximum distance between guide RNAs=Mean of library size−2×(standard deviation of library size). In the case of the mitochondrial library, the library contains DNA fragments that are 450 base pairs in average length, with a standard deviation of 100. This results in 250 bp between guide RNAs at a maximum. Here, the DNA fragments in these libraries are 450 bp in average length (with an estimated standard deviation of 100 bp), <5% of DNA is smaller than 250 bp assuming a normal distribution. Assuming guide RNAs will target 100% of their assigned targets, >95% of target DNA should contain at least one guide RNA site and be depleted.

In this example, all guides constructed in example 2 in addition to those constructed in example 1 were used. These multiple guide RNAs were mixed in equimolar amounts to add to 80 pmol total, then combined with 40 pmol purified Cas9 protein in 60 μl Cas9 reaction buffer (20 mM HEPES pH 6.5, 100 mM NaCl, 5 mM MgC12, 0.1 mM EDTA) and incubated for 10 min at 37° C. 5 ng of DNA mixture (containing the desired DNA and the target DNA to be depleted) was added and the incubation continued for another 20 min. The reaction was stopped by adding 140 μl of TE buffer (10 mM Tris pH 8, 1 mM EDTA) containing 2 μg/ml RNase A and incubating for 20 min at 37° C. DNA was recovered using the PCR cleanup kit (Life Technologies) without any addition of isopropanol prior to column binding, and eluted in 20 μl of 10 mM Tris pH 8. Eluted DNA was re-amplified using the HiFidelity master mix (New England Biolabs) according to the manufacturer's instructions, with the appropriate primers (for example P5 and P7 for re-amplifying Illumina based DNA sequencing libraries) and for 8-13 cycles of PCR.

Sequencing and Bioinformatics

PCR products were purified using the PCR cleanup kit and used as templates for high-throughput DNA sequencing (Illumina MiSeq or NextSeq).

Fastq files were aligned to the human genome reference (hg20) using bwa or bowtie to determine proportions of reads mapping to the nuclear vs. mitochondrial genomes.

TABLE 3

Additional guide RNAs used in Example 2

| Oligo Name | Sequence |
|---|---|
| mtgRNA97 | GCC TCG AGC TAA TAC GAC TCA CTA TAG GTC AGT GGG GGT GAG GTA AAA |
| mtgRNA99 | GCC TCG AGC TAA TAC GAC TCA CTA TAG GCT GAT CCT CCA AAT CAC CAC |
| mtgRNA101 | GCC TCG AGC TAA TAC GAC TCA CTA TAG GTT GGT ATC CTA GTG GGT GAG |
| mtgRNA103 | GCC TCG AGC TAA TAC GAC TCA CTA TAG GTT AGC CTA GCC ACA CCC CCA |
| mtgRNA105 | GCC TCG AGC TAA TAC GAC TCA CTA TAG GGC CGT TAA ACA TGT GTC AC |
| mtgRNA107 | GCC TCG AGC TAA TAC GAC TCA CTA TAG GTT AGC GAT GGA GGT AGG AT |
| mtgRNA109 | GCC TCG AGC TAA TAC GAC TCA CTA TAG GTA TAA CCT CCC CCA AAA TTC |
| mtgRNA111 | GCC TCG AGC TAA TAC GAC TCA CTA TAG GCA TTG CGA GAC GCT GGA GC |
| mtgRNA113 | GCC TCG AGC TAA TAC GAC TCA CTA TAG AAA AGA TAA AAT TTG AAA TC |
| mtgRNA115 | GCC TCG AGC TAA TAC GAC TCA CTA TAG GGT TTA TCG ATT ACA GAA C |
| mtgRNA117 | GCC TCG AGC TAA TAC GAC TCA CTA TAG AAA TCT CCT AAG TGT AAG TT |
| mtgRNA119 | GCC TCG AGC TAA TAC GAC TCA CTA TAG GGG ATT TAG AGG GTT CTG T |
| mtgRNA121 | GCC TCG AGC TAA TAC GAC TCA CTA TAG GAA AGG TTA AAA AAA GTA AA |
| mtgRNA123 | GCC TCG AGC TAA TAC GAC TCA CTA TAG AGG GTT TAC GAC CTC GAT GT |
| mtgRNA125 | GCC TCG AGC TAA TAC GAC TCA CTA TAG GAG GGT GAT GGT AGA TGT GG |
| mtgRNA127 | GCC TCG AGC TAA TAC GAC TCA CTA TAG GAT AAA TCA TAT TAT GGC CA |
| mtgRNA129 | GCC TCG AGC TAA TAC GAC TCA CTA TAG GGA ATG CTG GAG ATT GTA A |
| mtgRNA131 | GCC TCG AGC TAA TAC GAC TCA CTA TAG AAA TTA AGA ATG GTT ATG TT |
| mtgRNA133 | GCC TCG AGC TAA TAC GAC TCA CTA TAG GTT TGT GGG TTT AAG TCC CAT |
| mtgRNA135 | GCC TCG AGC TAA TAC GAC TCA CTA TAG GTG ATG CCA GCA GCT AGG AC |
| mtgRNA137 | GCC TCG AGC TAA TAC GAC TCA CTA TAG GTT CAC CGTAGG TGG CCT GAC |
| mtgRNA139 | GCC TCG AGC TAA TAC GAC TCA CTA TAG TGG AGG GTT CTT CTA CTA TT |
| mtgRNA141 | GCC TCG AGC TAA TAC GAC TCA CTA TAG GTG TTA GGA AAA GGG CAT AC |
| mtgRNA143 | GCC TCG AGC TAA TAC GAC TCA CTA TAG ATC TGT TTT TAA GCC TAA TG |
| mtgRNA145 | GCC TCG AGC TAA TAC GAC TCA CTA TAG GTT GTG TTT AAT ATT TTT AGT |

TABLE 3-continued

Additional guide RNAs used in Example 2

| Oligo Name | Sequence |
|---|---|
| mtgRNA147 | GCC TCG AGC TAA TAC GAC TCA CTA TAG GTG GTT GGT GTA AAT GAG TG |
| mtgRNA149 | GCC TCG AGC TAA TAC GAC TCA CTA TAG GAA AAC GTA GGC TTG GAT TA |
| mtgRNA151a | GCC TCG AGC TAA TAC GAC TCA CTA TAG GGC CAG TGC CCT CCT AAT TG |
| mtgRNA153a | GCC TCG AGC TAA TAC GAC TCA CTA TAG AAA TCC ACC CCT TAC GAG TG |
| mtgRNA155a | GCC TCG AGC TAA TAC GAC TCA CTA TAG GCA TTT ACC ATC TCA CTT CT |
| mtgRNA157a | GCC TCG AGC TAA TAC GAC TCA CTA TAG ATA AAA TAT GAT TAG TTC TG |
| mtgRNA159a | GCC TCG AGC TAA TAC GAC TCA CTA TAG GTA GGA GAG TGA TAT TTG ATC |
| mtgRNA161a | GCC TCG AGC TAA TAC GAC TCA CTA TAG GGT ATG AGT TTT TTT TGT TA |
| mtgRNA163 a | GCC TCG AGC TAA TAC GAC TCA CTA TAG CCG ATG AAC AGT |
| mtgRNA165 a | GCC TCG AGC TAA TAC GAC TCA CTA TAG AGT GTT AGA GTT TGG ATT AG |
| mtgRNA167a | GCC TCG AGC TAA TAC GAC TCA CTA TAG GTT TGT GTA TGA TAT GTT TG |
| mtgRNA169a | GCC TCG AGC TAA TAC GAC TCA CTA TAG GGA GTA GGG TTA GGA TGA G |
| mtgRNA171a | GCC TCG AGC TAA TAC GAC TCA CTA TAG GAC CTA GTT CAA TGA ATC TG |
| mtgRNA173a | GCC TCG AGC TAA TAC GAC TCA CTA TAG GGA CGC CTC CTA GTT TGT TA |
| mtgRNA175a | GCC TCG AGC TAA TAC GAC TCA CTA TAG GCA GGT GTC TCC TCT ATC TT |
| mtgRNA177a | GCC TCG AGC TAA TAC GAC TCA CTA TAG GAT TCA AAT TAT GTG TTT TT |
| mtgRNA179a | GCC TCG AGC TAA TAC GAC TCA CTA TAG TCA TCT CCG GTT TAC AAG AC |

Example 3

Depletion of all Human Sequences from a DNA Library (Transcriptome or all Genomic DNA) Using the CRISPR/Cas9 System Transcriptome-Wide gRNA Library:

Guide RNAs are generated, which are tiled across the entire transcriptome. The design is based on the blood transcriptome. A pipeline for the computational selection of guide RNAs spaced every ~100-200 bp across each transcript is developed, based on the knowledge that there is expected to be an NGG site every ~10-20 bp in the human genome on average). In this way, given a typical RNA-seq library insert size of ~200-500 bp, each insert is expected to contain a target site. Following completion of the design, oligo pools containing the guide RNA target sequences and surrounding motifs are ordered, allowing for subsequent addition of a T7 promoter and the invariant portion of the guide RNA sequence. This approach enables the regeneration of the libraries for a period of time before needing to order new pools. Based on an array size of 90,000 elements, it is expected that guide RNAs spaced every ~200 bp across the transcriptome with two arrays (assuming a transcriptome size of ~30M bases) will be generated. These guide RNAs are then used along with Cas9 to deplete all human DNA from an RNA-seq library as described in the previous examples. Depletion and sequencing data analysis is done as described for the previous examples.

Validation:

The described approach is tested on test RNA-seq libraries. These RNA-seq libraries are made from a mixture of human and E. coli RNA in order to simulate the types of sequences being targeted. Following depletion of the library, sequencing is performed, to get ~10× coverage of the transcriptome. As above, the proportion of all sequences mapping to human before and after depletion is measured; and the Kruskal-Wallis one-way ANOVA test can be used to determine statistical significance of depletion.

It is expected that this method, with the optimal gRNA designs, adjusting levels of Cas9 in the reaction, will achieve 90% depletion of non-ribosomal human sequences from an RNA-seq library, with less than 5% of non-human sequences being depleted.

Example 4

Enriching a Human Blood Sample for Viral or Other Pathogen Derived Sequences

A human blood sample carrying a known pathogen (e.g., Ebola) or an unknown pathogen is obtained and RNA is extracted (e.g., using a PAXgene Blood RNA extraction kit, Qiagen) and converted into a sequencing library using standard methods (e.g., using a KAPA RNA-seq library preparation kit). After cDNA creation and adapter ligation, the library is then mixed with Cas9 and a guide RNA pool targeting every ~200 bases in the human transcriptome. The reaction is incubated at 37C for 20 minutes, allowing any fragments containing the target sequences to be cleaved by Cas9. The library is then purified and amplified using adapter-specific primers. Human sequences are effectively depleted. Only uncleaved sequences are amplified, and the resulting library is enriched for viral or pathogen-derived sequences.

Example 5

Enriching a Sample from Livestock to Monitor for Viruses and Other Pathogens

In this example, the method is used to monitor viruses and other pathogens in milk and livestock.

RNA from cow milk or bovine (cow) blood is extracted and converted into a sequencing library as described in the above example. After cDNA creating and adapter ligation, the library is mixed with Cas9 and a guide RNA pool targeting ~200 bases in the Bos taurus transcriptome. The reaction is incubated at 37C for 20 minutes, allowing any fragments containing the target sequences to be cleaved by Cas9. The library is then purified and amplified using adapter-specific primers. Bovine sequences are effectively depleted. Only uncleaved sequences are amplified, and the resulting library is enriched for viral or pathogen-derived sequences. In this scenario, the cow-depleted sequencing library can be sequenced and used to monitor viruses and other pathogens in milk and livestock.

Example 6

Depletion of Large Fragments of DNA Without Adapters

This example shows a method that supports depletion without the need for adapters. In this example, the method is used for depletion experiments as described in the examples above. However, instead of cleaving a library containing adapters, the guide RNAs are chosen to cleave multiple times in a pool of fragmented DNA of large size (e.g., anywhere from 100 bp-10 kb). Following cleavage with Cas9/gRNA complexes, the DNA is subjected to size selection to remove small fragments (e.g., at least ½ or ⅓ of the average size of intact fragments). This could be assisted, for example, by treatment with Lambda exonuclease, which is a 5'phosphate specific-exonuclease that proceeds in a 5' to 3' direction and would attack any fragments that had previously been cut with Cas9. The resulting libraries can then be subjected to sequencing single-molecule sequencers that do not require sequencing adapters; or adapters can be ligated for downstream analyses.

Example 7

Depletion Followed by Exonuclease III Treatment

In some embodiments, it is desirable to remove cut fragments prior to PCR amplification or sequencing. This example illustrates a method of removing unwanted DNA after Cas9-mediated cleavage, by using Exonuclease III to degrade cleaved DNA while leaving the uncut DNA of interest intact.

As depicted in FIG. 8, the DNA mixture (containing >95% human DNA targeted for depletion, and <5% other DNA of interest) is fragmented, end-repaired and ligated to Y-shaped adapters (or circular adaptors such as NEBNext®) following regular protocols, but not amplified by PCR. The DNA mixture is then subjected to Cas9 digestion, complexed with, for example for this case, a guide RNA library against mitochondrial DNA, as described earlier. The Cas9 reaction is diluted 1:3 with TE (10 mM Tris-Cl pH 8, 1 mM EDTA) supplemented with 0.5% RNase A (Thermo Fisher Scientific), and incubated for 5 min at 37° C. Proteinase K (NEB) and then added at a final concentration of 8 units/ml and incubated for 5 min at 37° C. DNA is then recovered using the GeneJET PCR Purification Kit (Thermo Fisher Scientific) and eluted in 20 µl of 1× CutSmart® Buffer (NEB). Exonuclease III (NEB) is then added (50 units) and incubated at 37° C. for 20 min, followed by heat inactivation for 30 min at 65° C.

Exonuclease III can initiate unidirectional 3'>5' degradation of one DNA strand by using blunt end or 5' overhangs, yielding single-stranded DNA and nucleotides; it is not active on single-stranded DNA, and thus 3' overhangs, such as the Y-shaped adapter ends, are resistant to degradation. As a result, intact double-stranded DNA libraries uncut by Cas9 (for example in this case, non-mitochondrial DNA) is not be digested by Exonuclease III, while DNA molecules that have been cleaved by Cas9 (for example in this case, mitochondrial DNA) is degraded by Exonuclease III with its 3'>5' activity from the blunt ends cut by Cas9 towards the adaptors.

Thus unwanted DNA is digested. The remaining intact double-stranded DNA libraries are then recovered using the GeneJET PCR Purification Kit (Thermo Fisher Scientific) and eluted in 20 μl 10 mM Tris-Cl pH 8. Samples are then quantified using Qubit Fluorometer (Life Technologies) and sequenced on the MiSeq system (Illumina).

Alternatively, unwanted DNA can be digested, as above, while intact DNA is recovered, for example, by column purification or PCR-amplification.

Example 8

Depletion Followed by Exonuclease Bal-31

In some embodiments, it is desirable to remove cut fragments prior to PCR amplification or sequencing. This example illustrates an alternative method of removing unwanted DNA after Cas9-mediated cleavage, by using Exonuclease Bal-31 to degrade cleaved DNA while leaving the uncut DNA of interest intact.

As depicted in FIG. 9, Sequencing libraries (containing, for example >95% human DNA targeted for depletion (for example mitochondrial DNA) and <5% DNA of interest) are prepared according to conventional methods, including a PCR amplification step. Libraries (500 nM) are then tailed with poly-dG at 3' ends using Terminal Transferase (NEB) and 3 mM dGTP according to manufacturer's instruction—incubating 30 min at 37° C., then heat inactivated at 75° C. for 20 min. 3' poly-dG tailed libraries are then subjected to Cas9 digestion, complexed with, for example for this case, a guide RNA library against mitochondrial DNA, as described earlier, then heat inactivated at 75° C. for 20 min. Reactions were then diluted 1:5 in 1× Exonuclease Bal-31 Reaction Buffer (NEB), supplemented with 10 units of Exonuclease Bal-31 (NEB) and incubated at 37° C. for 30 min.

Exonuclease Bal-31 has two activities: double-stranded DNA exonuclease activity, and single-stranded DNA/RNA endonuclease activity. The double-stranded DNA exonuclease activity allows BAL-31 to degrade DNA from open ends on both strands, thus reducing the size of double-stranded DNA. The longer the incubation, the greater the reduction in size of the double-stranded DNA, making it useful for depleting medium to large DNA (>200 bp). It is noted that the single-stranded endonuclease activity of BAL-31 allows it to digest poly-A, -C or -T very rapidly, but is extremely low in digesting poly-G (Marrone and Ballantyne, 2008). Because of this nature, adding single-stranded poly-dG at 3' ends of the libraries can serve as a protection from being degraded by BAL-31, which we have verified using PCR products. As a result, DNA molecules that have been cleaved by Cas9 (for example in this case, mitochondrial DNA) will be degraded by BAL-31 with its double-stranded DNA exonuclease activity from the double-stranded blunt end cut by Cas9 towards the other end carrying poly-dG, effecting depletion; while intact DNA libraries uncut by Cas9 (for example in this case, non-mitochondrial DNA) will not be digested by BAL-31 due to their 3' end poly-dG protection.

After Exonuclease Bal-31 incubation, the reaction mixture is heat inactivated at 75° C. for 20 min, and DNA is recovered using the GeneJET PCR Purification Kit (Thermo Fisher Scientific). Samples are then quantified using Qubit Fluorometer (Life Technologies) and sequenced on the MiSeq system (Illumina).

Alternatively, unwanted DNA can be digested, as above, while intact DNA is recovered, for example, by column purification.

Example 9

Cas9 Depletion and Biotin Labeling

In some embodiments, the Cas9 cleaved products are eliminated (for example the >95% mitochondrial DNA is eliminated) and the uncut (<5% DNA of interest) DNA comprises a biotin label is purified by binding to streptavidin beads. This example illustrates a method of removing unwanted DNA after Cas9-mediated cleavage without using an exonuclease, and is depicted in FIG. 10.

A DNA mixture (containing >95% unwanted human DNA, and <5% other DNA of interest) was fragmented, end-repaired and ligated to adapters following regular protocols, then amplified by PCR using primers of Biotin-P5 (5'Biotin-AATGATACGGCGACCACCGA) and P7 (5'-CAAGCAGAAGACGGCATACGA). This ensures that the entire sequencing library possesses a 5'Biotin label only on one end of the DNA molecules. The DNA mixture is then subjected to Cas9 digestion, complexed with, for example for this case, a guide RNA library against mitochondrial DNA (the unwanted DNA), as described earlier. The Cas9 reaction is diluted 1:3 with TE (10 mM Tris-Cl pH 8, 1 mM EDTA) supplemented with 0.5% RNase A (Thermo Fisher Scientific), and incubated for 5 min at 37° C. Proteinase K (NEB) is then added at a final concentration of 8 units/ml and incubated for 5 min at 37° C. DNA molecules that are cleaved by Cas9 (for example in this case, mitochondrial DNA) will lose the Biotin labeled adaptor, thus cannot be sequenced or PCR amplified; while intact DNA libraries uncut by Cas9 (for example in this case, non-mitochondrial DNA of interest) will still carry the Biotin label. As a result, intact DNA uncut by Cas9 can then be recovered by adding streptavidin beads (Dynabeads MyOne Streptavidin C1, Thermo Fisher Scientific) to a final concentration of 2%. Beads are captured using a magnetic stand and washed 4 times with TE buffer. DNA is released from the beads by heating to 95° C. for 3 min, followed by 6 cycles of PCR using P5 and P7 primers (non-biotinylated). DNA is then purified using the GeneJET PCR Purification Kit (Thermo Fisher Scientific). Samples are then quantified using Qubit Fluorometer (Life Technologies) and sequenced on the MiSeq system (Illumina).

Example 10

Increasing Efficiency of Cas9-Mediated Depletion Using Thermostable Cas9

Although Cas9 can be used in combination with a library of guide RNAs to efficiently deplete a collection of target DNA, large amounts (>30 pmoles) of Cas9 and guide RNAs are needed. The reason for this usually >100 fold excess amount over target DNA is that, unlike classical restriction enzymes such as EcoRI, which detach completely from their target DNA after cleavage, Cas9 is not recycled after completion of the cutting reaction. Cas9 can remain tightly bound to one of the two daughter DNA product molecules (see FIG. 11, open circles on the left). As a result, more Cas9 and gRNA needs to be provided in order to achieve complete depletion of unwanted DNA. To overcome this problem, a thermostable Cas9 (defined as one that retains >90% activity after 1 min at 95° C.) complexed with guide RNAs (for example a gRNA library against human DNA) can be applied to a sequencing library of DNA mixture (containing for example 95% human DNA and 5% viral DNA). As depicted in FIG. 11 (grey circles on the right), after allowing Cas9 to digest for a period of time, the sample mixture can be boiled, which will cause DNA denaturation, as well as dissociation of gRNA and Cas9 from the DNA targets. The binding of Cas9 to gRNAs can be increased so that the Cas9-gRNA dissociates from the DNA target as an intact complex, despite of DNA denaturation. Dimethyl sulfoxide can be added to reduce the temperature required for DNA denaturation, so that the Cas9 protein structure will not be affected. Cas9 will preferentially bind to target sites that have not been cut, and a thermostable Cas9 will retain activity after boiling. Because of these features, by boiling and cooling down the reaction to 37° C., a thermostable Cas9 will remain capable of binding to its gRNA and cutting more of its substrate. By allowing the recycling of Cas9, the depletion efficiency is increased, and as less Cas9 will be needed in the reaction, the off-target (non-specific) cleavage probability will also be decreased.

Two exemplary methods to make Thermostable Cas9 are provided.

The first method is isolation of thermostable Cas9. The gene for thermostable Cas9 and its corresponding guide RNA will be identified by sequence homology in the genome of thermophilic bacteria *Streptococcus thermophilus* and *Pyrococcus furiosus*. Cas9 genes will then be cloned into an expression vector pET30 (Novagen) to express Cas9 as described in earlier sections. Guide RNA sequences will be assembled into oligonucleotides and synthetized (IDT). Active combinations of Cas9 and guide RNA will be assessed by digestion of sequenced DNA templates at 37° C. (control) and at 37° C. after treatment at 95° C. for 3×5 min.

The second method is in vitro evolution of *S. pyogenes* Cas9. The sequence of Cas9 will be mutagenized to improve its thermostability. Briefly, this will be done by site-directed mutagenesis to remove excess loop sequences, increasing the number of ionic bridges between protein domains, or by diluting into droplets and PCR to create a pool of potential mutants. All mutants will be assessed for activity and thermostability as described above.

Example 11

Controls to Monitor Depletion of Unwanted DNA and Off-Target Events

In the embodiments discussed, it is desirable to provide positive and/or negative controls. A positive control would ensure depletion of unwanted DNA is proceeding with fidelity and efficiency. A negative control would ensure that off-target cutting was minimal or nonexistent.

The positive control could consist of a sequencing library with inserts containing either all or most of the target sequences of the gRNAs included in the kit. This control would be run alongside a user's reaction to ensure that all components are working properly. After depletion with Cas9, elimination of the target sequences could be measured by gel electrophoresis or qPCR.

The negative control could consist of either 1) a set of gRNAs with less than 100% identity to the gRNAs used in the kit; for example, with 1, 2, 3, 4, 5, or more mismatches to the target-specific sequence; or 2) a DNA library having inserts with less than 100% identity to the targeted sequences of gRNAs used in the kit; for example, with 1, 2, 3, 4, 5, or more mismatches to the complementary sequence of the gRNA. This control would be run alongside a user's reaction to ensure that all components are working properly and to measure any off-target activity of the enzyme. After depletion with Cas9, the amount of off-target depletion could be measured by gel electrophoresis or qPCR.

What is claimed is:

1. A composition comprising a mixture of DNA targeted sequences for depletion and DNA sequences of interest, wherein the DNA targeted sequences for depletion and the DNA sequences of interest are adapter-ligated, wherein the adapters are ligated to both the 5' and 3' ends of both the target sequences for depletion and the sequences of interest, and wherein the DNA targeted sequences for depletion are complexed to a gRNA-CRISPR/Cas system protein complex and wherein the DNA sequences of interest are in the range of about 0.1% to about 50% of the DNA in the composition, wherein the CRISPR/Cas system protein is Cas9, Cpf1, Cas3, Cas8a-c, Cas10, Csel, Csyl, Csn2, Cas4, Csm2, or CmS.

2. The composition of claim 1, wherein the targeted sequences for depletion are from a host organism and the sequences of interest are from a non-host organism.

3. The composition of claim 1, wherein the CRISPR/Cas system protein is thermostable.

4. The composition of claim 1, wherein the composition comprises at least 10 unique CRISPR/Cas system protein-gRNA complexes.

5. The composition of claim 1, wherein the DNA targeted sequences for depletion and the DNA sequences of interest are from any one of a biological sample, a clinical sample, a forensic sample or an environmental sample.

6. The composition of claim 2, wherein the non-host organism nucleic acid comprises microbial nucleic acid sequences.

7. The composition of claim 1, wherein the gRNAs are complementary to mitochondrial DNA.

8. The composition of claim 1, wherein the gRNAs are complementary to DNA corresponding to ribosomal RNA sequences, sequences encoding globin proteins, sequences encoding a transposon, sequences encoding retroviral sequences, sequences comprising telomere sequences, sequences comprising sub-telomeric repeats, sequences comprising centromeric sequences, sequences comprising intron sequences, sequences comprising Alu repeats, sequences comprising SINE repeats, sequences comprising LINE repeats, sequences comprising dinucleic acid repeats, sequences comprising trinucleic acid repeats, sequences comprising tetranucleic acid repeats, sequences comprising poly-A repeats, sequences comprising poly-T repeats, sequences comprising poly-C repeats, sequences comprising poly-G repeats, sequences comprising AT-rich sequences, or sequences comprising GC-rich sequences.

9. The composition of claim 1, wherein the DNA targeted sequences for depletion and the DNA sequences of interest are from a sample selected from the group consisting of whole blood, plasma, serum, tears, saliva, mucous, cerebrospinal fluid, teeth, bone, fingernails, feces, urine, tissue, and a biopsy.

10. The composition of claim 2, wherein the host organism is selected from the group consisting of a human, cow, horse, sheep, pig, monkey, dog, cat, gerbil, bird, mouse, and rat.

11. The composition of claim 2, wherein the non-host organism is a bacteria, a virus or a eukaryotic parasite or pathogen.

12. The composition of claim 1, wherein the composition comprises at least $10^2$ unique CRISPR/Cas system protein-gRNA complexes.

13. The composition of claim 1, wherein the adapters are Y-shaped adapters or poly-G adapters.

14. The composition of claim 13, wherein the adapter-ligated sequences range from 50-1000 bp.

* * * * *

UNITED STATES PATENT AND TRADEMARK OFFICE
CERTIFICATE OF CORRECTION

| | | |
|---|---|---|
| PATENT NO. | : 11,692,213 B2 | Page 1 of 1 |
| APPLICATION NO. | : 16/983388 | |
| DATED | : July 4, 2023 | |
| INVENTOR(S) | : Meredith L. Carpenter et al. | |

It is certified that error appears in the above-identified patent and that said Letters Patent is hereby corrected as shown below:

In the Specification

Column 17, Line 33, "Tm" should be --$T_m$--.

Column 28, Lines 50-51, "thermophiles" should be --thermophilus--.

Column 40, Line 55, "CyS" should be --Cy5--.

Column 44, Line 41, "(50 μg/μl)" should be --(50 pg/μl)--.

Column 44, Line 53, "TABLE 2" should be --TABLE 1--.

Column 49, Line 56, "CGTAGG" should be --CGT AGG--.

Column 50, Lines 26-27, "TAG CCG" should be --TAG GCC TCT CAG CCG--.

Signed and Sealed this
Twenty-first Day of May, 2024

*Katherine Kelly Vidal*

Katherine Kelly Vidal
*Director of the United States Patent and Trademark Office*